US009056841B2

(12) United States Patent
Pomper et al.

(10) Patent No.: US 9,056,841 B2
(45) Date of Patent: Jun. 16, 2015

(54) PSMA-TARGETING COMPOUNDS AND USES THEREOF

(75) Inventors: Martin Pomper, Baltimore, MD (US); Ronnie Charles Mease, Fairfax, VA (US); Ray Sangeeta, Ellicott City, MD (US); Ying Chen, Timonium, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 396 days.

(21) Appl. No.: 13/257,499

(22) PCT Filed: Mar. 19, 2010

(86) PCT No.: PCT/US2010/028020

§ 371 (c)(1), (2), (4) Date: Sep. 19, 2011

(87) PCT Pub. No.: WO2010/108125

PCT Pub. Date: Sep. 23, 2010

(65) Prior Publication Data

US 2012/0009121 A1 Jan. 12, 2012

Related U.S. Application Data

(60) Provisional application No. 61/161,485, filed on Mar. 19, 2009, provisional application No. 61/161,484, filed on Mar. 19, 2009, provisional application No. 61/248,067, filed on Oct. 2, 2009, provisional application No. 61/248,934, filed on Oct. 6, 2009.

(51) Int. Cl.

| | |
|---|---|
| ***A61K 51/00*** | (2006.01) |
| ***A61M 36/14*** | (2006.01) |
| ***C07D 257/02*** | (2006.01) |
| ***C07D 209/14*** | (2006.01) |
| ***C07D 213/04*** | (2006.01) |
| ***C07D 249/04*** | (2006.01) |
| ***C07D 255/02*** | (2006.01) |
| ***C07D 311/14*** | (2006.01) |
| ***C07D 311/82*** | (2006.01) |

(52) U.S. Cl.

CPC ............ *C07D 257/02* (2013.01); *C07D 209/14* (2013.01); *C07D 213/04* (2013.01); *C07D 249/04* (2013.01); *C07D 255/02* (2013.01); *C07D 311/14* (2013.01); *C07D 311/82* (2013.01)

(58) Field of Classification Search

None

See application file for complete search history.

(56) References Cited

U.S. PATENT DOCUMENTS

2004/0054190 A1 3/2004 Pomper et al.

FOREIGN PATENT DOCUMENTS

WO WO-03/060523 A1 7/2003
WO WO-2009/002529 A2 12/2008
WO WO-2009/026177 A1 2/2009

OTHER PUBLICATIONS

Lee et al. JACS 2005, 127, 13164-13166.*

Mindt et al. JACS, 2006, 128, 15096-15097.*

Antunes et al., "Influence of different spacers on the biological profile of a DOTA-somatostatin analogue," Bioconjug Chem., vol. 18, pp. 84-92, 2007.

Arndt-Jovin et al., "Tumor-targeted quantum dots can help surgeons find tumor boundaries," IEEE Trans Nanobioscience, vol. 8, No. 1, pp. 65-71, Mar. 2009.

Baccala et al., "Expression of prostate-specific membrane antigen in tumor-associated neovasculature of renal neoplasms," Urology, vol. 70, pp. 385-390, 2007.

Banerjee et al., "Synthesis and evaluation of technetium-99m- and rhenium-labeled inhibitors of the prostate-specific membrane antigen (PSMA)," J. Med. Chem., vol. 51, pp. 4504-4517, 2008.

Barinka et al., "Interactions between human glutamate carboxypeptidase II and urea-based inhibitors: Structural Characterizations," J. Med. Chem, vol. 51, pp. 7737-7743, 2008.

Byun et al., "Recent Development of Therapeutic and Diagnostic Agents Targeting Glutamate Carboxypeptidase II (GCP II)" In: Drug Design of Zinc-Enzyme Inhibitors, Supuran, C. ed. Hoboken, N.J.: John Wiley & Sons, pp. 881-910, 2009.

Chandran et al., "Characterization of a targeted nanoparticle functionalized with a urea-based inhibitor of prostate-specific membrane antigen (PSMA)," Cancer Biol. Ther., vol. 7, pp. 974-982, 2008.

Chang et al., "Metastatic renal cell carcinoma neovasculature expresses prostate-specific membrane antigen," Urology, vol. 57, pp. 801-805, 2001.

Chang et al., "Prostate-specific membrane antigen is produced in tumor-associated neovasculature," Clin. Cancer Res., vol. 5, pp. 2674-2681, 1999.

Chang et al., "Prostate-specific membrane antigen: Much more than a prostate cancer marker," Mol. Urol., vol. 3 No. 3, pp. 313-320, 1999.

Chang et al., "Five different anti-prostate-specific membrane antigen (PSMA) antibodies confirm PSMA expression in tumor-associated neovasculature," Cancer Research, vol. 59, pp. 3192-3198, 1999.

Chen et al., "Radiohalogenated prostate-specific membrane antigen (PSMA)-based ureas as imaging agents for prostate cancer," J. Med. Chem. vol. 51, pp. 7933-7943, 2008.

Cheng et al., "Relationship between the inhibition constant (K1) and the concentration of inhibitor which causes 50 percent inhibition (150) of an enzymatic reaction," Biochem. Pharmcol., vol. 22, pp. 3099-3108, 1973.

Clarke, "Stabilities of trivalent metal ion complexes of the tetraacetate derivatives of 12-, 13-, and 14-membered tetraazamacrocycles," Inorg. Chim. Acta, vol. 190, pp. 37-46, 1992.

(Continued)

*Primary Examiner* — Maria Leavitt
*Assistant Examiner* — Sean R Donohue
(74) *Attorney, Agent, or Firm* — Ward and Smith, P.A.

(57) ABSTRACT

Prostate-specific membrane antigen (PSMA) targeting compounds are described. Uses of the compounds for imaging, therapy, cell sorting, and tumor mapping are also described.

3 Claims, 27 Drawing Sheets

(56) References Cited

OTHER PUBLICATIONS

Fani et al., "$^{68}$Ga-PET: a powerful generator-based alternative to cyclotron-based PET radiopharmaceuticals," Contrast Media Mol. Imaging, vol. 3, pp. 53-63, 2008.
Ghose et al., "Prediction of hydrophobic (lipophilic) properties of small organic molecules using fragmental methods: an analysis of ALOGP and CLOGP methods," J. Phys. Chem. A, vol. 102, pp. 3762-3772, 1998.
Foss et al., "Radiolabeled small-molecule ligands for prostate-specific membrane antigen: In vivo imaging in experimental models of prostate cancer," Clin. Cancer Res., vol. 11, No. 11, pp. 4022-4028, 2005.
Galsky et al., "Phase I trial of the prostate-specific membrane antigen-directed immunoconjugate MLN2704 in patients with progressive metastatic castration-resistant prostate cancer," Journal of Clinical Oncology, vol. 26, pp. 2147-2154, 2008.
Ghosh et al., "Tumor target prostate specific membrane antigen (PSMA) and its regulation in prostate cancer," J. Cell. Biochem., vol. 91, pp. 528-539, 2004.
Gong et al., "Prostate-specific membrane antigen (PSMA)-specific monoclonal antibodies in the treatment of prostate and other cancers," Cancer Metastasis Rev., vol. 18, pp. 483-490, 1999.
Gotoh et al., "A novel image-guided surgery of hepatocellular carcinoma by indocyanine green fluorescence imaging navigation," J. Surg. Oncol., pp. 75-79, 2009.
Guilarte et al., "Dysregulation of glutamate carboxypeptidase II in psychiatric disease," Schizophr Res., vol. 99, pp. 324-332, 2008.
Guilarte et al., "Glutamate Carboxypeptidase II Levels in Rodent Brain using [125I]DCIT Quantitative Autoradiography," Neurosci Lett., vol. 387, pp. 141-144, 2005.
Hamachi et al., "Single- or Dual-Mode Switching of Semisynthetic Ribonuclease S' with an Iminodiacetic Acid Moiety in Response to the Copper(II) Concentration," Chem. Eur., vol. 5, pp. 1503-1511,1999.
Haseman et al., "Capromab Pendetide imaging of prostate cancer," Cancer Biother. Radiopharm., vol. 15, pp. 131-140, 2001.
Henderson, et al., "An electrospray mass spectrometric investigation of gallium trihalide and indium trihalide solutions," Inorg. Chim. Acta., vol. 277, pp. 26-30, 1998.
Hillier et al., "Preclinical evaluation of novel glutamate-urea-lysine analogues that target prostate-specific membrane antigen as molecular imaging pharmaceuticals for prostate cancer," Cancer Res., vol. 69, pp. 6932-6940, 2009.
Humblet et al., "High-affinity near-infrared fluorescent small-molecule contrast agents for in vivo imaging of prostate-specific membrane antigen," Mol. Imaging, vol. 4, pp. 448-462, 2005.
Humblet et al., "Multivalent scaffolds for affinity maturation of small molecule cell surface binders and their application to prostate tumor targeting," J. Med. Chem., vol. 52, pp. 544-550, 2009.
Jackson et al., "Design, synthesis, and biological activity of a potent inhibitor of the neuropeptidase N-acetylated alpha-linked acidic dipeptidase," J. Med. Chem., vol. 39, pp. 619-622, 1996.
Kaiser et al., "Color test for detection of free terminal amino groups in the solid-phase synthesis of peptides," Anal. Biochem., vol. 34, pp. 595-598, 1970.
Kaushal et al., "Fluorophore-conjugated anti-CEA antibody for the intraoperative imaging of pancreatic and colorectal cancer," J. Gastrointest. Surg., vol. 12, pp. 1938-1950, 2008.
Khan et al., "Clinical indications for Gallium-68 positron emission tomography imaging," Eur. J. Surg. Oncol., vol. 35, pp. 561-567, 2009.
Kinoshita et al., "Expression of prostate-specific membrane antigen in normal and malignant human tissues," World J. Surg., vol. 30, pp. 628-636, 2006.
Kozikowski et al., "Synthesis of urea-based inhibitors as active site probes of glutamate carboxypeptidase II: efficacy as analgesic agents," J. Med. Chem., vol. 47, pp. 1729-1738, 2004.
Kularante et al., "Prostate-specific membrane antigen (PSMA)-targeted imaging and therapy of prostate cancer using a PSMA inhibitor as a homing ligand," Molecular Pharmaceutics, vol. 6, pp. 780-789, 2009.
Kularatne et al., "Design, synthesis, and preclinical evaluation of prostate-specific membrane antigen targeted (99m)Tc-radioimaging agents," Mol. Pharm., vol. 6, pp. 790-800, 2009.
Lange, "Prostascint scan for staging prostate cancer," Urology, vol. 57, pp. 402-406, 2001.
Lapi et al., "Assessment of an $^{18}$F-labeled phosphoramidate peptidomimetic as a new prostate-specific membrane antigen-targeted imaging agent for prostate cancer," J. Nucl. Med., vol. 50, pp. 2042-2048, 2009.
Liu et al., "Cell-Surface labeling and internalization by a fluorescent inhibitor of prostate-specific membrane antigen," Prostate, vol. 68, pp. 955-964, 2008.
Matsui et al., "Real-time intraoperative near-infrared fluorescence angiography for perforator identification and flap design," Plast. Reconstr. Surg., vol. 123, pp. 125e-127e, 2009.
Mease et al., "Synthesis and in vivo evaluation of N-[N-[(S)-1,3-Dicarboxypropyl]Carbamoyl]-4-[18F]Fluorobenzyl-L-Cysteine, [18F]DCFBC: A New Imaging Probe for Prostate Cancer," Clin. Cancer Res., vol. 14, pp. 3036-3043, 2008.
Milowsky et al., "Vascular targeted therapy with anti-prostate-specific membrane antigen monoclonal antibody J591 in advanced solid tumors," J. Clin. Oncol., vol. 25, pp. 540-547, Feb. 2007.
Misra et al., "Production of multimeric prostate-specific membrane antigen small-molecule radiotracers using a solid-phase 99mTc preloading strategy," J. Nucl. Med., vol. 48, pp. 1379-1389, 2007.
Murphy et al., "Measurement of serum prostate-specific membrane antigen, a new prognostic marker for prostate cancer," Urology, vol. 51, pp. 89-97, 1998.
Okuda et al., "Metastatic brain tumor surgery using fluorescein sodium: technical note," Minim. Invasive Neurosurg., vol. 50, pp. 382-384, 2007.
Pomper et al., "$^{11}$C-MCG: Synthesis, uptake selectivity and primate PET of a probe for glutamate carboxypeptidase II (NAALADase.)," Mol. Imaging, vol. 1, pp. 96-101, 2002.
Reubi et al., "Peptide-based probes for cancer imaging," J. Nucl. Med., vol. 49, pp. 1735-1738, 2008.
Rosenthal et al., "Utility of Capromab Pendetide (ProstaScint) Imaging in the Management of Prostate Cancer," Tech. Urol., vol. 7, pp. 27-37, 2001.
Sanchez-Crespo et al., "Positron flight in human tissues and its influence on PET image spatial resolution," Eur. J. Nucl. Med. Mol. Imaging, vol. 31, pp. 44-51, 2004.
Sevick-Muraca et al., "Fluorescence and absorption contrast mechanisms for biomedical optical imaging using frequency-domain techniques," Photochem. Photobiol., vol. 66, pp. 55-64, 1997.
Sheth et al., "Improved detection of ovarian cancer metastases by intraoperative quantitative fluorescence protease imaging in a preclinical model," Gynecol. Oncol., vol. 112, pp. 616-622, 2009.
Silver et al., "Prostate-specific membrane antigen expression in normal and malignant human tissues," Clinical Cancer Research, vol. 3, pp. 81-85, 1997.
Slusher et al., "Immunocytochemical localization of the N-acetyl-aspartyl-glutamate (NAAG) hydrolyzing enzyme N-acetylated alpha-linked acidic dipeptidase (NAALADase)," J.Comp. Neuro., vol. 315, pp. 217-229, 1992.
Stummer et al., "Fluorescence-guided surgery with 5-aminolevulinic acid for resection of malignant glioma: a randomised controlled multicentre phase III trial," Lancet Oncol., vol. 7, pp. 392-401, 2006.
Tasch et al., "A unique folate hydrolase, prostate-specific membrane antigen (PSMA): a target for immunotherapy?," Crit. Rev. Immunol., vol. 21, pp. 249-261, 2001.
Toda, "Intraoperative navigation and fluorescence imagings in malignant glioma surgery," Keio J. Med., vol. 57, pp. 155-161, 2008.
Wang et al., "Methods for MAG3 conjugation and $^{99m}$Tc radiolabeling of biomolecules," Nature Protocols, vol. 1, pp. 1477-1480, 2006.
Zhernosekov et al., "Processing of generator-produced $^{68}$Ga for medical application," J. Nucl. Med., vol. 48, pp. 1741-1748, 2007.

(56) References Cited

OTHER PUBLICATIONS

Zhou et al., "NAAG Peptidase inhibitors and their potential for diagnosis and therapy," Nat. Rev. Drug Discov., vol. 4, pp. 1015-1026, 2005.
Extended European Search Report issued in counterpart European Application No. 10754194.8 dated Aug. 14, 2012.
International Preliminary Report on Patentability issued in counterpart International Application No. PCT/US2010/028020 dated Sep. 20, 2011.
Maresca et al., "A Series of Halogenated Heterodimeric Inhibitors of Prostate Specific Membrane Antigen (PSMA) as Radiolabeled Probes for Targeting Prostate Cancer," J. Med. Chem., 2009, vol. 52, pp. 347-357.

* cited by examiner

SR-V-100

111In-[SR-V-100]

4 DAYS

6h

4h

2h

ABSORPTION AND EMISSION SPECTRA OF YC-27 3 IN WATER

QUANTUM YIELD OF YC-27 3 IN WATER = 0.053
REF Q.Y. (ICG IN WATER) = 0.016

$OD_{ICG}$=0.035 (λ = 775 nm) Em SPECTRA AREA = 6276

$OD_{YC27}$=0.05 (λ = 775 nm) Em SPECTRA AREA = 29509

FOR QUANTUM YIELD MEASUREMENTS, 775 nm EXCITATION WAVELENGTH USED, INTEGRATED AREA FROM EMISSION SPECTRA IN THE REGION 780-900 nm USED

DORSAL

VENTRAL

PRE-INJECTION 70.5 h PI 9.79E-1
7.00E-1
5.00E-1
2.00E-1
7.00E-2
0.00E0

3 h 1.25 h 5 h 3 h

30 MIN 5 h 3 h

30 MIN

TUBE: Pip ZERO 1

| POPULATION | #EVENTS | %PARENT | %TOTAL |
|---|---|---|---|
| ALL EVENTS | 1,334,712 | | 100.0 |
| P1 | 991,055 | 74.3 | 74.3 |
| P2 | 0 | 0.0 | 0.0 |
| P3 | 55 | 0.0 | 0.0 |

TUBE: Pip 1000-1

| POPULATION | #EVENTS | %PARENT | %TOTAL |
|---|---|---|---|
| ALL EVENTS | 1,404,987 | | 100.0 |
| P1 | 1,043,719 | 74.3 | 74.3 |
| P2 | 63 | 0.0 | 0.0 |
| P3 | 145 | 0.0 | 0.0 |

TO FIG. 25B

PSMA-TARGETING COMPOUNDS AND USES THEREOF

CROSS-REFERENCE TO RELATED APPLICATION

This application claims priority to U.S. Provisional Application No. 61/161,484 filed Mar. 19, 2009, 61/161,485, filed Mar. 19, 2009, 61/248,067, filed Oct. 2, 2009, and 61/248,934, filed Oct. 6, 2009. The entire content of each Provisional application is hereby incorporated by reference in their entirety.

This invention was made using U.S. Government support under NIH grant NIH U24 CA92871. The government has certain rights in this invention.

BACKGROUND

1. Field of the Invention

The present invention relates to prostate specific membrane antigen (PSMA) binding compounds, chemical precursors of PSMA binding compounds and imaging methods of using the compounds.

2. Background

Prostate cancer (PCa) is the most commonly diagnosed malignancy and the second leading cause of cancer-related death in men in the United States (*Cancer Facts & Figures*; American Cancer Society: Atlanta, Ga., 2009). In 2009, it is estimated that 192,000 men will be diagnosed with prostate cancer and 27,000 men will die of the disease. Only one half of tumors due to PCa are clinically localized at diagnosis and one half of those represent extracapsular spread. Localization of that spread as well as determination of the total body burden of PCa have important implications for therapy, particularly as new combination and focal therapies become available.

The prostate-specific membrane antigen (PSMA), while expressed in prostate tumor epithelium, has a curious property in that it is expressed in the neovasculature of many solid tumors but not in that of prostate cancer (Chang et al., Cancer Res., vol. 59, pp. 3192-3198, 1999; Chang et al., Clin. Cancer Res., vol. 5, pp. 2674-2681, 1999; Gong et al., Cancer Metastasis Rev., vol. 18, pp. 483-490, 1999; Chang et al., Mol. Urol., vol. 3, pp. 313-320, 1999; Baccala et al., Urology, vol. 70, pp. 385-390, 2007; Chang et al., Urology, vol. 57, pp. 801-805, 2001 Milowsky et al., J. Clin. Oncol., vol. 25, pp. 540-547, 2007). Because of that property, an $^{111}$In-labeled monoclonal antibody to an extracellular epitope of PSMA, $^{111}$In-J591, was capable of identifying renal, bladder, lung, breast, colorectal and pancreatic tumors in a Phase I clinical imaging study (Milowsky et al., J. Clin. Oncol., vol. 25, pp. 540-547, 2007). That study validated $^{111}$In-J591 as a vascular targeting agent in human subjects. Since then other reports have further studied PSMA expression in certain tumor types. Baccala et al. noted that clear cell renal cell carcinoma expresses significantly more PSMA in its neovasculature than does the papillary variety (Baccala et al., Urology, vol. 70, pp. 385-390, 2007). Furthermore, angiomyolipoma, a benign renal lesion, did not express PSMA. As an enzyme with an extracellular active site, PSMA represents an excellent target for imaging and therapy directed toward solid tumor neovasculature in addition to prostate cancer itself. PSMA-based agents can report on the presence of this marker, which is increasingly recognized as an important prognostic determinate in PCa (Murphy et al., *Urology*, vol. 51, pp. 89-97, 1998). It is also the target for a variety of new PCa therapies (Galsky et al., *J Clin Oncol*, vol. 26, pp. 2147-2154, 2008).

ProstaScint™ is an $^{111}$In-labeled monoclonal antibody against PSMA that is clinically available for imaging PCa. Radioimmunotherapy based on ProstaScint™ and radiolabeled variations of this antibody are fraught with similar difficulties to the use of radiolabeled antibodies for imaging, including prolonged circulation times, poor target to nontarget tissue contrast, unpredictable biological effects and the occasional need for pre-targeting strategies, limiting the utility of these agents (Lange, P. H., *Urology*, vol. 57, pp. 402-406, 2001; Haseman et al., *Cancer Biother Radiopharm*, vol. 15, pp. 131-140, 2000; Rosenthal et al., *Tech Urol*, vol. 7, pp. 27-37, 2001). Furthermore, antibodies may have less access to tumor than low molecular weight agents, which can be manipulated pharmacologically.

The development of low molecular weight radiotherapeutic agents is much different from developing radiopharmaceuticals for imaging in that longer tumor residence times can often be important for the former.

Complete detection and eradication of primary tumor and metastatic foci are required to effect a cure in patients with cancer; however, current preoperative assessment often misses small metastatic deposits. More sensitive imaging techniques than computed tomography, magnetic resonance imaging and even positron emission tomography (PET), which can be used easily in the operating suite, are required. An old technique, recently revisited because of improved optics and fluorescent dye chemistry, is intraoperative photodiagnosis (PDD) (Toda, Keio J. Med., vol. 57, pp. 155-161, 2008). Fluorescein dyes have been used intraoperatively to identify brain tumors and verify the clarity of tumor margins since 1948 (Toda, Keio J. Med., vol. 57, pp. 155-161, 2008). A recent report describes its utility in identifying brain metastases (Okuda et al., Minim. Invasive Neurosurg., vol. 50, pp. 382-384, 2007). A long history of the use of 5-aminolevulinic acid (5-ALA) for brain tumor resection is also evident, and its use has been associated with improvement in progression-free survival (Stummer et al., Lancet Oncol., vol. 7, pp. 392-401, 2006). PDD can be performed easily during surgery due to the lack of a need for complex imaging equipment. All that is needed is a light-emitting diode to excite the fluorophore, which can be administered systemically or "painted" on the tissue directly. More recent incarnations of PDD have used quantum dots (Arndt-Jovin et al., IEEE Trans Nanobioscience, 2009), and more advanced dyes, such as indocyanine green (ICG) (Gotoh et al., J. Surg. Oncol., 2009), which emit in the near-infrared (NIR) region of the spectrum, enabling reasonable tissue penetration of emitted (and detected) light. Applications have included nontargeted approaches, such as preoperative evaluation of the vascular integrity of surgical flaps or identification of nodules of hepatocellular carcinoma (Matsui et al., Plast. Reconstr. Surg., vol. 123, pp. 125e-127e, 2009). Targeted approaches are also emerging, such as use of a fluorophore-conjugated anti-CEA antibody to identify colon or pancreatic cancer (Kaushal et al., J. Gastrointest. Surg., vol. 12, pp. 1938-1950, 2008), or the use of NIR activatable probes that emit light only when cleaved by a tumor-associated protease (Sheth et al., Gynecol. Oncol., vol. 112, pp. 616-622, 2009).

Recently, the application of $^{68}$Ga-labeled peptides has attracted considerable interest for cancer imaging because of the physical characteristics of Ga-68 (Reubi et al., *J Nucl Med*, vol. 49, pp. 1735-1738, 2008). Ga-68 is available from an in-house $^{68}$Ge/$^{68}$Ga generator ($^{68}$Ge, $t_{1/2}$=270.8 day), which renders it independent of an onsite cyclotron. Therefore, $^{68}$Ga-based PET agents possess significant commercial potential and serve as a convenient alternative to cyclotron-based isotopes for positron emission tomography (PET), such as $^{18}$F or $^{124}$I. $^{68}$Ga has a high positron-emitting fraction (89% of its total decay). The maximum positron energy of $^{68}$Ga (max. energy=1.92 MeV, mean=0.89 MeV) is higher than that of $^{18}$F (max=0.63 MeV, mean=0.25 MeV). However, a study of spatial resolution using Monte Carlo analysis revealed that under the assumption of 3 mm spatial resolution for most PET detectors, the full-width-at-half-maximum (FWHM) of $^{18}$F and $^{68}$Ga are indistinguishable in soft tissue (3.01 mm vs. 3.09 mm) (Sanchez-Crespo et al., *Eur J Nucl*

*Med Mol Imaging*, vol. 31, pp. 44-51, 2004). That finding implies that with the standard spatial resolution of 5 to 7 mm for current clinical scanners, image quality using $^{68}$Ga-based radiotracers will likely be indistinguishable from that of $^{18}$F-based agents, stimulating interest in the development of $^{68}$Ga-labeled compounds for medical imaging (Sanchez-Crespo et al., *Eur J Nucl Med Mol Imaging, vol.* 31, pp. 44-51, 2004; Khan et al., *Eur J Surg Oncol*, vol. 35, pp. 561-567, 2009; Fani et al., *Contrast Media Mol Imaging*, vol. 3, pp. 67-77, 2008). With a physical half-life of 68 min, $^{68}$Ga is also matched nicely to the pharmacokinetics of many peptides used for imaging. Few $^{68}$Ga-labeled, mechanism-based radiotracers for prostate cancer have been reported previously, and none for PSMA. Furthermore, $^{68}$Ga is introduced to biomolecules through macrocyclic chelators, which allows possible kit formulation and wide availability of the corresponding imaging agents.

SUMMARY OF THE INVENTION

The present invention satisfies the long standing and unmet need for new imaging and therapeutic compounds for targeting prostate cancer and cancer angiogenesis. The present invention, in particular, provides therapeutic compounds and imaging agents which differ from the prior art in modifications which were not previously known or suggested. Furthermore, the invention provides imaging agents that offer better contrast between target tissues and non-target tissues. The invention also provides compounds with greater cellular retention and low molecular weight.

Embodiments of the invention include compounds having the structure

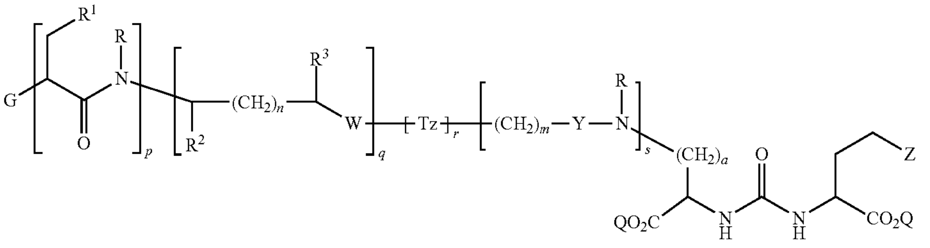

wherein the subunits associated with elements p, q, r, and s may be in any order. Z is tetrazole or $CO_2Q$; each Q is independently selected from hydrogen or a protecting group, a is 1, 2, 3, or 4, and R is each independently H or $C_1$-$C_4$ alkyl.

Variable r is 0 or 1. Tz is a triazole group selected from the group consisting of

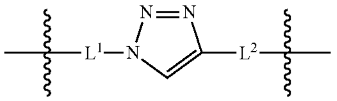

and

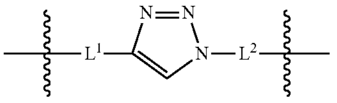

where $L^1$ is

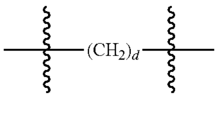

or

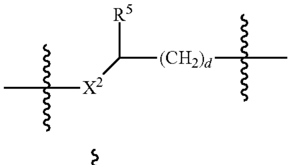

, $L^2$ is

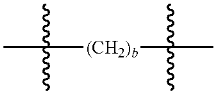

or

-continued

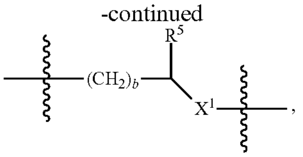

, $X^1$ is —NRC(O)—, —NRC(O)NR—, —NRC(S)NR—, or —NRC(O)O—; $X^2$ is —C(O)NR—, —NRC(O)NR—, —NRC(S)NR—, or —OC(O)NR—; $R^5$ is H, $CO_2H$, or $CO_2R^6$, where $R^6$ is a $C_1$-$C_6$ alkyl, $C_2$-$C_{12}$ aryl, or $C_4$-$C_{16}$ alkylaryl; b is 1, 2, 3, or 4; and d is 1, 2, 3, or 4.

Variable q is 0 or 1. W is —NRC(O)—, —NRC(O)NR—, NRC(S)NR—, —NRC(O)O—, —OC(O)NR—, —OC(O)—, —C(O)NR—, or —C(O)O—; $R^2$ and $R^3$ are independently H, $CO_2H$, or $CO_2R^4$, where $R^4$ is a $C_1$-$C_6$ alkyl, $C_2$-$C_{12}$ aryl, or $C_4$-$C_{16}$ alkylaryl, wherein if one of $R^2$ and $R^3$ is $CO_2H$ or $CO_2R^4$, then the other is H; n is 1, 2, 3, 4, 5 or 6.

Variable s is 0 or 1. Y is —C(O)—, —NRC(O)—, —NRC(S)—, —OC(O); and m is 1, 2, 3, 4, 5, or 6.

Variable p is 0, 1, 2, or 3, and when p is 2 or 3, each $R^1$ may be the same or different. $R^1$ is H, $C_1$-$C_6$ alkyl, $C_2$-$C_{12}$ aryl, or $C_4$-$C_{16}$ alkylaryl.

G is a moiety selected from the group consisting of

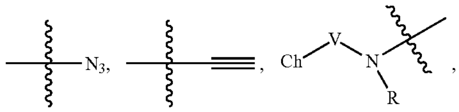

,

-continued

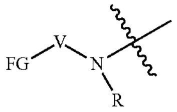

,

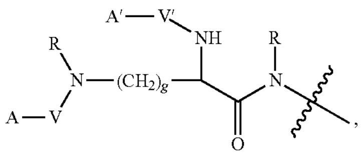

, and

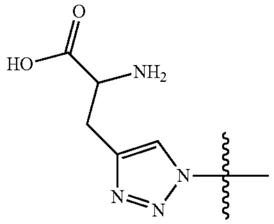

where Ch is a metal chelating moiety, optionally including a chelated metal; FG is a fluorescent dye moiety which emits in the visible or near infrared spectrum; one of A and A' is Ch and the other is FG; V and V' are independently —C(O)—, —NRC(O)—, —NRC(S)—, or —OC(O)—; and g is 1, 2, 3, 4, 5, or 6. The following conditions also apply:

1) when G is

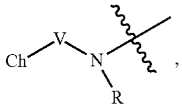
, or
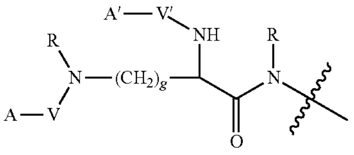

and r is 0, then q and s are both 1;

2) when G is

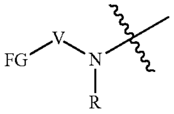

and r is 0, then q and s are both 0 or both 1;

3) when G is

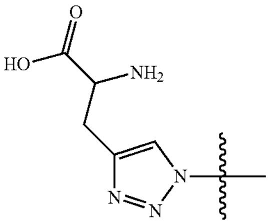 [SMILES: *n1cc(CC(N)C(=O)O)nn1]

then p is 0 and $R^2$ is H, and the structure optionally includes a chelated metal ion.

4) when G is

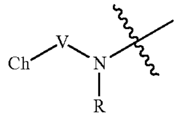

and r is 0, then if p is 0, then one of $R^2$ and $R^3$ is $CO_2R^4$, and the other is H; and 5) when g is

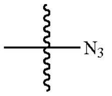
or
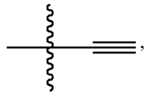
, then r is 0.

Embodiments include compounds having the structure

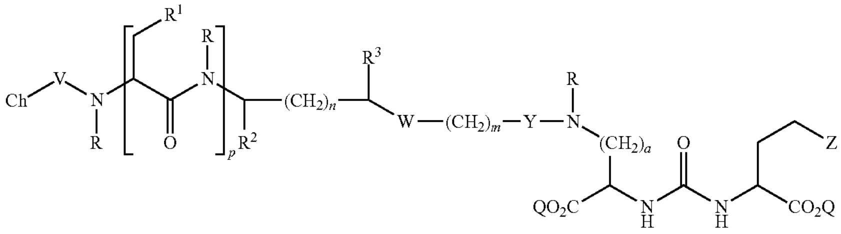

wherein Z is tetrazole or $CO_2Q$; each Q is independently selected from hydrogen or a protecting group, a is 1, 2, 3, or 4, and R is each independently H or $C_1$-$C_4$ alkyl. Ch is a metal chelating moiety optionally including a chelated metal. W is —NRC(O)—, —NRC(O)NR—, NRC(S)NR—, —NRC(O)O—, —OC(O)NR—, —OC(O)—, —C(O)NR—, or —C(O)O—. Y is —C(O)—, —NRC(O)—, —NRC(S)—, —OC(P). V is —C(O)—, —NRC(O)—, —NRC(S)—, or —OC(O)—. In exemplary embodiments m is 1, 2, 3, 4, 5, or 6; n is 1, 2, 3, 4, 5 or 6; and p is 0, 1, 2, or 3, and when p is 2 or 3, each $R^1$ may be the same or different. $R^1$ is H, $C_1$-$C_6$ alkyl, $C_2$-$C_{12}$ aryl, or $C_4$-$C_{16}$ alkylaryl. $R^2$ and $R^3$ are independently H, $CO_2H$, or $CO_2R^4$, where $R^4$ is a $C_1$-$C_6$ alkyl, $C_2$-$C_{12}$ aryl, or $C_4$-$C_{16}$ alkylaryl, wherein when one of $R^2$ and $R^3$ is $CO_2H$ or $CO_2R^4$, the other is H, and when p is 0, one of $R^2$ and $R^3$ is $CO_2R^4$, and the other is H.

Some embodiments further include a chelated metal. In some embodiments, the chelated metal is Tc, In, Ga, Y, Lu, Re, Cu, Ac, Bi, Pb, Sm, Sc, Co, Ho, Gd, Eu, Tb, or Dy. In some embodiments, the chelated metal an isotope, for example. In some embodiments, the isotope is Tc-94m, Tc-99m, In-111, Ga-67, Ga-68, Y-86, Y-90, Lu-177, Re-186, Re-188, Cu-64, Cu-67, Co-55, Co-57, Sc-47, Ac-225, Bi-213, Bi-212, Pb-212, Sm-153, Ho-166, or Dy-166. Embodiments include compounds having the structure

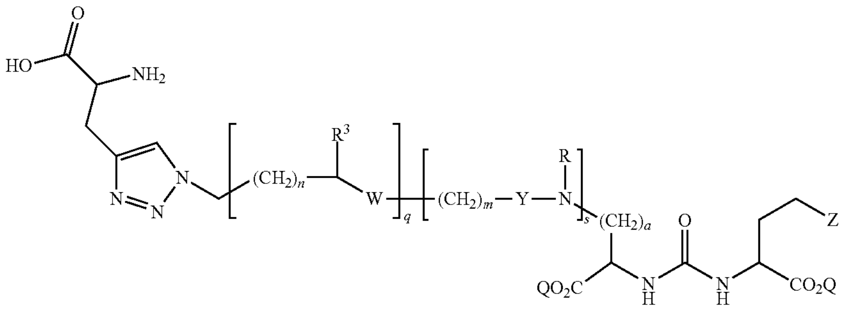

optionally including a chelated metal ion. Z is tetrazole or $CO_2Q$; each Q is independently selected from hydrogen or a protecting group, and a is 1, 2, 3, or 4. R is each independently H or $C_1$-$C_4$ alkyl. W is —NRC(O)—, —NRC(O)NR—, NRC(S)NR—, —NRC(O)O—, —OC(O)NR—, —OC(O)—, —C(O)NR—, or —C(O)O—. Y is —C(O)—, —NRC(O)—, —NRC(S)—, —OC(O)—;

In exemplary embodiments m is 1, 2, 3, 4, 5, or 6; n is 1, 2, 3, 4, 5 or 6; q is 0 or 1; and s is 0 or 1. $R^3$ is H, $CO_2H$, or $CO_2R^4$, where $R^4$ is a $C_1$-$C_6$ alkyl, $C_2$-$C_{12}$ aryl, or $C_4$-$C_{16}$ alkylaryl. Some embodiments further include a chelated metal ion. In some embodiments, the metal ion is Tc, Re, Cu, or Ga. In some embodiments, the metal ion is Tc-99m, Re-186, Re-188, Cu-64, or Ga-68. In some embodiments, the metal ion is Tc-99m.

Embodiments include compounds having the structure

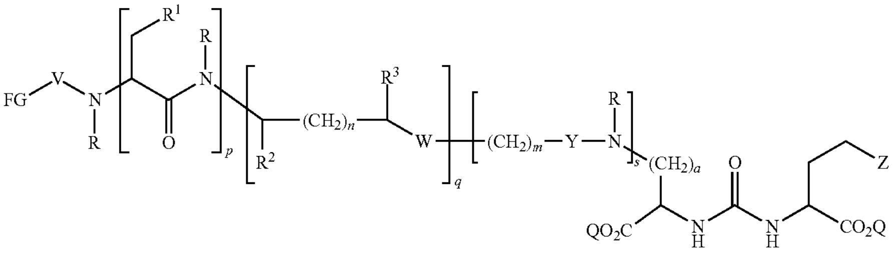

where p, q, and s are in the order drawn, and q and s are either both 0 or both 1. Z is tetrazole or $CO_2Q$; each Q is independently selected from hydrogen or a protecting group, and a is 1, 2, 3, or 4. FG is a fluorescent dye moiety which emits in the visible or near infrared spectrum. R is each independently H or $C_1$-$C_4$ alkyl. V is —C(O)— or —NRC(O)— or —NRC(S)—. W is —NRC(O)—, —NRC(O)NR—, NRC(S)NR—, —NRC(O)O—, —OC(O)NR—, —OC(O)—, —C(O)NR—, or —C(O)O—. Y is —C(O)—, —NRC(O)—, —NRC(S)—, —OC(O). In exemplary embodiments m is 1, 2, 3, 4, 5, or 6; n is 1, 2, 3, 4, 5 or 6; p is 0, 1, 2, or 3, and when p is 2 or 3, each R' may be the same or different. $R^1$ is H, $C_1$-$C_6$ alkyl, $C_2$-$C_{12}$ aryl, or $C_4$-$C_{16}$ alkylaryl. $R^2$ and $R^3$ are independently H, $CO_2H$, or $CO_2R^4$, where $R^4$ is a $C_1$-$C_6$ alkyl, $C_2$-$C_{12}$ aryl, or $C_4$-$C_{16}$ alkylaryl, wherein when one of $R^2$ and $R^3$ is $CO_2H$ or $CO_2R^4$, the other is H. In some embodiments, the fluorescent dye moiety emits in the near infrared spectrum.

Embodiments include compounds having the structure

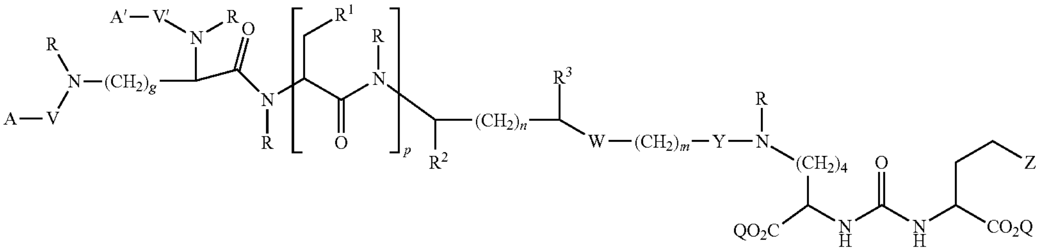

wherein Z is tetrazole or $CO_2Q$; each Q is independently selected from hydrogen or a protecting group, and a is 1, 2, 3, or 4. One of A and A' is Ch and the other is FG, where FG is a fluorescent dye moiety which emits in the visible or near infrared spectrum and Ch is metal chelating moiety optionally including a chelated metal. R is each independently H or $C_1$-$C_4$ alkyl. V or V' are independently —C(O)—, —NRC(O)—, or —NRC(S)—. W is —NRC(O)—, —NRC(O)NR—, NRC(S)NR—, —NRC(O)O—, —OC(O)NR—, —OC(O)—, —C(O)NR—, or —C(O)O—. Y is —C(O)—, —NRC(O)—, —NRC(S)—, —OC(O). In exemplary embodiments m is 1, 2, 3, 4, 5, or 6; n is 1, 2, 3, 4, 5 or 6; and g is 1, 2, 3, 4, 5, or 6; p is 0, 1, 2, or 3, and when p is 2 or 3, each $R^1$ may be the same or different. $R^1$ is H, $C_1$-$C_6$ alkyl, $C_2$-$C_{12}$ aryl, or $C_4$-$C_{16}$ alkylaryl. $R^2$ and $R^3$ are independently H, $CO_2H$, or $CO_2R^4$, where $R^4$ is a $C_1$-$C_6$ alkyl, $C_2$-$C_{12}$ aryl, or $C_4$-$C_{16}$ alkylaryl, wherein when one of $R^2$ and $R^3$ is $CO_2H$ or $CO_2R^4$, the other is H. In some embodiments, the fluorescent dye moiety emits in the near infrared spectrum. Some embodiments further include a chelated metal.

Embodiments include compounds having the structure

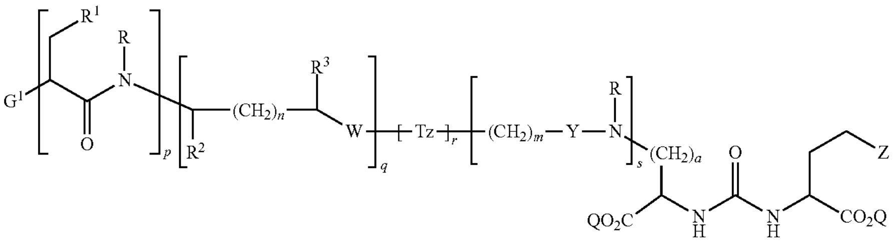

wherein subunits associated with p, q, r, and s may be in any order. Z is tetrazole or $CO_2Q$; each Q is independently selected from hydrogen or a protecting group, and a is 1, 2, 3, or 4. R is each independently H or $C_1$-$C_4$ alkyl. In this exemplary embodiment r is 1. Tz is a triazole group having the structure

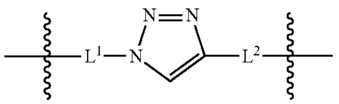

or

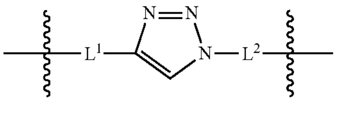

where

-continued $L^1$ is

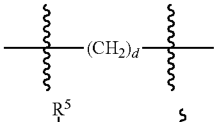

or

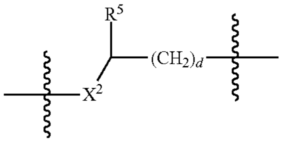

;

$L^2$ is

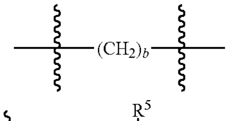

or

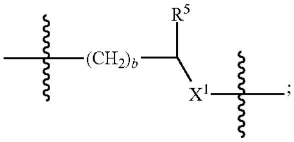

;

$X^1$ is —NRC(O)—, —NRC(O)NR—, NRC(S)NR—, or —NRC(O)O—; $X^2$ is —C(O)NR—, —NRC(O)NR—, NRC(S)NR—, or —OC(O)NR—; $R^5$ is H, $CO_2H$, or $CO_2R^6$, where $R^6$ is a $C_1$-$C_6$ alkyl, $C_2$-$C_{12}$ aryl, or $C_4$-$C_{16}$ alkylaryl; b is 1, 2, 3, or 4; and d is 1, 2, 3, or 4. In exemplary embodiments q is 0 or 1, W is —NRC(O)—, —NRC(O)NR—, NRC(S)NR—, —NRC(O)O—, —OC(O)NR—, —OC(O)—, —C(O)NR—, or —C(O)O—; n is 1, 2, 3, 4, 5 or 6; and $R^2$ and $R^3$ are independently H, $CO_2H$, or $CO_2R^4$, where $R^4$ is a $C_1$-$C_6$ alkyl, $C_2$-$C_{12}$ aryl, or $C_4$-$C_{16}$ alkylaryl, wherein if one of $R^2$ and $R^3$ is $CO_2H$ or $CO_2R^4$, then the other is H. In exemplary embodiments is 0 or 1; Y is —C(O)—, —NRC(O)—, —NRC(S)—, —OC(O); and m is 1, 2, 3, 4, 5, or 6. In exemplary embodiments p is 0, 1, 2, or 3, and when p is 2 or 3, each $R^1$ may be the same or different; and $R^1$ is H, $C_1$-$C_6$ alkyl, $C_2$-$C_{12}$ aryl, or $C_4$-$C_{16}$ alkylaryl. $G^1$ is a moiety selected from the group consisting of

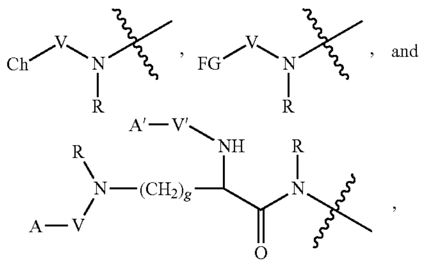

where Ch is a metal chelating moiety, optionally including a chelated metal; FG is a fluorescent dye moiety which emits in the visible or near infrared spectrum; one of A and A' is Ch and the other is FG; V and V' are each independently —C(O)—, —NRC(O)—, —NRC(S)—, or —OC(O)—; and g is 1, 2, 3, 4, 5, or 6. In some embodiments, the fluorescent dye moiety emits in the near infrared spectrum. Some embodiments include a chelated metal.

Embodiments of the invention include methods of imaging one or more cells, organs or tissues by exposing the cell to or administering to a organism an effective amount of a compound discussed above, where the compound includes a fluorescent dye moiety, or a metal isotope suitable for imaging.

Embodiments of the invention include methods of treating a tumor comprising administering a therapeutically effective amount of a compound discussed above, where the compound includes a therapeutically effective radioisotope.

Embodiments of the invention include methods for sorting cells by exposing the cells to a compound discussed above, where the compound includes a fluorescent dye moiety, followed by separating cells which bind the compound from cells which do not bind the compound.

Embodiments of the invention include methods of intraoperative tumor mapping comprising administering an effective amount of a compound discussed above to a subject, where the compound includes a fluorescent dye moiety.

DETAILED DESCRIPTION OF EXEMPLARY EMBODIMENTS

Figure 1:
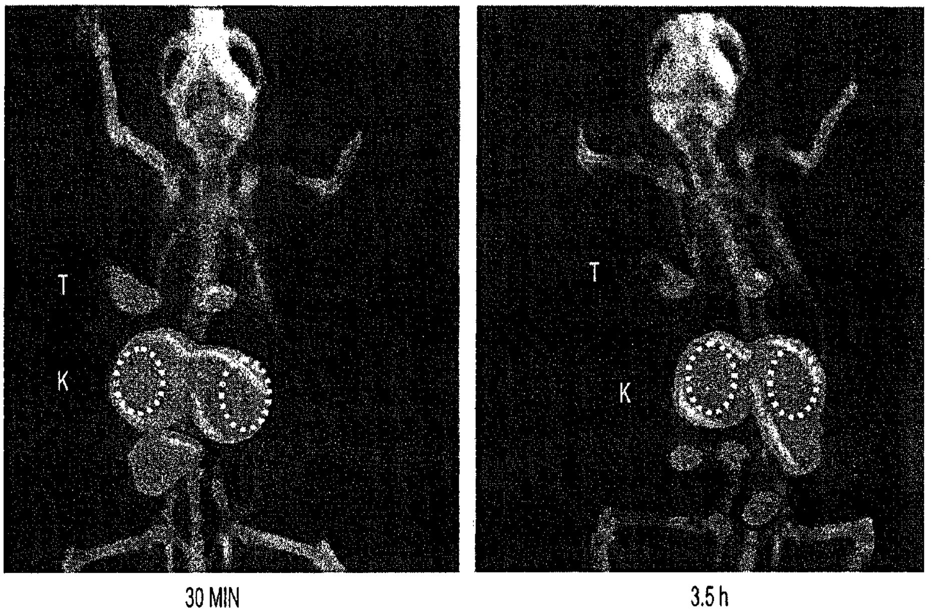
FIG. 1 shows SPECT-CT images of a PSMA+ LNCaP tumor-bearing mouse injected intravenously with exemplary compound [$^{99m}$Tc]SRV32.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

Where a range of values is provided in the present application, it is understood that each intervening value, to the tenth of the unit of the lower limit unless the context clearly dictates otherwise, between the upper and lower limit of that range and any other stated or intervening value in that stated range, is encompassed within the invention. The end values of any range are included in the range.

DEFINITIONS

The following terms below generally have the meaning that would be readily understood by persons skilled in the art. The definitions are provided herein for clarity. Where a definition excludes an art-recognized meaning, the term should be taken to have the meaning set forth below. Where the art-recognized meaning and the meaning below differ but are not exclusive, the intended meaning is clear by the context in which it is used.

As used herein, "agent" is a non-peptide, small molecule compound.

By "cell substrate" is meant the cellular or acellular material (e.g., extracellular matrix, polypeptides, peptides, or other molecular components) that is in contact with the cell.

By "control" is meant a standard or reference condition.

By "disease" is meant any condition or disorder that damages or interferes with the normal function of a cell, tissue, organ or subject.

By "effective amount" is meant a quantity sufficient to produce a measurable difference, when compared with a control. For example, an amount sufficient to produce a measurable image, when the compound is used for imaging, or an amount sufficient to ameliorate the symptoms of a disease, when the compound is used for therapy. The effective amount of an active therapeutic agent for the treatment of a disease or injury varies depending upon the manner of administration, the age, body weight, and general health of the subject. Ultimately, the attending clinician will decide the appropriate amount and dosage regimen.

By "modifies" is meant alters. An agent that modifies a cell, substrate, or cellular environment produces a biochemical alteration in a component (e.g., polypeptide, nucleotide, or molecular component) of the cell, substrate, or cellular environment.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "subject" is meant a mammal, including, but not limited to, a human or non-human mammal, such as a bovine, equine, canine, ovine, or feline.

By "therapeutic delivery device" is meant any device that provides for the release of a therapeutic agent. Exemplary therapeutic delivery devices include tablets and pills, described below, as well as syringes, osmotic pumps, indwelling catheters, delayed-release and sustained-release biomaterials.

As used herein, the terms "treat," treating," "treatment," "therapeutic" and the like refer to reducing or ameliorating a disorder and/or symptoms associated therewith. It will be appreciated that, although not precluded, treating a disorder or condition does not require that the disorder, condition or symptoms associated therewith be completely eliminated.

The compounds herein described may have one or more asymmetric centers or planes. Compounds of the present invention containing an asymmetrically substituted atom may be isolated in optically active or racemic forms. It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent, or chromatography, using, for example a chiral HPLC column. Many geometric isomers of olefins, C═N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

The compounds herein described may have one or more charged atoms. For example, the compounds may be zwitterionic, but may be neutral overall. Other embodiments may have one or more charged groups, depending on the pH and other factors. In these embodiments, the compound may be associated with a suitable counter-ion. It is well known in the art how to prepare salts or exchange counter-ions. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Counter-ions may be changed, for example, by ion-exchange techniques such as ion-exchange chromatography. All zwitterions, salts and counter-ions are intended, unless the counter-ion or salt is specifically indicated. In certain embodiments, the salt or counter-ion may be pharmaceutically acceptable, for administration to a subject. Pharmaceutically acceptable salts are discussed later.

As used herein, a "protecting group" is a chemical substituent which can be selectively removed by readily available reagents which do not attack the regenerated functional group or other functional groups in the molecule. Suitable protecting groups are known in the art and continue to be developed. Suitable protecting groups may be found, for example in Wutz et al. ("Greene's Protective Groups in Organic Synthesis, Fourth Edition," Wiley-Interscience, 2007). Protecting groups for protection of the carboxyl group, as described by Wutz et al. (pages 533-643), are used in certain embodiments. In some embodiments, the protecting group is removable by treatment with acid. Specific examples of protecting groups include but are not limited to, benzyl, p-methoxybenzyl (PMB), tertiary butyl ($^t$Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr). Persons skilled in the art will recognize appropriate situations in which protecting groups are required and will be able to select an appropriate protecting group for use in a particular circumstance.

As used herein, "alkyl" is intended to include branched, straight-chain, and cyclic saturated aliphatic hydrocarbon groups. Examples of alkyl include, but are not limited to, methyl, ethyl, n-propyl, iso-propyl, n-butyl, sec-butyl, tert-butyl, n-pentyl, and sec-pentyl. In certain embodiments, alkyl groups are $C_1$-$C_6$ alkyl groups or $C_1$-$C_4$ alkyl groups. Particular alkyl groups are methyl, ethyl, propyl, butyl, and 3-pentyl. The term "$C_1$-$C_6$ alkyl" as used herein means straight-chain, branched, or cyclic $C_1$-$C_6$ hydrocarbons which are completely saturated and hybrids thereof such as (cycloalkyl) alkyl. Examples of $C_1$-$C_6$ alkyl substituents include methyl (Me), ethyl (Et), propyl (including n-propyl (n-Pr, $^n$Pr), iso-propyl (i-Pr, $^i$Pr), and cyclopropyl (c-Pr, $^c$Pr)), butyl (including n-butyl (n-Bu, $^n$Bu), iso-butyl (i-Bu, $^i$Bu), sec-butyl (s-Bu, $^s$Bu), tert-butyl (t-Bu, $^t$Bu), or cyclobutyl (c-Bu, $^n$Bu)), and so forth. "Cycloalkyl" is intended to include saturated ring groups, such as cyclopropyl, cyclobutyl, cyclopentyl, or cyclohexyl. Cycloalkyl groups typically will have 3 to about 8 ring members. In the term "(cycloalkyl)alkyl", cycloalkyl, and alkyl are as defined above, and the point of attachment is on the alkyl group. This term encompasses, but is not limited to, cyclopropylmethyl, cyclopentylmethyl, and cyclohexylmethyl. The alkyl group may be substituted or unsubstituted. Substituents are not counted towards the total number of atoms in the alkyl group, so long as the total atoms in the substituent(s) are not larger than the alkyl group.

As used herein, the term "aryl" includes aromatic groups that contain 1 to 3 separate or fused rings and from 2 to about 12 carbon atoms, and up to 3 heteroatoms as ring members. Examples of heteroatoms include nitrogen, oxygen or sulfur atoms. The aryl group may have 0, 1, 2 or 3 heteroatoms as ring members. Examples of aryl groups include but are not limited to phenyl, biphenyl and naphthyl, including 1-napthyl and 2-naphthyl. Examples of aryl groups having heteroatoms include quinolinyl, isoquinolinyl, quinazolinyl, pyridyl, pyrazinyl, pyrimidyl, furanyl, pyrrolyl, thienyl, oxadiazolyl, thiadiazolyl, thiazolyl, triazinyl, oxazolyl, isoxazolyl, imidazolyl, indolyl, benzofuranyl, and benzothiazolyl, among others. The aryl group may be substituted or unsubstituted. Substituents are not counted towards the total number of atoms in the aryl group, so long as the total atoms in the substituent(s) are not larger than the aryl group.

As used herein, the term "alkylaryl" includes alkyl groups, as defined above, substituted by aryl groups, as defined above. The aryl group may be connected at any point on the alkyl group. The term $C_4$-$C_{16}$ alkylaryl includes alkylaryl groups having a total of 4 to 16 carbon atoms, counting the carbon atoms on the alkyl group and aryl group together. Examples of alkylaryl groups include but are not limited to benzyl (phenylmethyl), phenylethyl, and naphthylmethyl. The alkylaryl group may be substituted or unsubstituted. Substituents are not counted towards the total number of atoms in the alkylaryl group, so long as the total atoms in the substituent(s) are not larger than the alkylaryl group.

The term "substituted," as used herein, means that any one or more hydrogens on the designated atom or group is replaced with a substituent, provided that the designated atom's normal valence is not exceeded, and that the substitution results in a stable compound. When a substituent is oxo (keto, i.e., =O), then 2 hydrogens on an atom are replaced. The present invention is intended to include all isotopes (including radioisotopes) of atoms occurring in the present compounds. When the compounds are substituted, they may be so substituted at one or more available positions, typically 1, 2, 3 or 4 positions, by one or more suitable groups such as those disclosed herein. Suitable groups that may be present on a "substituted" group include e.g., halogen; cyano; hydroxyl; nitro; azido; amino; alkanoyl (such as a $C_1$-$C_6$ alkanoyl group such as acyl or the like); carboxamido; alkyl groups (including cycloalkyl groups, having 1 to about 8 carbon atoms, for example 1, 2, 3, 4, 5, or 6 carbon atoms); alkenyl and alkynyl groups (including groups having one or more unsaturated linkages and from 2 to about 8, such as 2, 3, 4, 5 or 6, carbon atoms); alkoxy groups having one or more oxygen linkages and from 1 to about 8, for example 1, 2, 3, 4, 5 or 6 carbon atoms; aryloxy such as phenoxy; alkylthio groups including those having one or more thioether linkages and from 1 to about 8 carbon atoms, for example 1, 2, 3, 4, 5 or 6 carbon atoms; alkylsulfinyl groups including those having one or more sulfinyl linkages and from 1 to about 8 carbon atoms, such as 1, 2, 3, 4, 5, or 6 carbon atoms; alkylsulfonyl groups including those having one or more sulfonyl linkages and from 1 to about 8 carbon atoms, such as 1, 2, 3, 4, 5, or 6 carbon atoms; aminoalkyl groups including groups having one or more N atoms and from 1 to about 8, for example 1, 2, 3, 4, 5 or 6, carbon atoms; carbocyclic aryl having 4, 5, 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, (e.g. benzyl); arylalkoxy having 1 to 3 separate or fused rings and from 6 to about 18 ring carbon atoms (e.g. O-benzyl); or a saturated, unsaturated, or aromatic heterocyclic group having 1 to 3 separate or fused rings with 3 to about 8 members per ring and one or more N, O or S atoms, (e.g. coumarinyl, quinolinyl, isoquinolinyl, quinazolinyl, pyridyl, pyrazinyl, pyrimidyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl). Such heterocyclic groups may be further substituted, e.g. with hydroxy, alkyl, alkoxy, halogen and amino.

As used herein, where an internal substituent is flanked by bonds (for example —NRC(O)—) the order of the atoms is fixed, the orientation of the group may not be reversed, and is inserted into a structure in the orientation presented. In other words —NRC(O)— is not the same as —C(O)NR—. As used herein the term C(O) (for example —NRC(O)—) is used to indicate a carbonyl (C=O) group, where the oxygen is bonded to the carbon by a double bond.

A substituent bearing a broken bond, such as the example shown below, means that the substituent is directly bonded to the molecule at the indicated position. No additional methylene ($CH_2$) groups are implied.

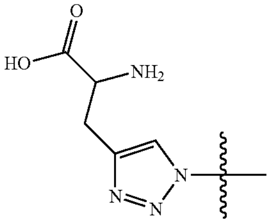 [SMILES: *n1cc(CC(N)C(=O)O)nn1]

Substituents bearing two broken bonds, such as the example shown below, means that the orientation of the atoms is as-indicated, left to right and should be inserted into a molecule in the orientation shown. No additional methylene ($CH_2$) groups are implied unless specifically indicated.

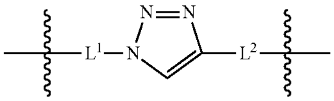

Embodiments

As described herein, all embodiments or subcombinations may be used in combination with all other embodiments or subcombinations, unless mutually exclusive.

In some of the following embodiments, Z is $CO_2Q$. In some of the following embodiments, Q is H. In some of the following embodiments, m is 4, 5, or 6. In some of the following embodiments, m is 6. In some of the following embodiments, n is 2, 3, or 4. In some of the following embodiments, n is 3. In some of the following embodiments, a is 3 or 4. In some of the following embodiments, a is 4. In some of the following embodiments, Y is —C(O)—. In some of the following embodiments, W is —NHC(O)—.

Embodiments of the invention include compounds having the structure

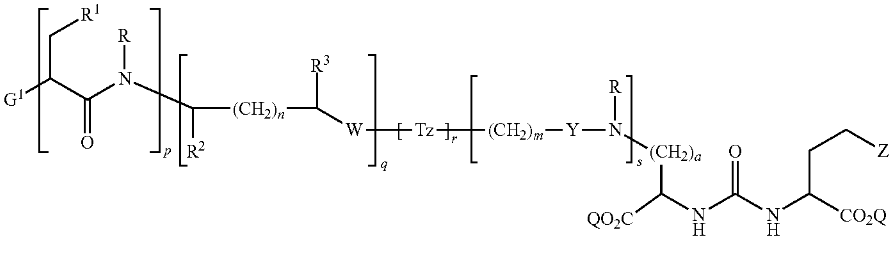

wherein the subunits associated with elements p, q, r, and s may be in any order. Z is tetrazole or $CO_2Q$; each Q is independently selected from hydrogen or a protecting group, a is 1, 2, 3, or 4, and R is each independently H or $C_1$-$C_4$ alkyl.

Variable r is 0 or 1. Tz is a triazole group selected from the group consisting of

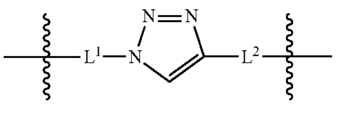

and

-continued

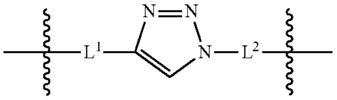

where $L^1$ is

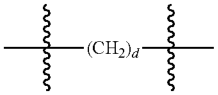

or

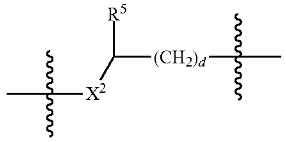

, $L^2$ is

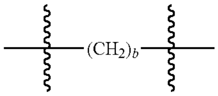

or

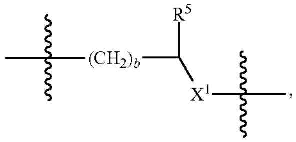

, $X^1$ is —NRC(O)—, —NRC(O)NR—, —NRC(S)NR—, or —NRC(O)O—; $X^2$ is —C(O)NR—, —NRC(O)NR—, —NRC(S)NR—, or —OC(O)NR—; $R^5$ is H, $CO_2H$, or $CO_2R^6$, where $R^6$ is a $C_1$-$C_6$ alkyl, $C_2$-$C_{12}$ aryl, or $C_4$-$C_{16}$ alkylaryl; b is 1, 2, 3, or 4; and d is 1, 2, 3, or 4.

Variable q is 0 or 1. W is —NRC(O)—, —NRC(O)NR—, NRC(S)NR—, —NRC(O)O—, —OC(O)NR—, —OC(O)—, —C(O)NR—, or —C(O)O—; $R^2$ and $R^3$ are independently H, $CO_2H$, or $CO_2R^4$, where $R^4$ is a $C_1$-$C_6$ alkyl, $C_2$-$C_{12}$ aryl, or $C_4$-$C_{16}$ alkylaryl, wherein if one of $R^2$ and $R^3$ is $CO_2H$ or $CO_2R^4$, then the other is H; n is 1, 2, 3, 4, 5 or 6.

Variable s is 0 or 1. Y is —C(O)—, —NRC(O)—, —NRC(S)—, —OC(O)—; and m is 1, 2, 3, 4, 5, or 6.

Variable p is 0, 1, 2, or 3, and when p is 2 or 3, each $R^1$ may be the same or different. $R^1$ is H, $C_1$-$C_6$ alkyl, $C_2$-$C_{12}$ aryl, or $C_4$-$C_{16}$ alkylaryl.

G is a moiety selected from the group consisting of

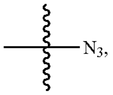

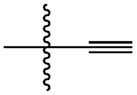

,

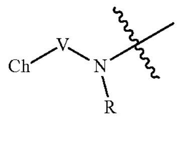

,

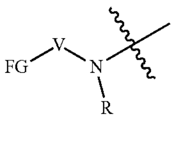

,

-continued

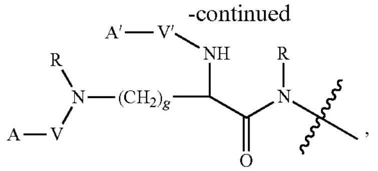

and

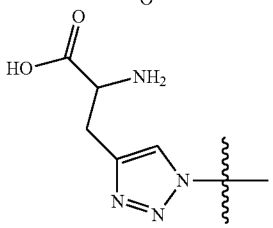

where Ch is a metal chelating moiety, optionally including a chelated metal; FG is a fluorescent dye moiety which emits in the visible or near infrared spectrum; one of A and A' is Ch and the other is FG; V and V' are independently —C(O)—, —NRC(O)—, —NRC(S)—, or —OC(O)—; and g is 1, 2, 3, 4, 5, or 6. The following conditions also apply:

1) when G is

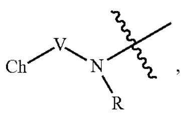

, or

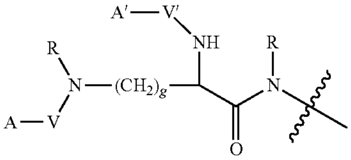

and r is 0, then q and s are both 1;

2) when G is

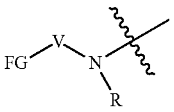

and r is 0, then q and s are both 0 or both 1;

3) when G is

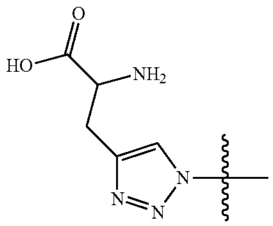 [SMILES: *n1cc(CC(N)C(=O)O)nn1]

then p is 0 and $R^2$ is H, and the structure optionally includes a chelated metal ion:

4) when G is

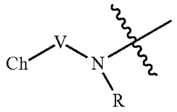

and r is 0, then if p is 0, then one of $R^2$ and $R^3$ is $CO_2R^4$, and the other is H; and 5) when g is

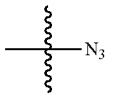

or

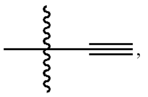

then r is 0.

In some embodiments, Z is $CO_2Q$. In some embodiments, Q is H. In some embodiments, m is 4, 5, or 6. In some embodiments, m is 6. In some embodiments, n is 2, 3, or 4. In some embodiments, n is 3. In some embodiments, a is 4. In some embodiments, subunits associated with elements p, q and s are in the order drawn and r may be in any location, including between one of p, q, or s. In some embodiments r is 0.

Embodiments include compounds having the structure

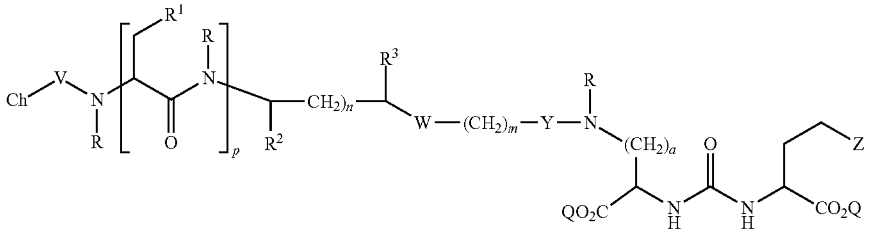

wherein Z is tetrazole or $CO_2Q$; each Q is independently selected from hydrogen or a protecting group, a is 1, 2, 3, or 4, and R is each independently H or $C_1$-$C_4$ alkyl. Ch is a metal chelating moiety optionally including a chelated metal. W is —NRC(O)—, —NRC(O)NR—, NRC(S)NR—, —NRC(O)O—, —OC(O)NR—, —OC(O)—, —C(O)NR—, or —C(O)O—. Y is —C(O)—, —NRC(O)—, —NRC(S)—, —OC(O). V is —C(O)—, —NRC(O)—, —NRC(S)—, or —OC(O)—. In exemplary embodiment m is 1, 2, 3, 4, 5, or 6; n is 1, 2, 3, 4, 5 or 6; and p is 0, 1, 2, or 3, and when p is 2 or 3, each $R^1$ may be the same or different. $R^1$ is H, $C_1$-$C_6$ alkyl, $C_2$-$C_{12}$ aryl, or $C_4$-$C_{16}$ alkylaryl. $R^2$ and $R^3$ are independently H, $CO_2H$, or $CO_2R^4$, where $R^4$ is a $C_1$-$C_6$ alkyl, $C_2$-$C_{12}$ aryl, or $C_4$-$C_{16}$ alkylaryl, wherein when one of $R^2$ and $R^3$ is $CO_2H$ or $CO_2R^4$, the other is H, and when p is 0, one of $R^2$ and $R^3$ is $CO_2R^4$, and the other is H.

In some embodiments, the compound has the structure shown below.

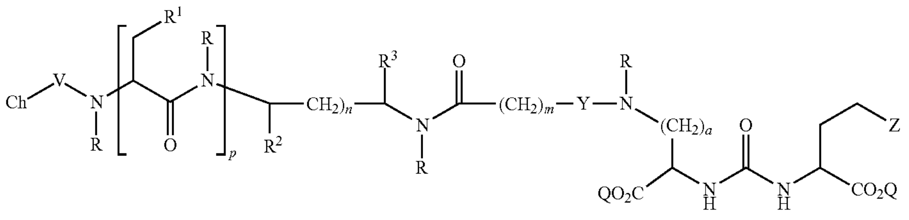

In some embodiments, the compound has the structure shown below.

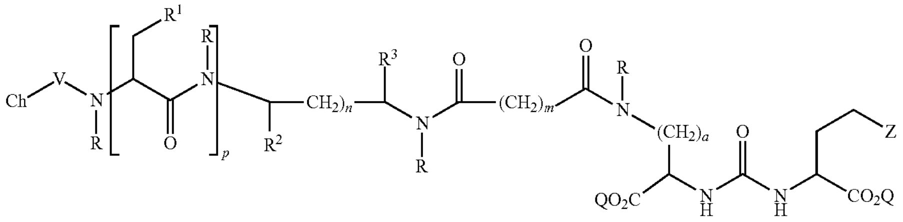

In some embodiments, p is 1, 2 or 3. When p is 2 or 3, each $R^1$ may be the same or different. When two $R^1$ groups are different, the two may be in any order. In some embodiments, p is 2. In some embodiments, p is 2, and both $R^1$ are the same. In some embodiments, $R^1$ is $C_2$-$C_{12}$ aryl. In some embodiments $R^1$ is phenyl. In some embodiments, $R^3$ is $CO_2H$ and $R^2$ is H. In some embodiments, $R^2$ is $CO_2H$ and $R^3$ is H. In some embodiments, $R^2$ and $R^3$ are both H.

In some embodiments, p is 0. In some embodiments where p is 0, $R^2$ is $CO_2R^4$, and $R^3$ is H. In some embodiments where p is 0, $R^3$ is $CO_2R^4$, and $R^2$ is H. In some embodiments $R^4$ is $C_2$-$C_{12}$ aryl, or $C_4$-$C_{16}$ alkylaryl. In some embodiments $R^4$ is benzyl.

Ch is a metal chelating moiety optionally including a chelated metal. A metal chelating moiety is a chemical moiety that non-covalently binds a metal atom, usually with a plurality of non-covalent interactions. Ch includes any additional atoms or linkers necessary to attach the metal chelating moiety to the rest of the compound. For instance linking groups having alkyl, aryl, combination of alkyl and aryl, or alkyl and aryl groups having heteroatoms may be present in the chelating moiety. Numerous metal chelating moieties are known in the art. Any acceptable chelator can be used with the present invention as long as compatible and capable of chelating a desired metal. Examples of metal chelating moieties (Ch) include, but are not limited to 1,4,7,10-tetraazacyclododecane-1,4,7,10-tetraacetic acid (DOTA) and Diethylene-triaminepentaacetic acid (DTPA). In some embodiments, Ch has a structure shown below.

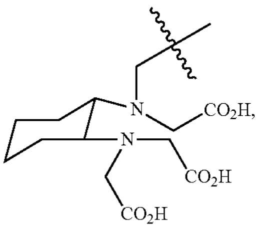

-continued

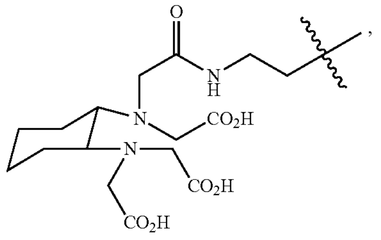

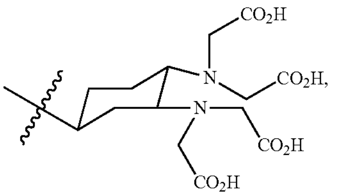

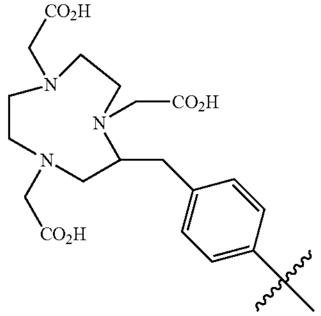

,

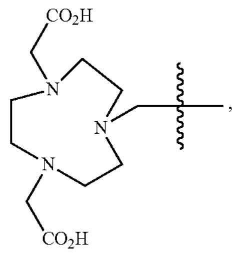

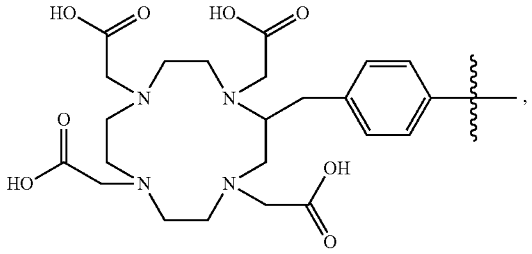

-continued
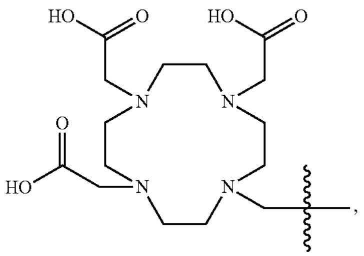
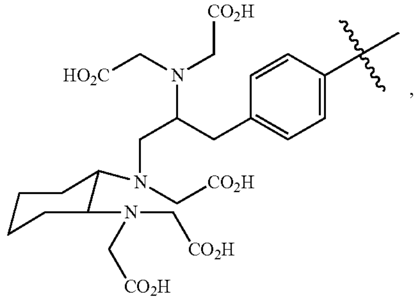
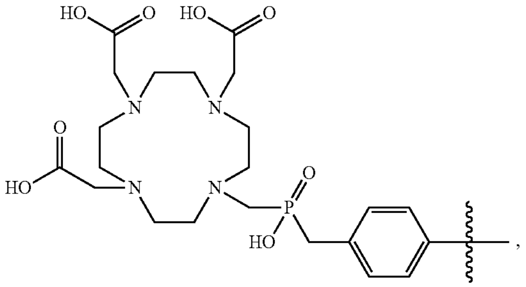
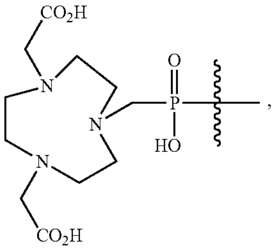
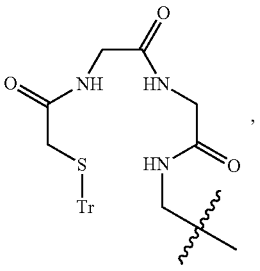
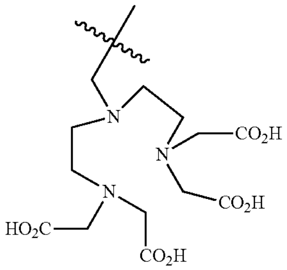
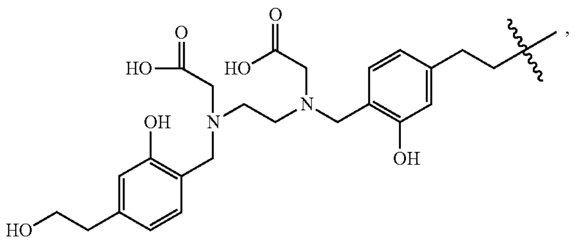
-continued
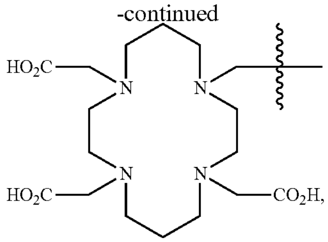
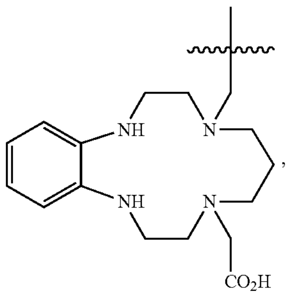
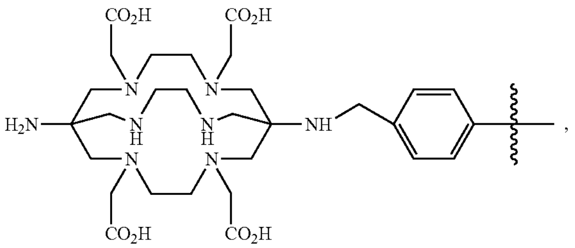
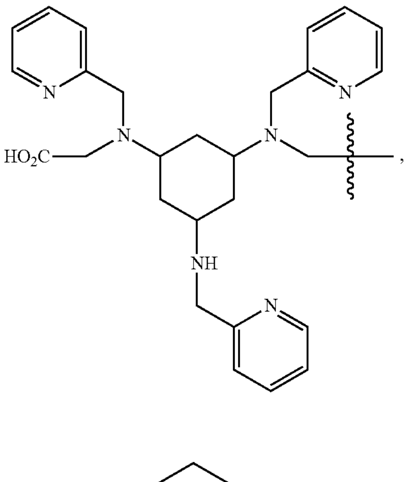
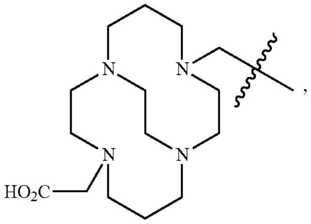

-continued
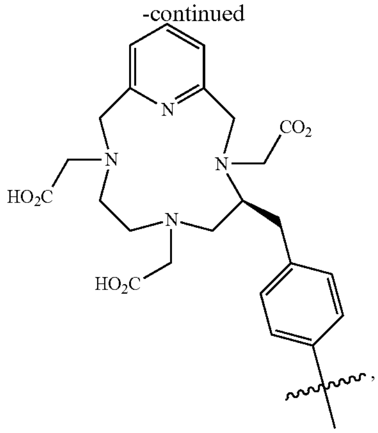
-continued
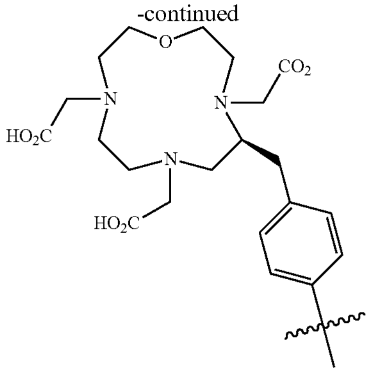
Examples of specific compounds include the compounds shown below.
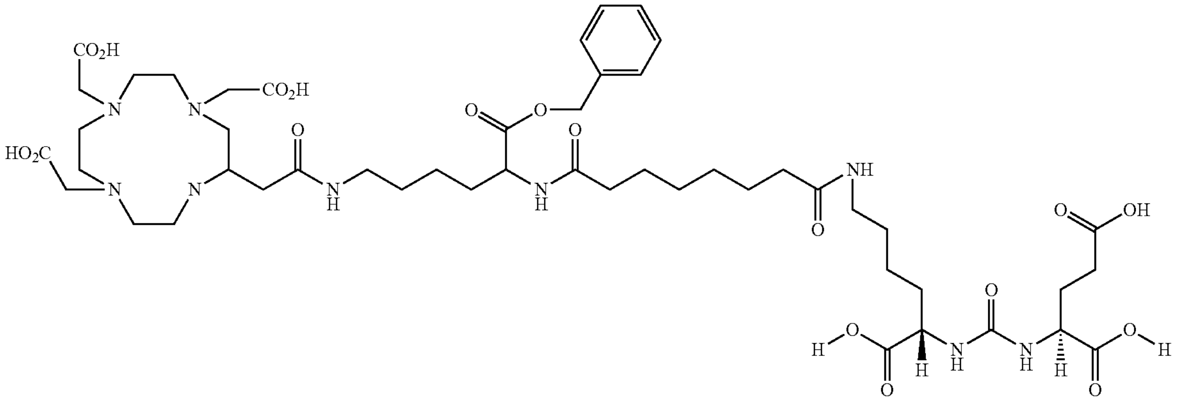
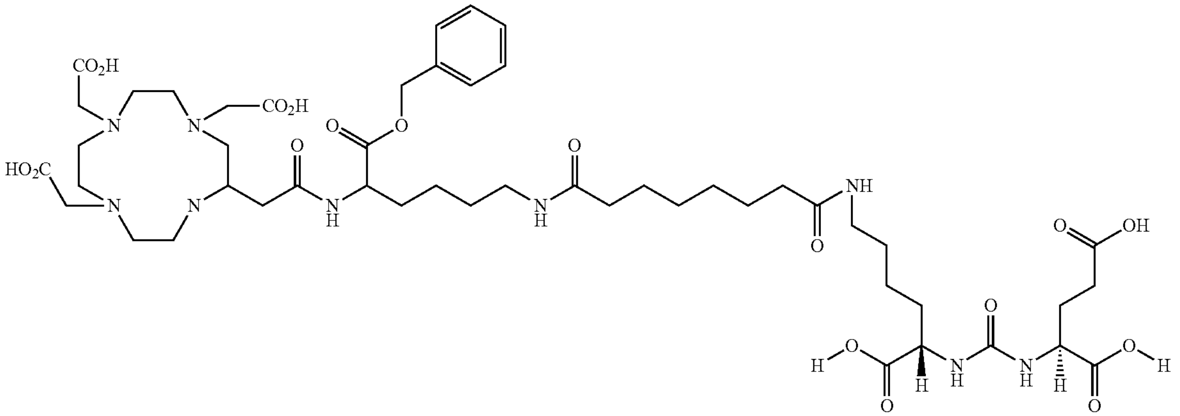
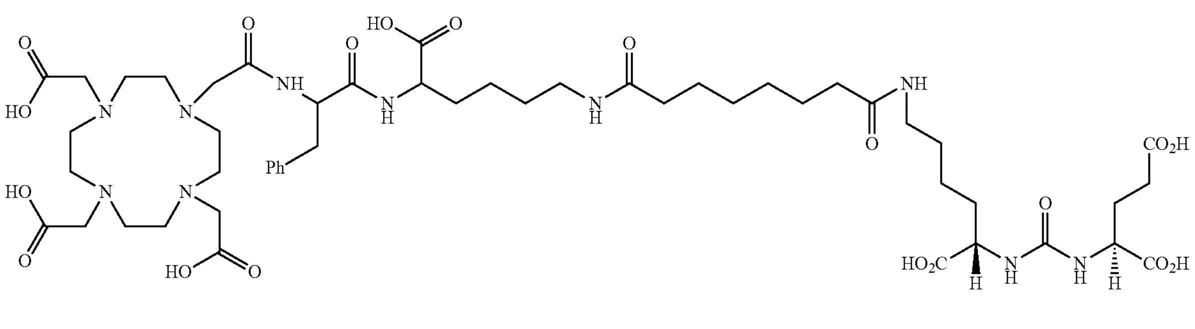

-continued
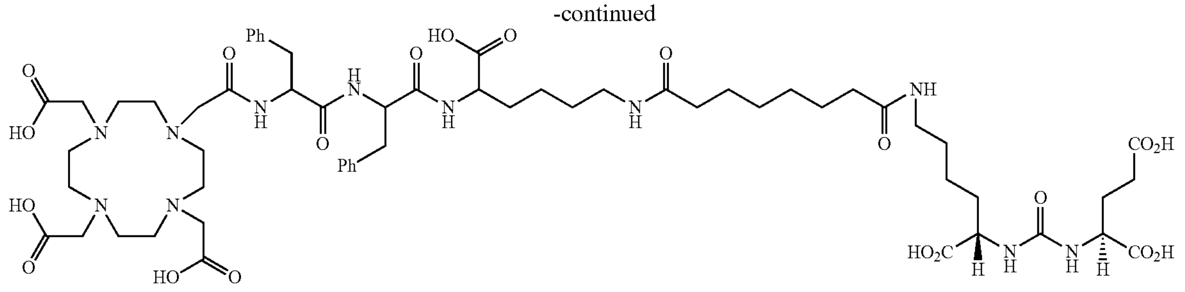
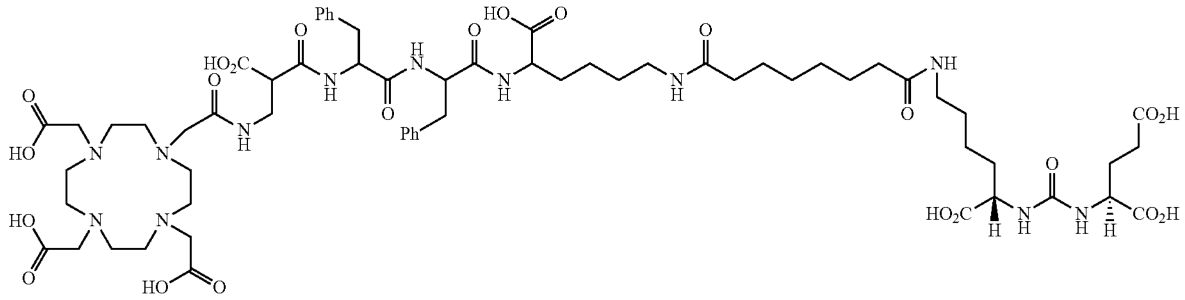
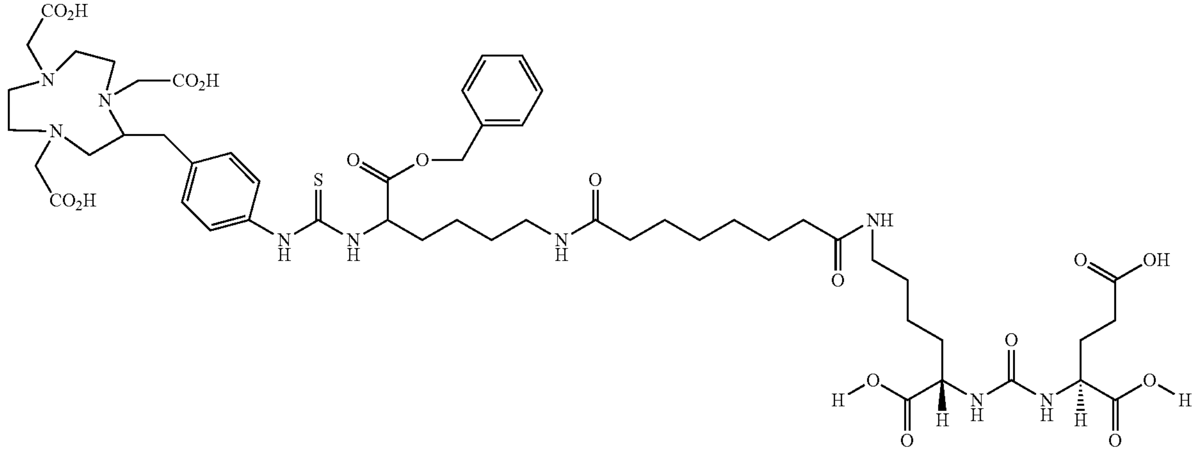
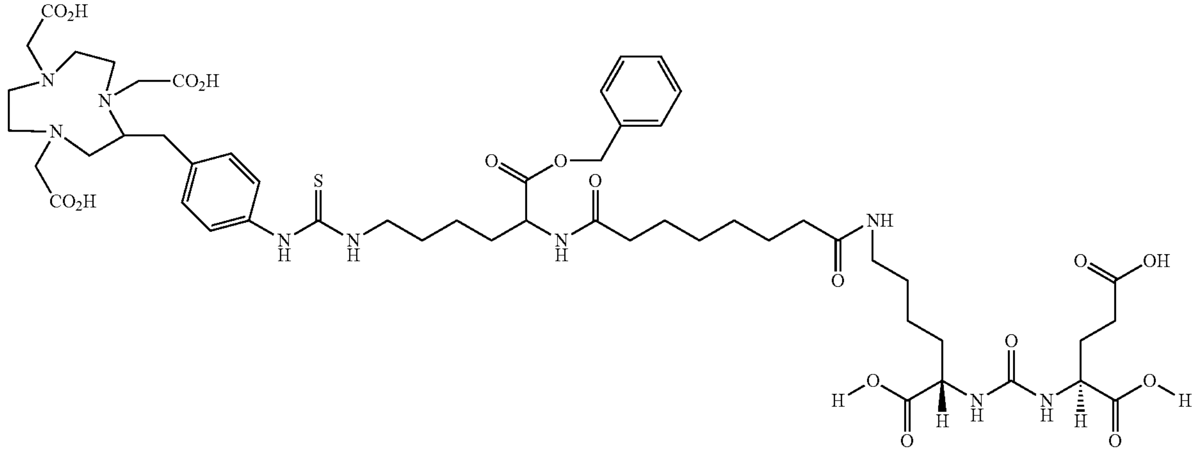

-continued
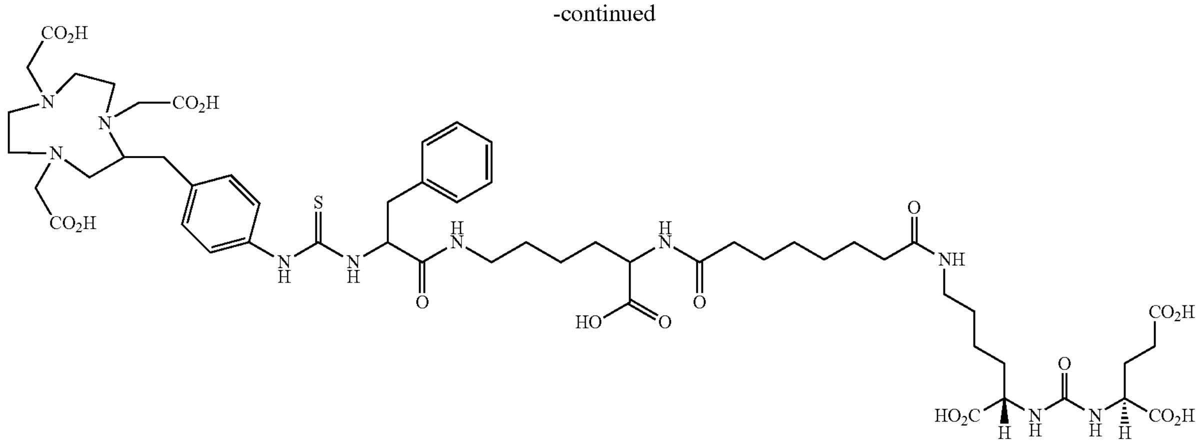
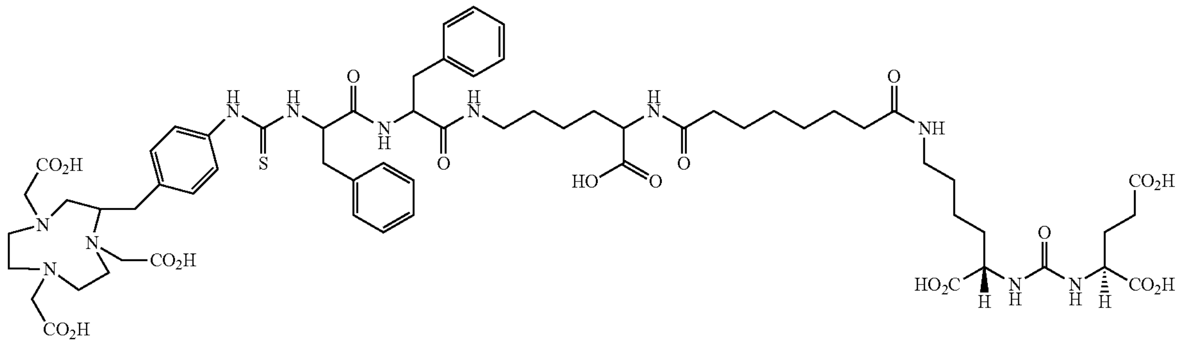
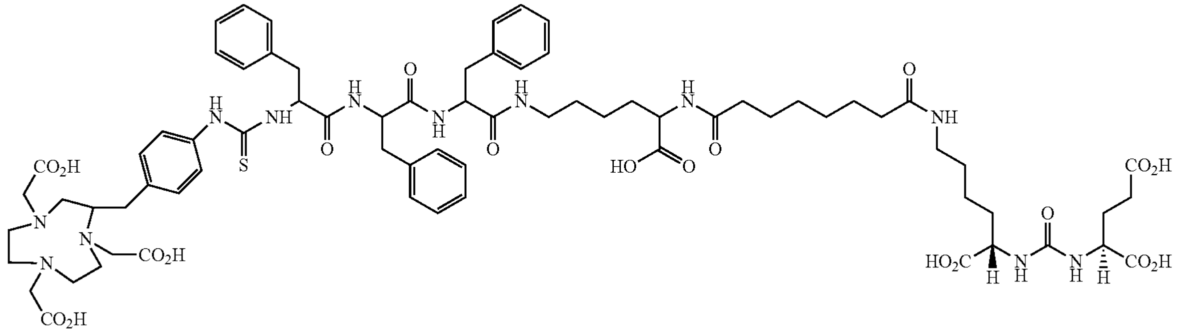
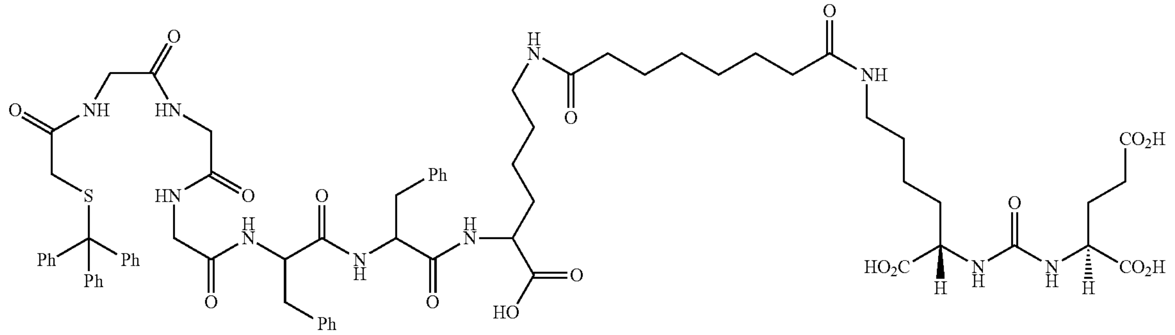

-continued

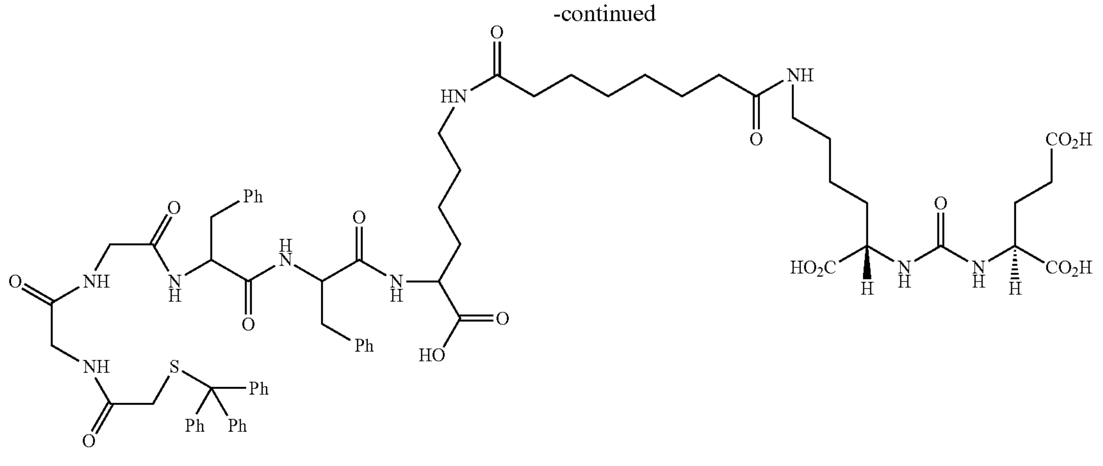

In some embodiments, the compound further includes a chelated metal. In some embodiments, the chelated metal is Tc, In, Ga, Y, Lu, Re, Cu, Ac, Bi, Pb, Sm, Sc, Co, Ho, Gd, Eu, Tb, or Dy. In some embodiments, the chelated metal is Tc, Ga, In, Cu, Y, Ac, Lu, Re, or Bi. In some embodiments the metal is an isotope, for example a radioactive isotope. In some embodiments, the isotope is Tc-99m, In-111, Ga-67, Ga-68, Y-86, Y-90, Lu-177, Re-186, Re-188, Cu-64, Cu-67, Co-55, Co-57, Sc-47, Ac-225, Bi-213, Bi-212, Pb-212, Sm-153, Ho-166, or Dy-166. In some embodiments, the isotope is Tc-99m, In-111, Ga-67, Ga-68, Y-90, Lu-177, Re-186, Re-188, Cu-67, Ac-225, Bi-213, or Bi-212.

Embodiments include compounds having the structure

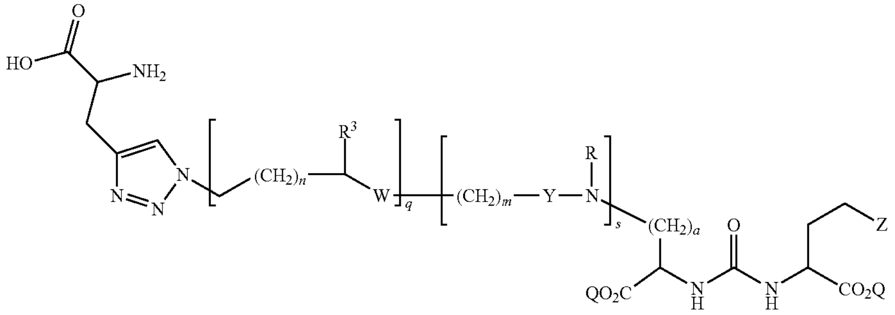

optionally including a chelated metal ion. Z is tetrazole or $CO_2Q$; each Q is independently selected from hydrogen or a protecting group, and a is 1, 2, 3, or 4. R is each independently H or $C_1$-$C_4$ alkyl. W is —NRC(O)—, —NRC(O)NR—, NRC(S)NR—, —NRC(O)O—, —OC(O)NR—, —OC(O)—, —C(O)NR—, or —C(O)O—. Y is —C(O)—, —NRC(O)—, —NRC(S)—, —OC(O)—. In some embodiments, subunits associated with q and s may be in the order shown or the reverse thereof.

In exemplary embodiment m is 1, 2, 3, 4, 5, or 6; n is 1, 2, 3, 4, 5 or 6; q is 0 or 1; and s is 0 or 1. $R^3$ is H, $CO_2H$, or $CO_2R^4$, where $R^4$ is a $C_1$-$C_6$ alkyl, $C_2$-$C_{12}$ aryl, or $C_4$-$C_{16}$ alkylaryl. Some embodiments further include a chelated metal ion. In some embodiments, the metal ion is Tc, Re, Ga, or Cu. In some embodiments, the metal ion is Tc-99m, Re-186, Re-188, Cu-64, or Ga-68. In some embodiments, the metal ion is Tc-99m, Re-186 or Re-188.

In some embodiments, the compound has the structure

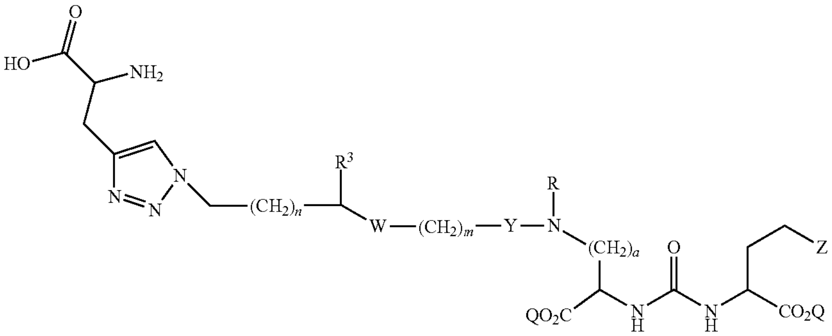

optionally including a chelated metal ion. Z is tetrazole or $CO_2Q$; each Q is independently selected from hydrogen or a protecting group and a is 1, 2, 3, or 4. R is each independently H or $C_1$-$C_4$ alkyl. W is —NRC(O)—, —NRC(O)NR—, NRC(S)NR—, —NRC(O)O—, —OC(O)NR—, —OC(O)—, —C(O)NR—, or —C(O)O—. Y is —C(O)—, —NRC(O)—, —NRC(S)—, —OC(O)—. In exemplary embodiments m is 1, 2, 3, 4, 5, or 6; and n is 1, 2, 3, 4, 5 or 6. $R^3$ is H, $CO_2H$, or $CO_2R^4$, where $R^4$ is a $C_1$-$C_6$ alkyl, $C_2$-$C_{12}$ aryl, or $C_4$-$C_{16}$ alkylaryl.

In some embodiments, the compound has the structure

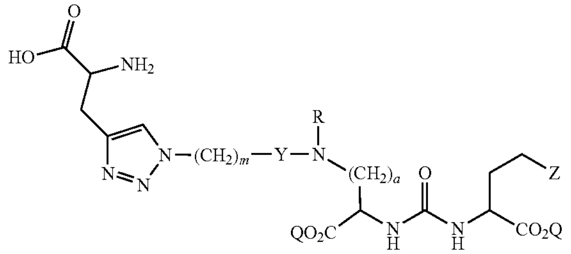

where a is 1, 2, 3, or 4. Y is —C(O)—, —NRC(O)—, —NRC(S)—, —OC(O)—, and In exemplary embodiment m is 1, 2, 3, 4, 5, or 6.

In some embodiments, the compound has the structure

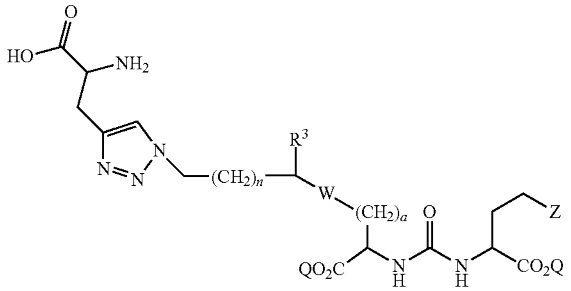

where a is 1, 2, 3, or 4. W is —NRC(O)—, —NRC(O)NR—, NRC(S)NR—, —NRC(O)O—, —OC(O)NR—, —OC(O)—, —C(O)NR—, or —C(O)O—, and n is 1, 2, 3, 4, 5 or 6. $R^3$ is H, $CO_2H$, or $CO_2R^4$, where $R^4$ is a $C_1$-$C_6$ alkyl, $C_2$-$C_{12}$ aryl, or $C_4$-$C_{16}$ alkylaryl.

In some embodiments, the compound has the structure

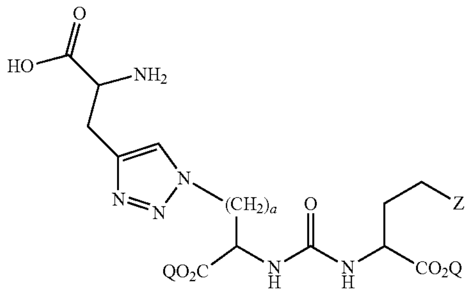

where a is 1, 2, 3, or 4.

In some embodiments, Y is —C(O)—.

In some embodiments, W is —NHC(O)—.

In some embodiments, m is 4, 5, or 6. In some embodiments, m is 6.

In some embodiments, n is 2, 3, or 4. In some embodiments, n is 3.

In some embodiments, $R^3$ is $CO_2H$. In some embodiments, $R^3$ is H. In some embodiments, $R^3$ is $CO_2R^4$.

Examples of compounds include those having the structure shown below

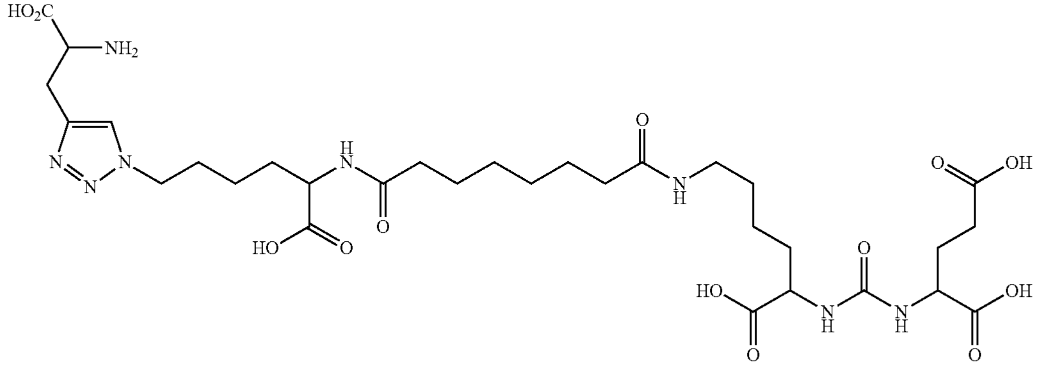 [SMILES: NC(Cc1cn(CCCCC(NC(=O)CCCCCCC(=O)NCCCCC(NC(=O)NC(CCC(=O)O)C(=O)O)C(=O)O)C(=O)O)nn1)C(=O)O]

In some embodiments, the compound further includes a chelated metal ion. In some embodiments, the metal ion is Tc, Re, Cu, or Ga. In some embodiments, the metal ion is Tc-99m, Re-186, Re-188, Cu-64, or Ga-68. In some embodiments, the metal ion is Tc-99m.

The metal ion chelates to the triazole amino acid portion of the molecule to form a structure shown below using Tc as an example.

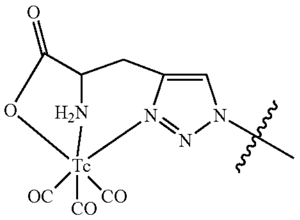

Embodiments include compounds having the structure

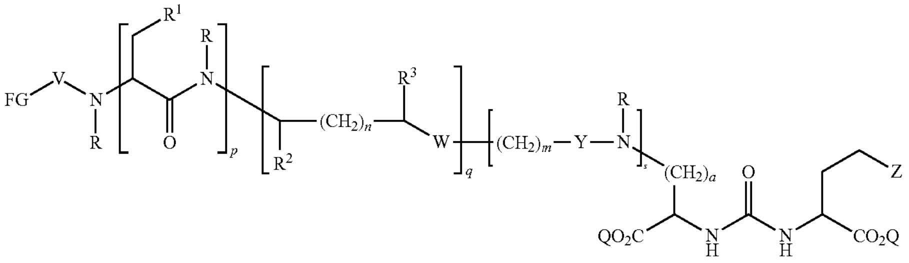

where p, q, and s are in the order drawn, and q and s are either both 0 or both 1. Z is tetrazole or $CO_2Q$; each Q is independently selected from hydrogen or a protecting group, and a is 1, 2, 3, or 4. FG is a fluorescent dye moiety which emits in the visible or near infrared spectrum. R is each independently H or $C_1$-$C_4$ alkyl. V is —C(O)— or —NRC(O)— or —NRC(S)—. W is —NRC(O)—, —NRC(O)NR—, NRC(S)NR—, —NRC(O)O—, —OC(O)NR—, —OC(O)—, —C(O)NR—, or —C(O)O—. Y is —C(O)—, —NRC(O)—, —NRC(S)—, —OC(O). In exemplary embodiments m is 1, 2, 3, 4, 5, or 6; n is 1, 2, 3, 4, 5 or 6; p is 0, 1, 2, or 3, and when p is 2 or 3, each R' may be the same or different. $R^1$ is H, $C_1$-$C_6$ alkyl, $C_2$-$C_{12}$ aryl, or $C_4$-$C_{16}$ alkylaryl. $R^2$ and $R^3$ are independently H, $CO_2H$, or $CO_2R^4$, where $R^4$ is a $C_1$-$C_6$ alkyl, $C_2$-$C_{12}$ aryl, or $C_4$-$C_{16}$ alkylaryl, wherein when one of $R^2$ and $R^3$ is $CO_2H$ or $CO_2R^4$, the other is H. In some embodiments, the fluorescent dye moiety emits in the near infrared spectrum.

Some embodiments have the structure shown below.

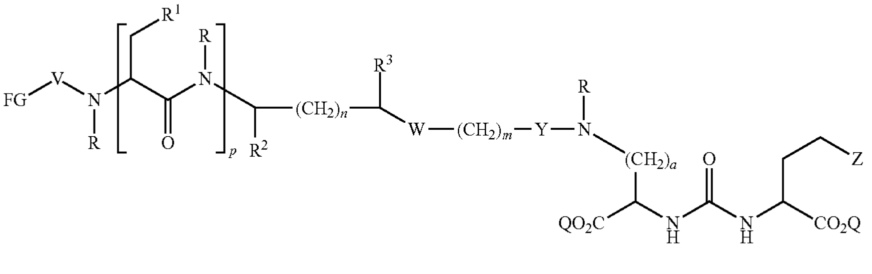

wherein Z is tetrazole or $CO_2Q$; each Q is independently selected from hydrogen or a protecting group, and a is 1, 2, 3, or 4. FG is a fluorescent dye moiety which emits in the visible or near infrared spectrum. R is each independently H or $C_1$-$C_4$ alkyl. V is —C(O)— or —NRC(O)— or —NRC(S)—. W is —NRC(O)—, —NRC(O)NR—, NRC(S)NR—, —NRC(O)O—, —OC(O)NR—, —OC(O)—, —C(O)NR—, or —C(O)O—. Y is —C(O)—, —NRC(O)—, —NRC(S)—, —OC(O)—. In exemplary embodiments m is 1, 2, 3, 4, 5, or 6; n is 1, 2, 3, 4, 5 or 6; p is 0, 1, 2, or 3, and when p is 2 or 3, each $R^1$ may be the same or different. $R^1$ is H, $C_1$-$C_6$ alkyl, $C_2$-$C_{12}$ aryl, or $C_4$-$C_{16}$ alkylaryl. $R^2$ and $R^3$ are independently H, CO2H, or $CO_2R^4$, where $R^4$ is a $C_1$-$C_6$ alkyl, $C_2$-$C_{12}$ aryl, or $C_4$-$C_{16}$ alkylaryl, wherein when one of $R^2$ and $R^3$ is $CO_2H$ or $CO_2R^4$, the other is H. In some embodiments, the fluorescent dye moiety emits in the near infrared spectrum.

In some embodiments, the compound has the structure shown below.

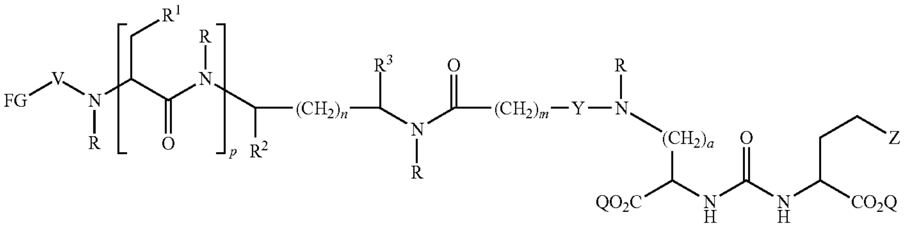

In some embodiments, the compound has the structure shown below.

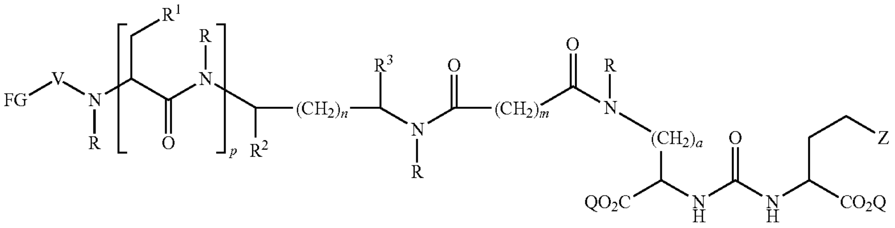

In some embodiments, the compound has the structure shown below.

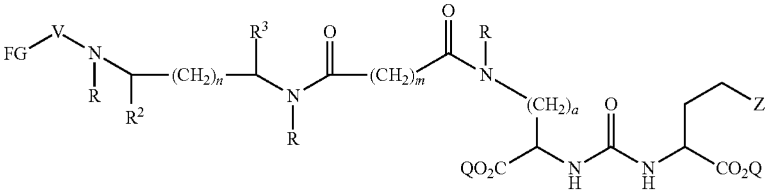

In some embodiments, the compound has the structure shown below.

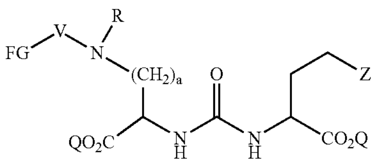

In some embodiments, p is 1, 2 or 3. In some embodiments, p is 2. In some embodiments $R^1$ is $C_2$-$C_{12}$ aryl. In some embodiments, $R^1$ is phenyl.

In some embodiments, p is 0.

In some embodiments, $R^3$ is $CO_2H$ and $R^2$ is H. In some embodiments, $R^2$ is $CO_2H$ and $R^3$ is H. In some embodiments, $R^2$ is $CO_2R^4$, and $R^3$ is H. In some embodiments, $R^3$ is $CO_2R^4$, and $R^2$ is H. In some embodiments $R^4$ is $C_2$-$C_{12}$ aryl, or $C_4$-$C_{16}$ alkylaryl. In some $R^4$ is benzyl. In some embodiments, $R^2$ is H, and $R^3$ is H.

In some embodiments V is —C(O)— or —NRC(S)—.

FG is a fluorescent dye moiety that emits light in the visible or near infrared spectrum. In some embodiments, FG is a fluorescent dye moiety which emits in the near infrared spectrum. FG includes any additional atoms or linkers necessary to attach the fluorescent dye moiety to the rest of the compound. For instance linking groups having alkyl, aryl, combination of alkyl and aryl, or alkyl and aryl groups having heteroatoms may be present in the chelating moiety, so long as the linker does not interfere with the fluorescence of the dye. In some embodiments, the fluorescent dye moiety includes a poly(ethyleneglycol) linker. Numerous fluorescent dye moieties are known in the art, and will be readily apparent to one of ordinary skill. Many fluorescent dyes are commercially available with activated groups used to react with protein sidechains or other compounds.

Examples of fluorescent compounds which may form all or part of the structure of FG include carbocyanine, indocarbocyanine, oxacarbocyanine, thiacarbocyanine, merocyanine, polymethine, coumarine, rhodamine, xanthene, fluorescein, and boron-dipyrromethane (BODIPY) compounds, to name a few.

Examples of fluorescent dye moieties include those described in WO 20089/109832, incorporated by reference herein in its entirety.

Specific dyes which emit in the near infrared spectrum include commercially available compounds Cy5, Cy5.5, and Cy7, available from GE Healthcare; VivoTag-680, VivoTag-5680, and VivoTag-5750, available from VisEn Medical;

AlexaFluor660, AlexaFluor680, AlexaFluor700, AlexaFluor750, and AlexaFluor790, available from Invitrogen; Dy677, Dy676, Dy682, Dy752, and Dy780, available from Dyonics; DyLight547, and Dylight647, available from Pierce; HiLyte Fluor 647, HiLyte Fluor 680, and HiLyte Fluor 750, available from AnaSpec; IRDye 800CW, IRDye 800RS, and IRDye 700DX, available from Li-Cor; and ADS780WS, ADS830WS, and ADS832WS, available from American Dye Source.

In some embodiments, FG is a structure shown below.

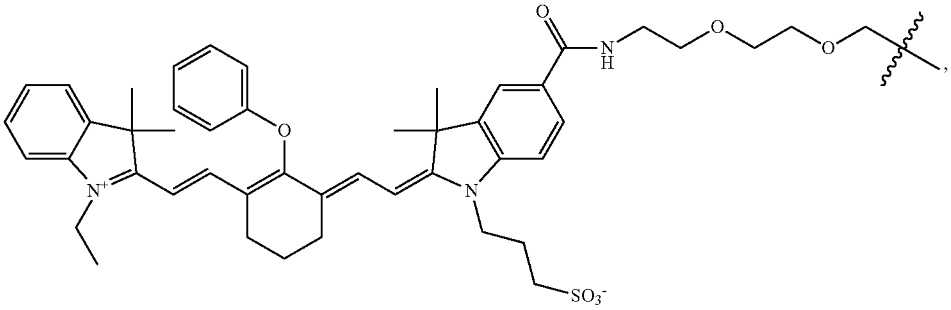
,

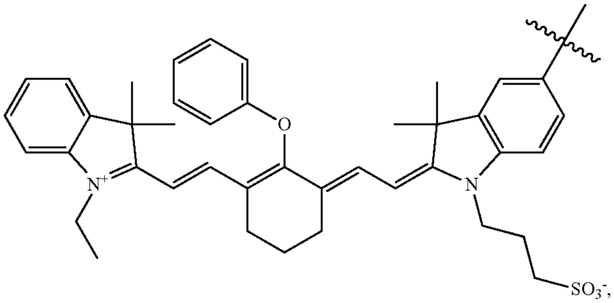
,

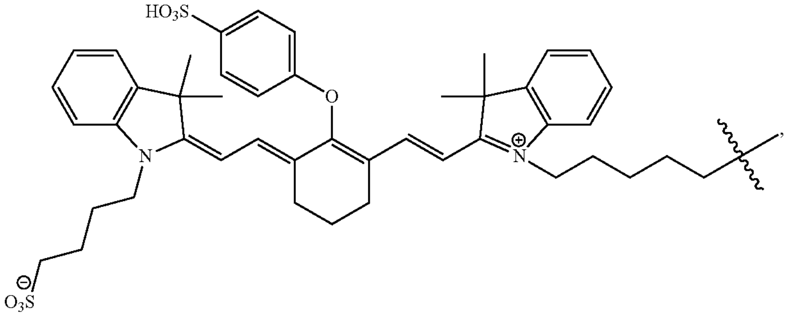
,

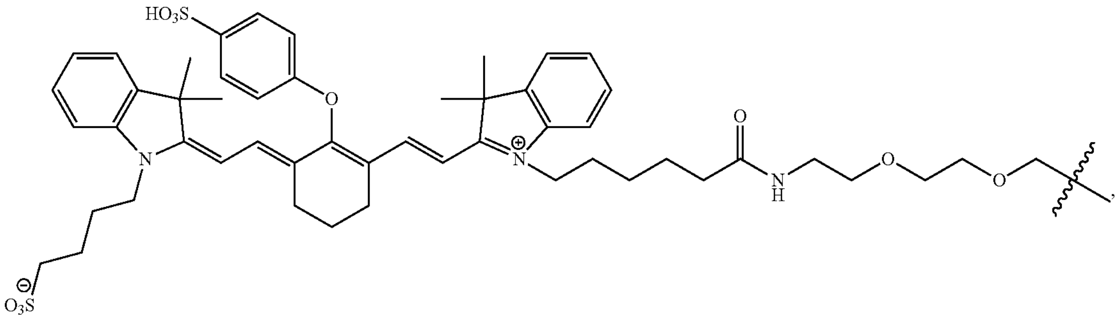
,

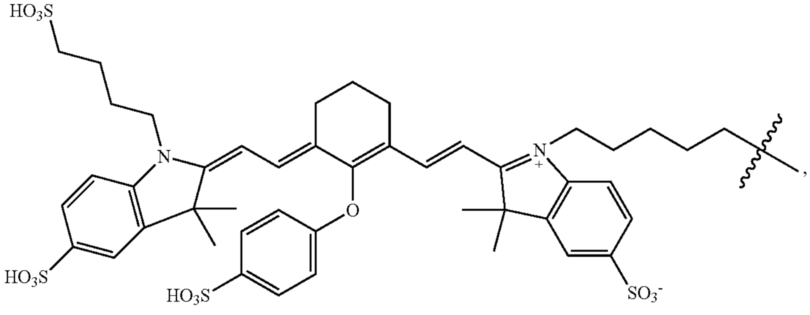
,

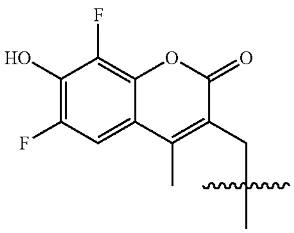
,

-continued
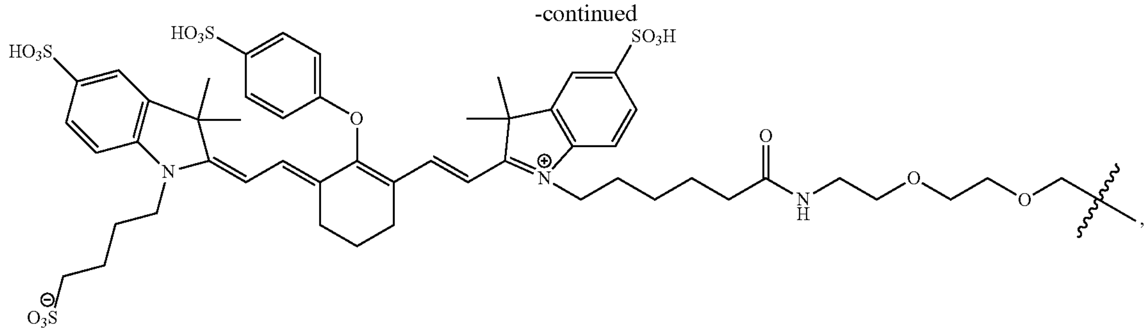
,
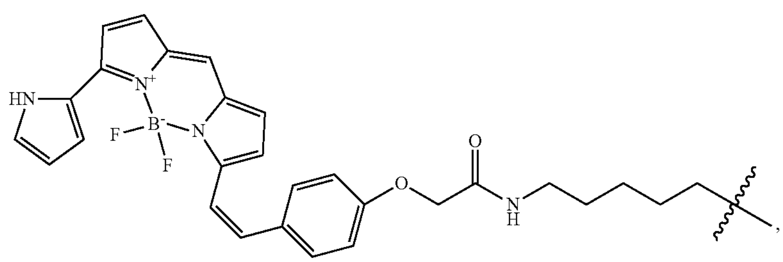
,
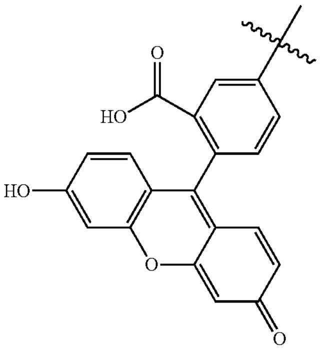
,
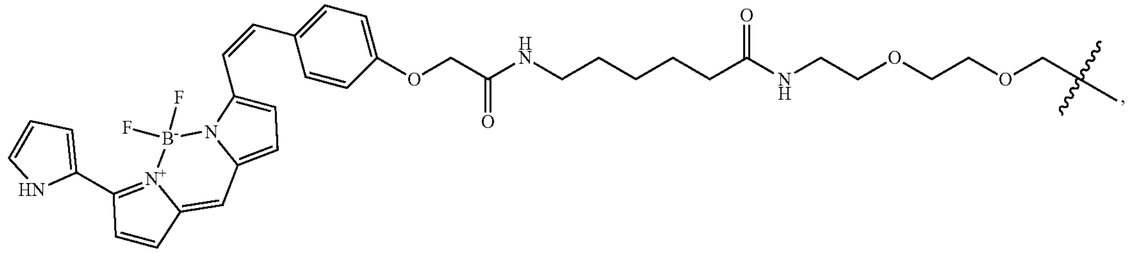
,
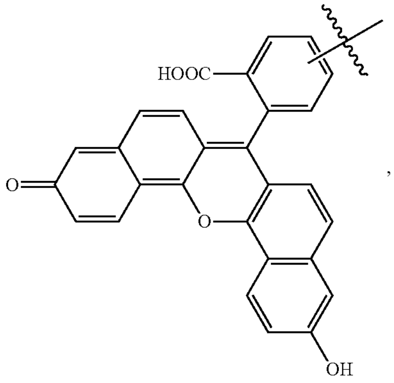
,
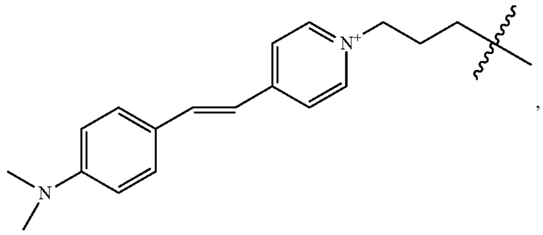
,
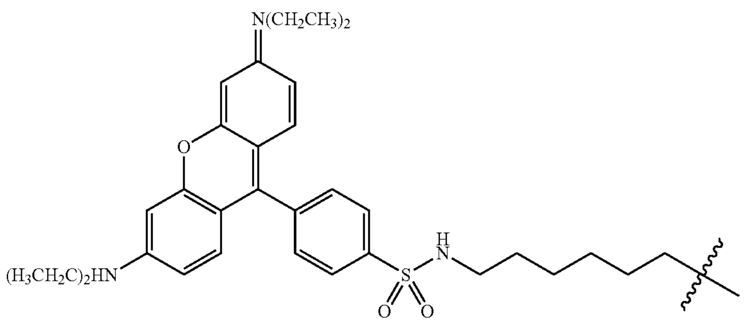

Exemplary compounds include those shown below.
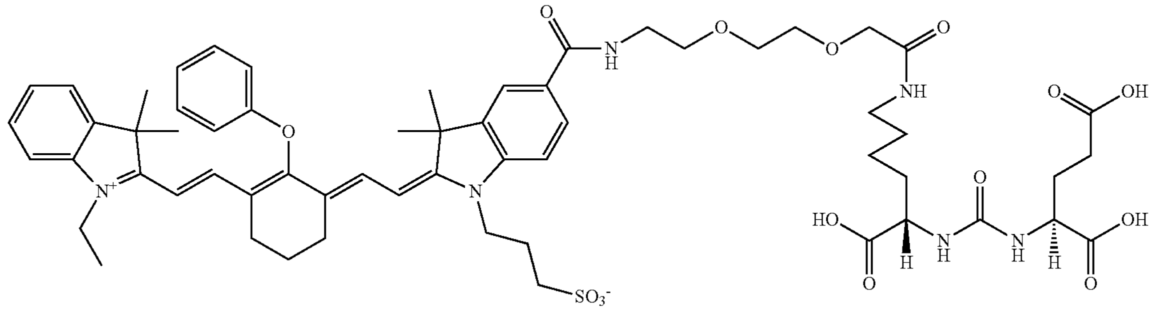
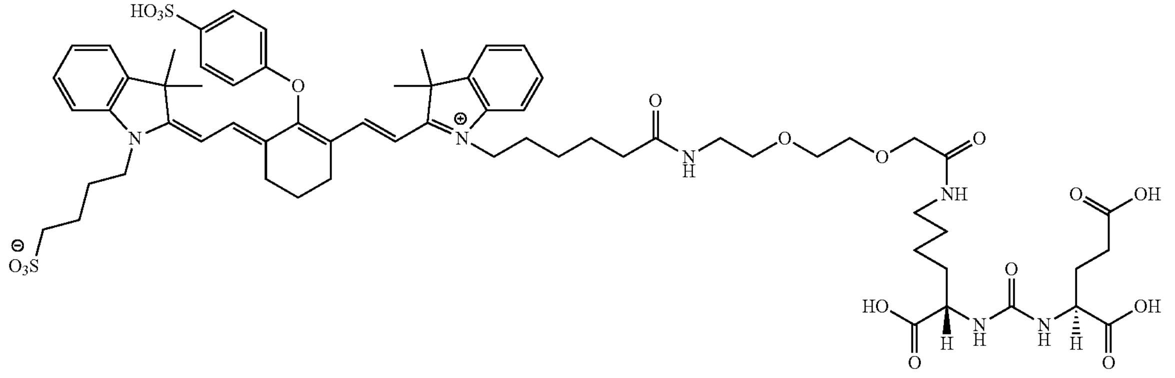
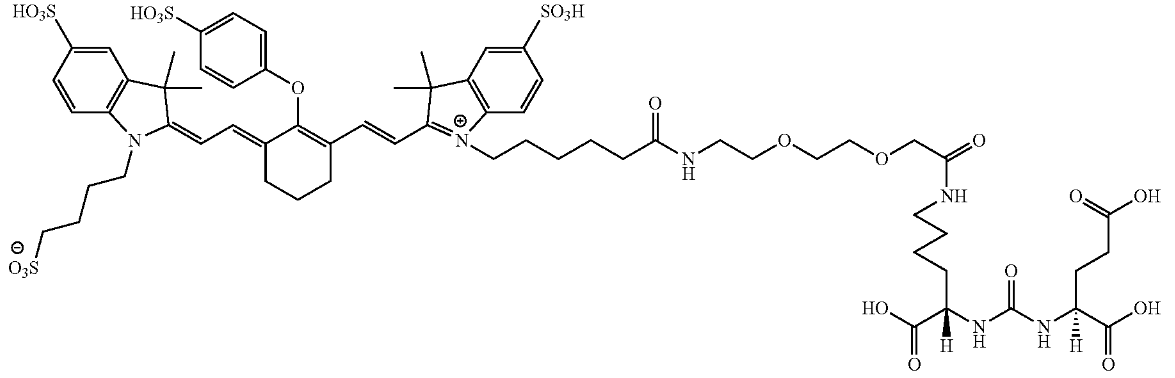
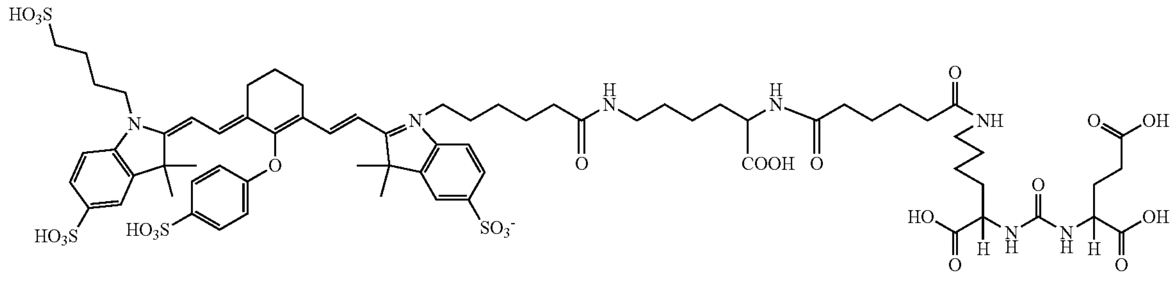
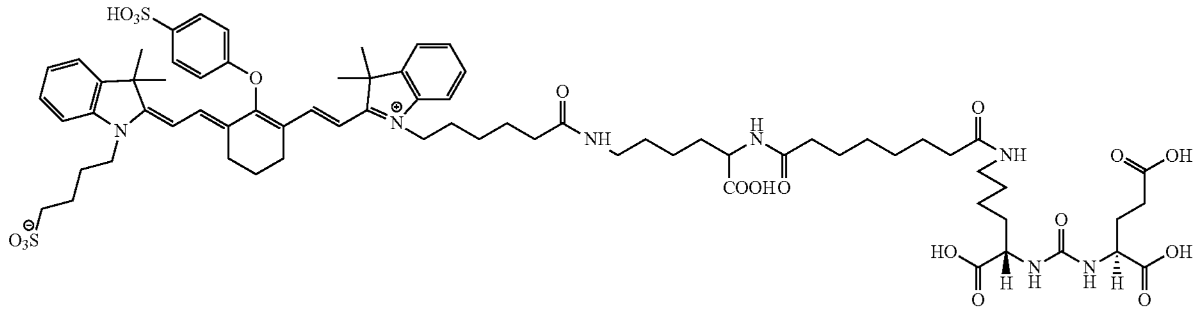

-continued
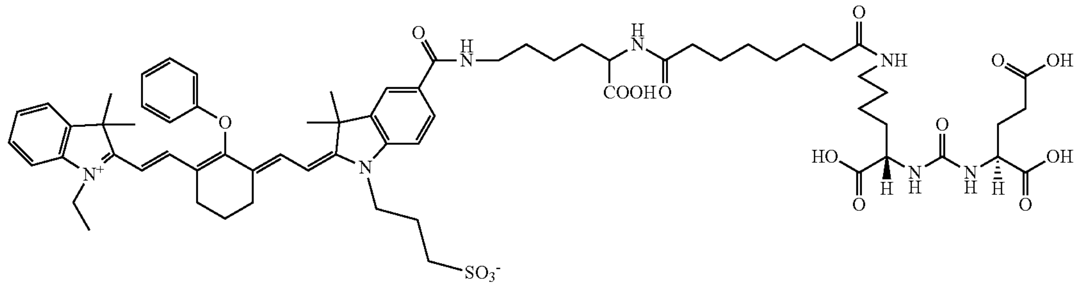
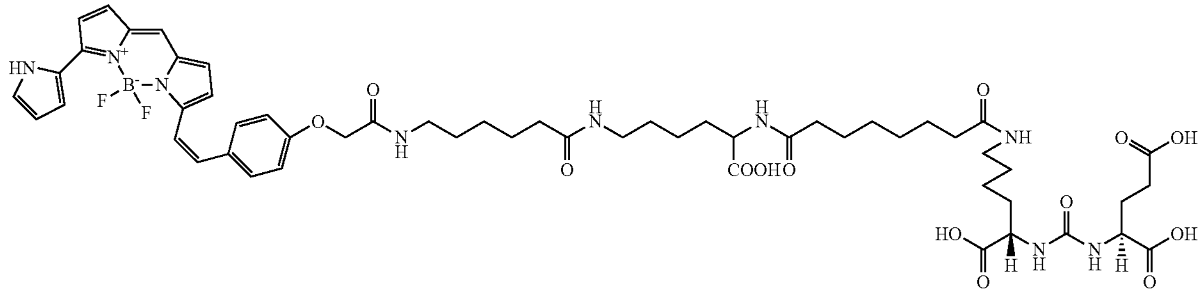
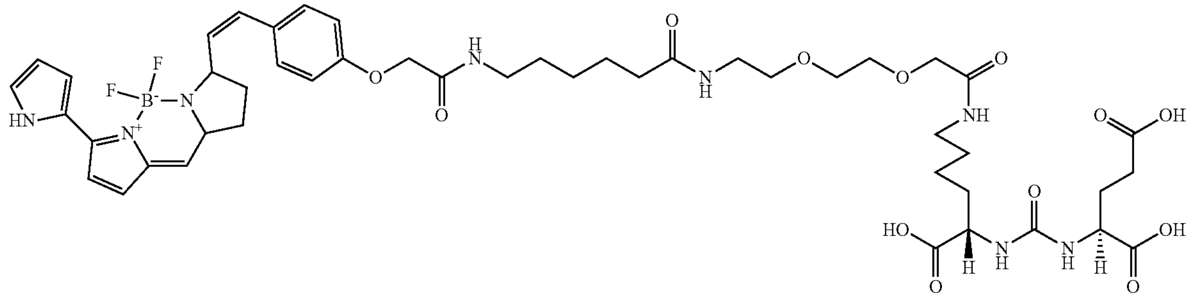
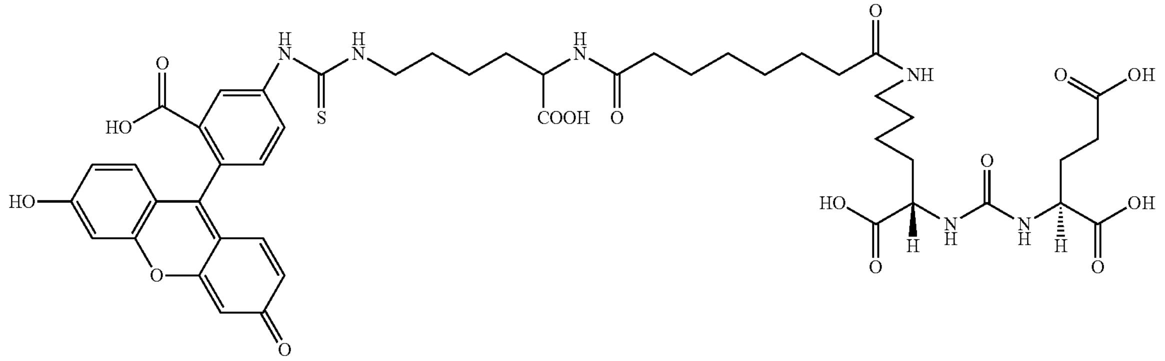
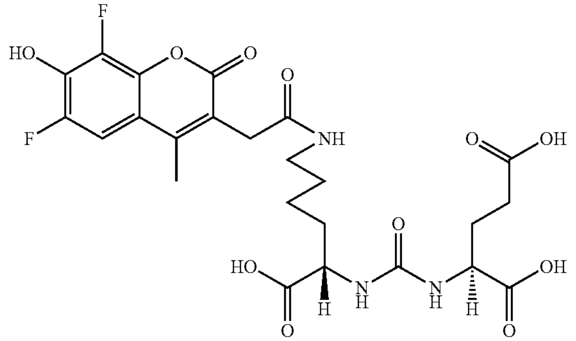

-continued
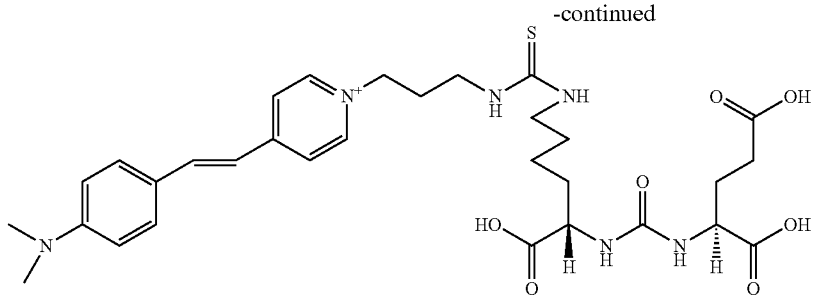
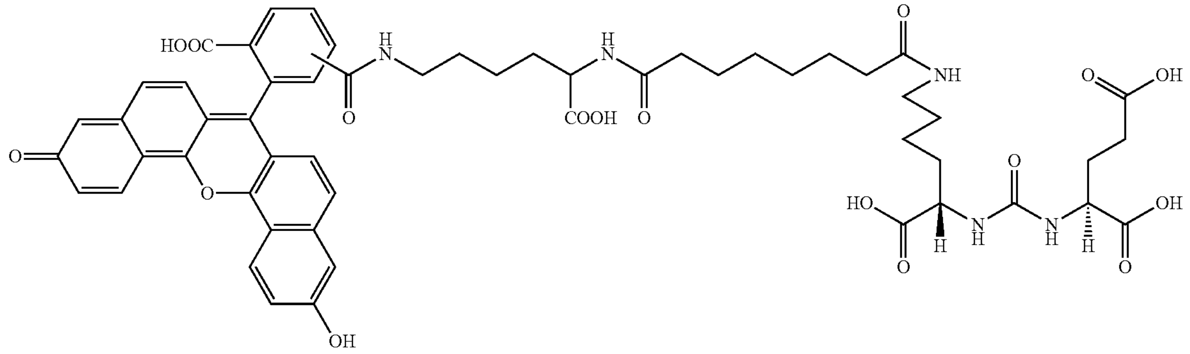
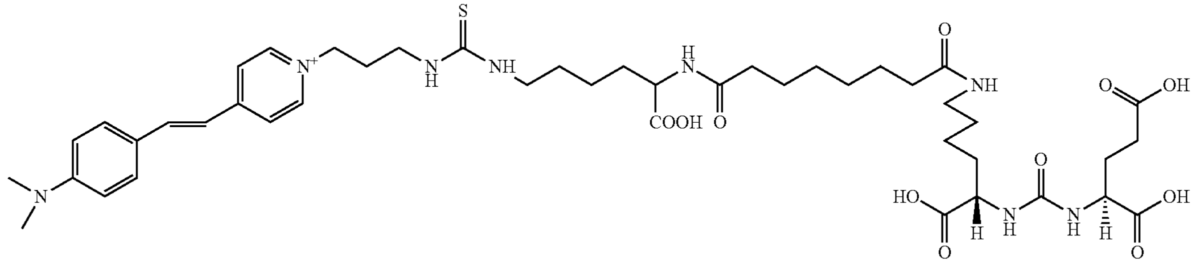
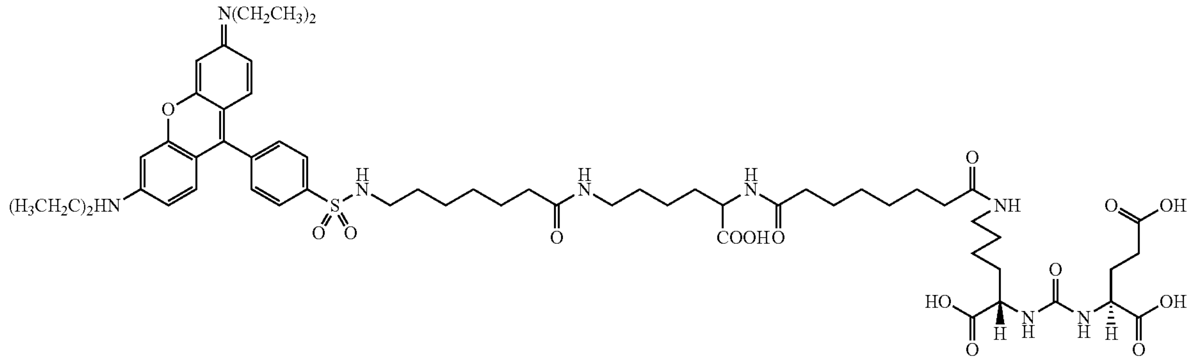
Embodiments include compounds having the structure
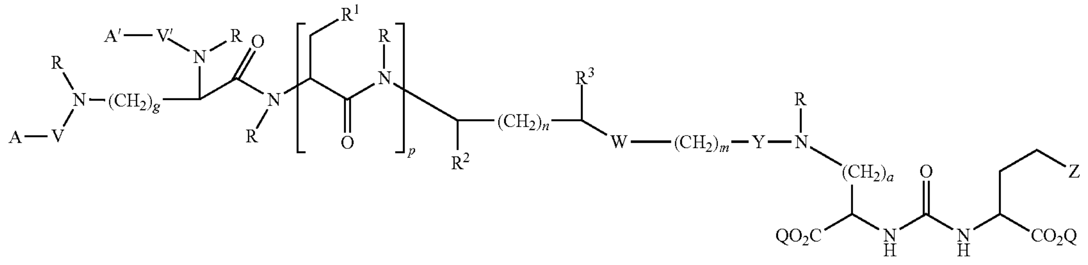

wherein Z is tetrazole or $CO_2Q$; each Q is independently selected from hydrogen or a protecting group, a is 1, 2, 3, or 4. One of A and A' is Ch and the other is FG, where FG is a fluorescent dye moiety which emits in the visible or near infrared spectrum and Ch is metal chelating moiety optionally including a chelated metal. R is each independently H or $C_1$-$C_4$ alkyl. V or V' are independently —C(O)—, —NRC(O)—, or —NRC(S)—. W is —NRC(O)—, —NRC(O)NR—, NRC(S)NR—, —NRC(O)O—, —OC(O)NR—, —OC(O)—, —C(O)NR—, or —C(O)O—. Y is —C(O)—, —NRC(O)—, —NRC(S)—, —OC(O)—. In exemplary embodiments m is 1, 2, 3, 4, 5, or 6; n is 1, 2, 3, 4, 5 or 6; and g is 1, 2, 3, 4, 5, or 6; p is 0, 1, 2, or 3, and when p is 2 or 3, each $R^1$ may be the same or different. $R^1$ is H, $C_1$-$C_6$ alkyl, $C_2$-$C_{12}$ aryl, or $C_4$-$C_{16}$ alkylaryl. $R^2$ and $R^3$ are independently H, $CO_2H$, or $CO_2R^4$, where $R^4$ is a $C_1$-$C_6$ alkyl, $C_2$-$C_{12}$ aryl, or $C_4$-$C_{16}$ alkylaryl, wherein when one of $R^2$ and $R^3$ is $CO_2H$ or $CO_2R^4$, the other is H. In some embodiments, the fluorescent dye moiety emits in the near infrared spectrum. Some embodiments further include a chelated metal.

In some embodiments, the compound has the structure shown below.

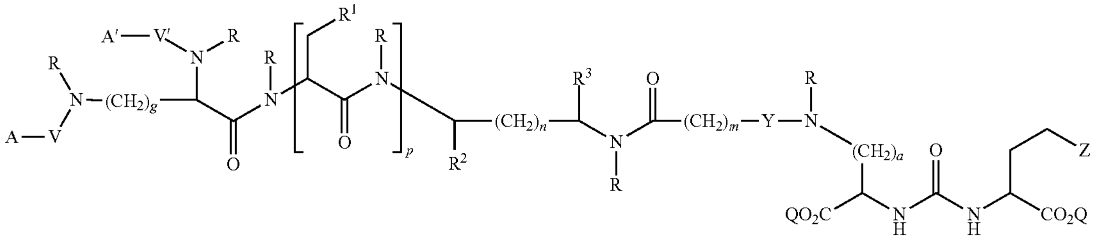

In some embodiments, the compound has the structure shown below.

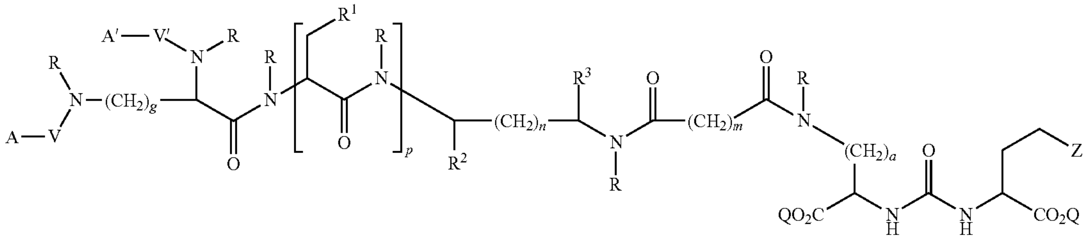

In some embodiments, the compound has the structure shown below.

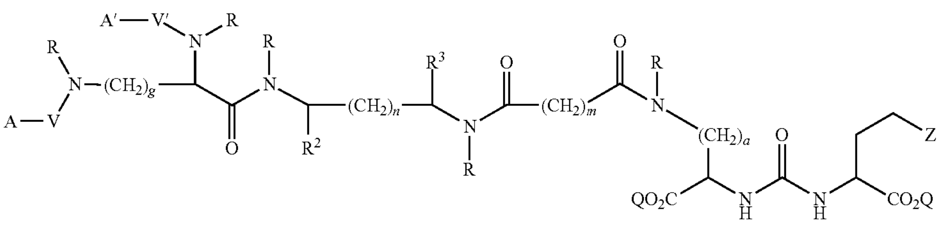

In some embodiments, the compound has the structure shown below.

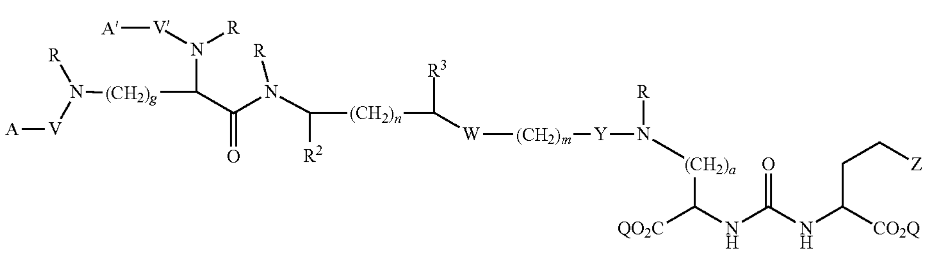

In some embodiments, p is 1, 2 or 3. In some embodiments, p is 2. In some embodiments $R^1$ is $C_2$-$C_{12}$ aryl. In some embodiments, $R^1$ is phenyl.

In some embodiments, p is 0.

In some embodiments, $R^3$ is $CO_2H$ and $R^2$ is H. In some embodiments, $R^2$ is $CO_2H$ and $R^3$ is H. In some embodiments, $R^2$ is $CO_2R^4$, and $R^3$ is H. In some embodiments, $R^3$ is $CO_2R^4$, and $R^2$ is H. In some embodiments $R^4$ is $C_2$-$C_{12}$ aryl, or $C_4$-$C_{16}$ alkylaryl. In some $R^4$ is benzyl. In some embodiments, $R^2$ is H, and $R^3$ is H.

In some embodiments V and V' are individually —C(O)— or —NRC(S)—. This means that one of V and V' may be —C(O)—, while the other is —NRC(S)—, or that both V and V' are either —C(O)— or —NRC(S)—. V and V' will be determined, in part, on the type of FG and Ch used.

FG is a fluorescent dye moiety which emits light in the visible or near infrared spectrum. Exemplary fluorescent dye moieties are described previously.

Ch is a metal chelating group. Suitable metal chelating groups are described previously. In some embodiments, the compound further includes a chelated metal. The list of Exemplary metals and isotopes thereof are described previously.

Some embodiments have the structure

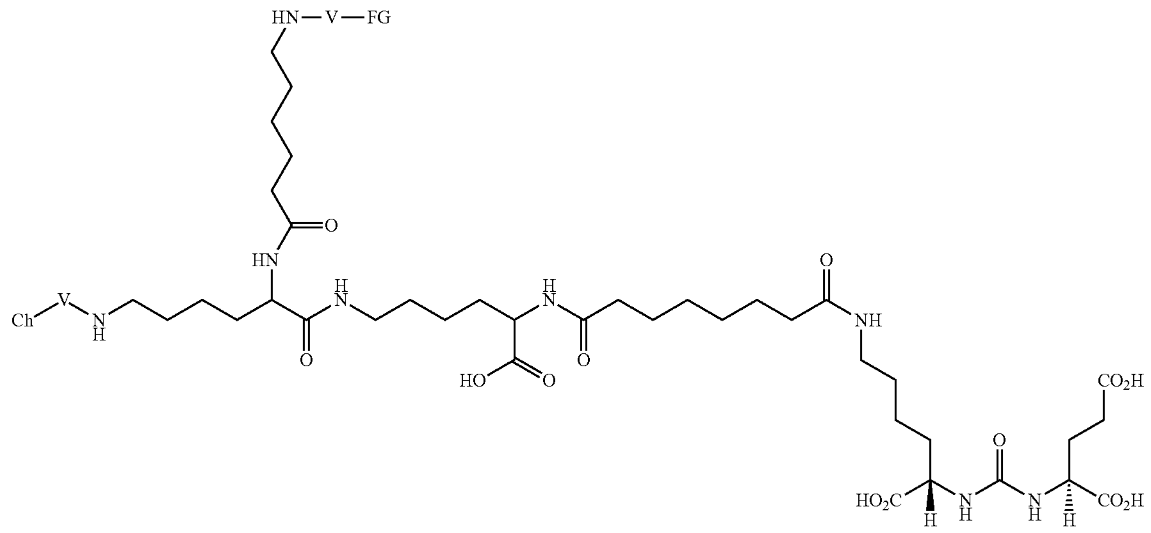

where FG and Ch are described previously, and each V is individually —C(O)— or —NRC(S)—.

Specific examples of compounds include the structures shown below.

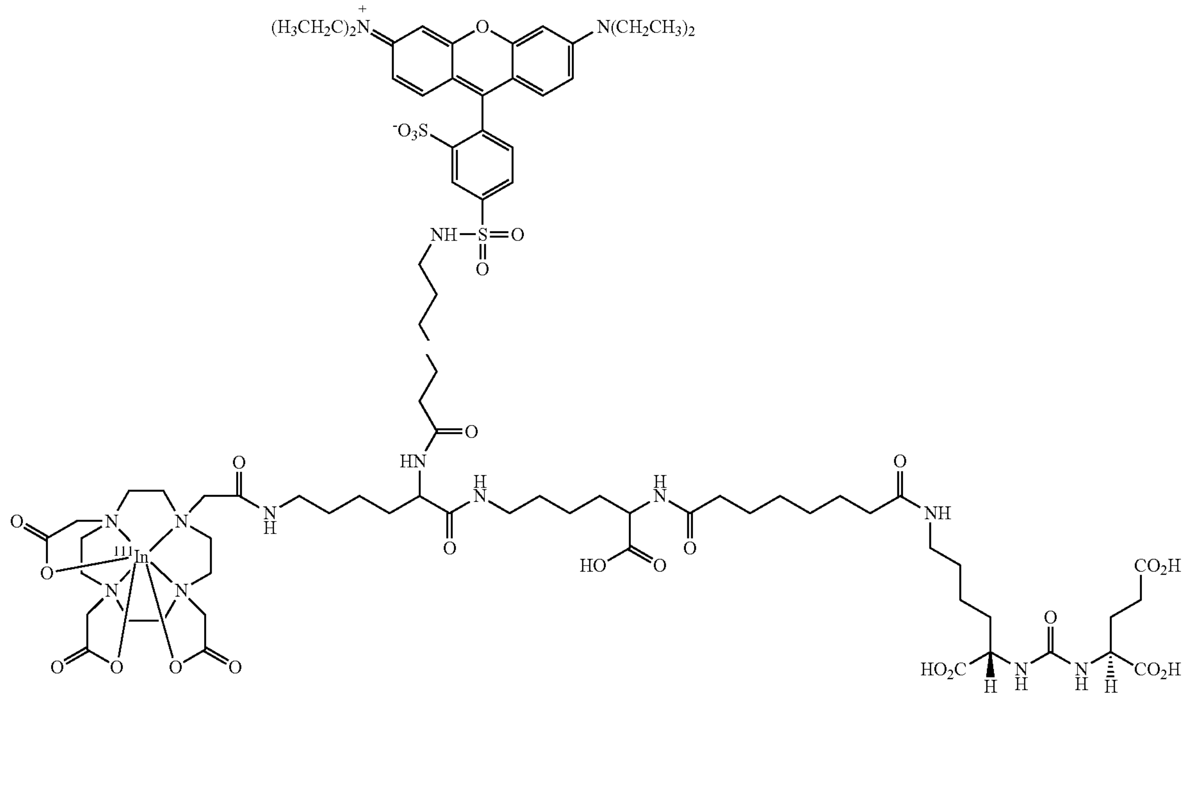

Embodiments include compounds having the structure

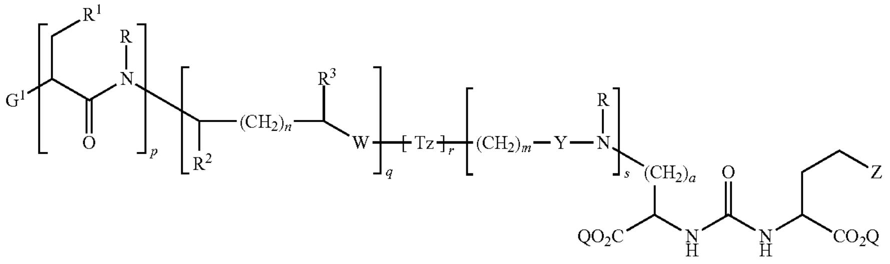

wherein the subunits associated with elements p, q, r, and s may be in any order. Z is tetrazole or $CO_2Q$; each Q is independently selected from hydrogen or a protecting group, and a is 1, 2, 3, or 4. R is each independently H or $C_1$-$C_4$ alkyl. In an exemplary embodiment r is 1. Tz is a triazole group having the structure

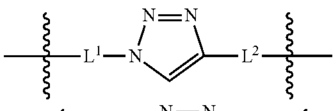

or

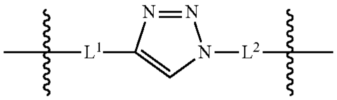

where $L^1$ is

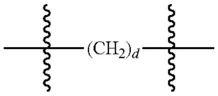

or

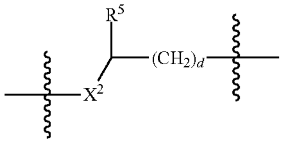

;

$L^2$ is

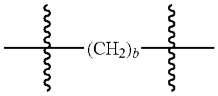

or

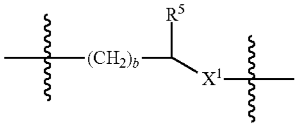

;

$X^1$ is —NRC(O)—, —NRC(O)NR—, NRC(S)NR—, or —NRC(O)O—; $X^2$ is —C(O)NR—, —NRC(O)NR—, NRC(S)NR—, or —OC(O)NR—; $R^5$ is H, $CO_2H$, or $CO_2R^6$, where $R^6$ is a $C_1$-$C_6$ alkyl, $C_2$-$C_{12}$ aryl, or $C_4$-$C_{16}$ alkylaryl; b is 1, 2, 3, or 4; and d is 1, 2, 3, or 4. In exemplary embodiments q is 0 or 1, W is —NRC(O)—, —NRC(O)NR—, NRC(S)NR—, —NRC(O)O—, —OC(O)NR—, —OC(O)—, —C(O)NR—, or —C(O)O—; n is 1, 2, 3, 4, 5 or 6; and $R^2$ and $R^3$ are independently H, $CO_2H$, or $CO_2R^4$, where $R^4$ is a $C_1$-$C_6$ alkyl, $C_2$-$C_{12}$ aryl, or $C_4$-$C_{16}$ alkylaryl, wherein if one of $R^2$ and $R^3$ is $CO_2H$ or $CO_2R^4$, then the other is H. In exemplary embodiments is 0 or 1; Y is —C(O)—, —NRC(O)—, —NRC(S)—, —OC(O); and m is 1, 2, 3, 4, 5, or 6. In exemplary embodiments p is 0, 1, 2, or 3, and when p is 2 or 3, each $R^1$ may be the same or different; and $R^1$ is H, $C_1$-$C_6$ alkyl, $C_2$-$C_{12}$ aryl, or $C_4$-$C_{16}$ alkylaryl. $G^1$ is a moiety selected from the group consisting of

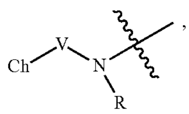

,

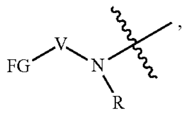

, and

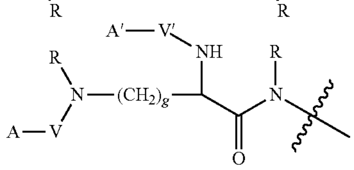

, where Ch is a metal chelating moiety, optionally including a chelated metal; FG is a fluorescent dye moiety which emits in the visible or near infrared spectrum; one of A and A' is Ch and the other is FG; V and V' are each independently —C(O)—, —NRC(O)—, —NRC(S)—, or —OC(O)—; and g is 1, 2, 3, 4, 5, or 6. In some embodiments, the fluorescent dye moiety emits in the near infrared spectrum. Some embodiments include a chelated metal. In some embodiments the subunits associated with elements p, q, and s are in the order shown. In some embodiments, p is 0.

Some embodiments have the structure shown below.

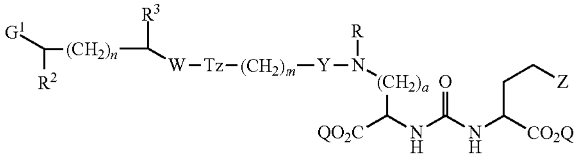

Some embodiments have the structure shown below.

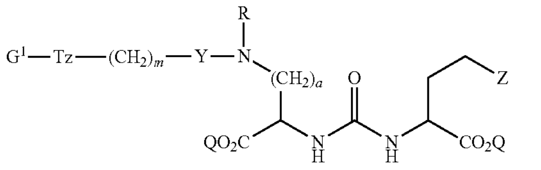

Some embodiments have the structure shown below.

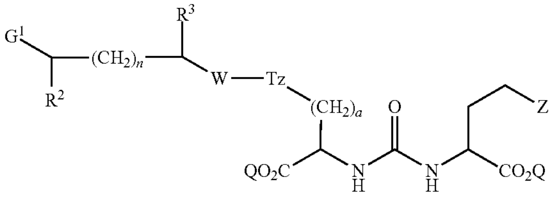

In some embodiments Y is —C(O)—. In some embodiments, W is —NRC(O)—.

In some embodiments, p is 1, 2 or 3. In some embodiments, p is 2. In some embodiments $R^1$ is $C_2$-$C_{12}$ aryl. In some embodiments, $R^1$ is phenyl.

In some embodiments, p is 0.

In some embodiments, $R^3$ is $CO_2H$ and $R^2$ is H. In some embodiments, $R^2$ is $CO_2H$ and $R^3$ is H. In some embodiments, $R^2$ is $CO_2R^4$, and $R^3$ is H. In some embodiments, $R^3$ is $CO_2R^4$, and $R^2$ is H. In some embodiments $R^4$ is $C_2$-$C_{12}$ aryl, or $C_4$-$C_{16}$ alkylaryl. In some $R^4$ is benzyl. In some embodiments, $R^2$ is H, and $R^3$ is H.

In some embodiments, V and V' are individually —C(O)— or —NRC(S)—.

FG is a fluorescent dye moiety which emits light in the visible or near infrared spectrum. Exemplary fluorescent dye moieties are described previously and may be used in these embodiments.

Ch is a metal chelating group. Suitable metal chelating groups are described previously. In some embodiments, the compound further includes a chelated metal. The list of exemplary metals and isotopes thereof are described previously and may be used in these embodiments.

Examples of compounds include the structures shown below

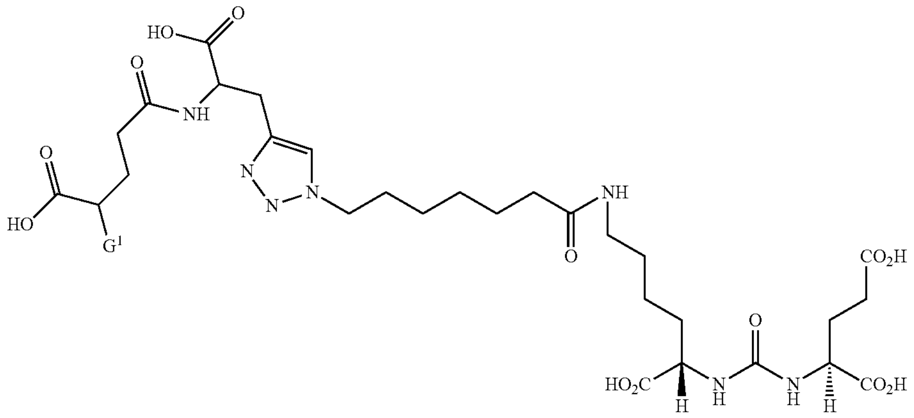

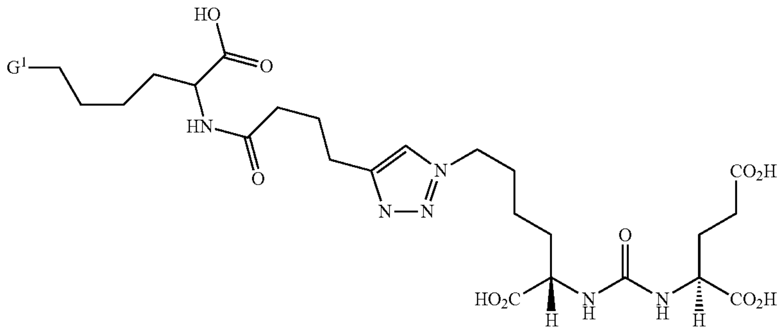

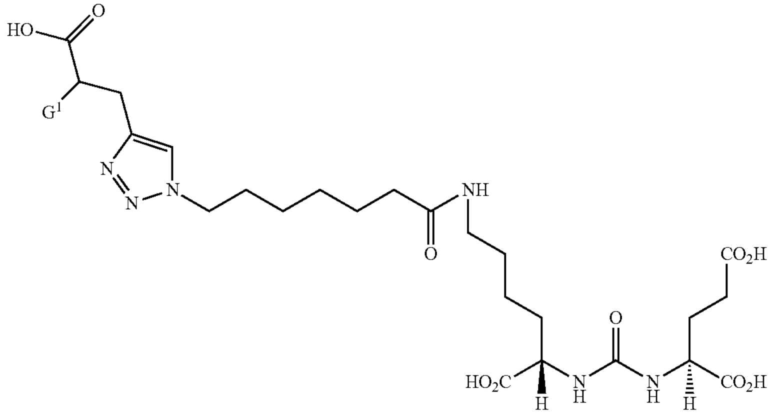

Embodiments of the invention also include intermediates used to make triazole compounds according to the various embodiments of the invention. Embodiments include compounds having the structure

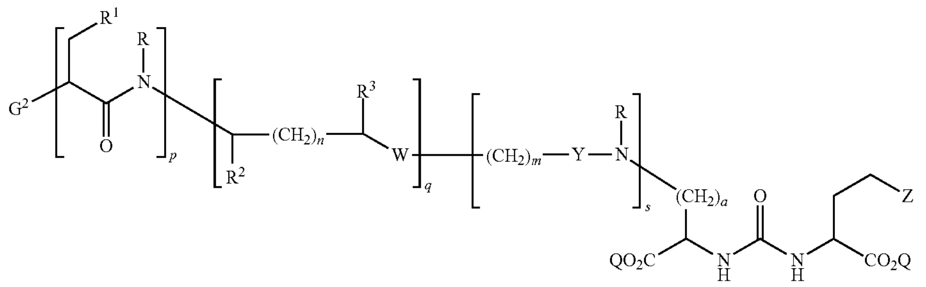

wherein the subunits associated with elements p, q, r, and s may be in any order. Z is tetrazole or $CO_2Q$; each Q is independently selected from hydrogen or a protecting group, a is 1, 2, 3, or 4, and R is each independently H or $C_1$-$C_4$ alkyl. Variable q is 0 or 1. W is —NRC(O)—, —NRC(O)NR—, NRC(S)NR—, —NRC(O)O—, —OC(O)NR—, —OC(O)—, —C(O)NR—, or —C(O)O—; $R^2$ and $R^3$ are independently H, $CO_2H$, or $CO_2R^4$, where $R^4$ is a $C_1$-$C_6$ alkyl, $C_2$-$C_{12}$ aryl, or $C_4$-$C_{16}$ alkylaryl, wherein if one of $R^2$ and $R^3$ is $CO_2H$ or $CO_2R^4$, then the other is H; n is 1, 2, 3, 4, 5 or 6.

Variable s is 0 or 1. Y is —C(O)—, —NRC(O)—, —NRC(S)—, —OC(O); and m is 1, 2, 3, 4, 5, or 6.

Variable p is 0, 1, 2, or 3, and when p is 2 or 3, each $R^1$ may be the same or different. $R^1$ is H, $C_1$-$C_6$ alkyl, $C_2$-$C_{12}$ aryl, or $C_4$-$C_{16}$ alkylaryl. $G^2$ is

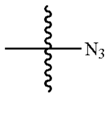 or 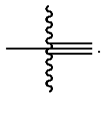

In some embodiments, the compound has the structure shown below.

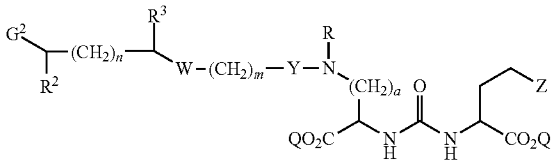

In some embodiments, the compound has the structure shown below.

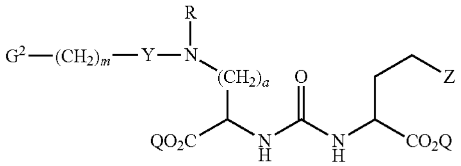

In some embodiments, the compound has the structure shown below.

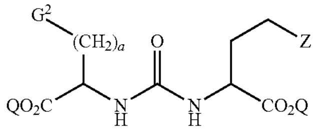

Examples include the compounds shown below.

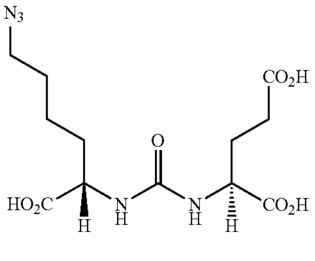

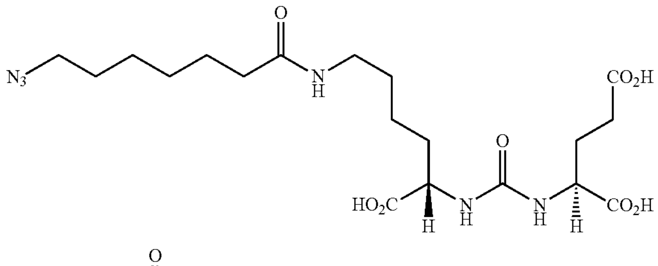

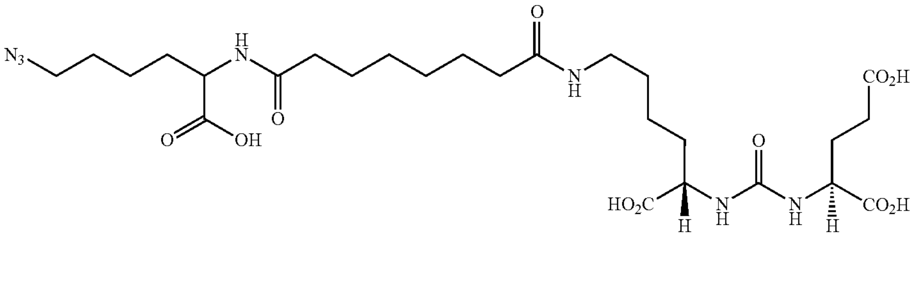

Other embodiments include pharmaceutically acceptable salts of the compounds described in any of the previous embodiments. As used herein, "pharmaceutically acceptable salts" refer to derivatives of the disclosed compounds wherein the parent compound is modified by making non-toxic acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, malefic, hydroxymaleic, phenylacetic, glutamic, benzoic, salicylic, mesylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. The pharmaceutically acceptable salts of the present invention can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are used, where practicable. Lists of additional suitable salts may be found, e.g., in Remington's Pharmaceutical Sciences, 17th ed., Mack Publishing Company, Easton, Pa., p. 1418 (1985).

Preparation

The compounds described in the above embodiments may be made using procedures known in the art. In general, the materials used will be determined by the desired structure, and the type of linkage used.

Often, the compounds are prepared by sequentially adding components to a preformed urea, such as the lysine-urea-glutamate compounds described in Banerjee et al. (J. Med. Chem. vol. 51, pp. 4504-4517, 2008). Other urea-based compounds may also be used as building blocks.

Compounds are assembled by reactions between different components, to form linkages such as ureas (—NRC(O)NR—), thioureas (—NRC(S)NR—), amides (—C(O)NR— or —NRC(O)—), or esters (—C(O)O— or —OC(O)—). Urea linkages may be readily prepared by reaction between an amine and an isocyanate, or between an amine and an activated carbonamide (—NRC(O)—). Thioureas may be readily prepared from reaction of an amine with an isothiocyanate. Amides (—C(O)NR— or —NRC(O)—) may be readily prepared by reactions between amines and activated carboxylic acids or esters, such as an acyl halide or N-hydroxysuccinimide ester. Carboxylic acids may also be activated in situ, for example, with a coupling reagent, such as a carbodiimide, or carbonyldiimidazole (CDI). Esters may be formed by reaction between alcohols and activated carboxylic acids. Triazoles are readily prepared by reaction between an azide and an alkyne, optionally in the presence of a copper (Cu) catalyst.

Protecting groups may be used, if necessary, to protect reactive groups while the compounds are being assembled. Suitable protecting groups, and their removal, will be readily available to one of ordinary skill in the art.

In this way, the compounds may be easily prepared from individual building blocks, such as amines, carboxylic acids, and amino acids.

Often, a Ch or FB group is placed on the compound by adding a metal chelating group or fluorescent dye to the compound toward the end of a synthesis, for example by reacting a reactive amine on the compound with an activated metal chelating group or fluorescent dye. A wide variety of metal chelating groups and fluorescent dyes are known in the art, with activated functional groups for reacting with amines. The type of metal chelating group will be determined, in part by the desired metal. Selecting a metal chelating group for a particular metal atom will be apparent to one of ordinary skill in the art. The fluorescent dye used with be determined, in part, by the desired wavelength of fluorescence, and may be readily selected by one of ordinary skill in the art.

Exemplary procedures for specific compounds are described in the Examples below. Other compounds within the scope of the claims can be prepared using readily apparent modifications of these procedures.

Uses

Compounds described above, including various radiolabeled compounds, may be used for diagnostic, imaging, or therapeutic purposes. In general, the suitability of a particular radioisotope for a particular purpose (i.e. imaging or therapeutic) is well understood in the art. Other exemplary embodiments are compounds used as precursors for radiolabeled compounds, in which a metal or radioactive isotope of a metal may be added to the compound. Some compounds according to the invention are intermediates for forming other compounds of the invention.

Imaging

Embodiments include methods of imaging one or more cells, organs or tissues comprising exposing cells to or administering to a subject an effective amount of a compound with an isotopic label suitable for imaging. In some embodiments, the one or more organs or tissues include prostate tissue, kidney tissue, brain tissue, vascular tissue or tumor tissue. The cells, organs or tissues may be imaged while within an organism, either by whole body imaging or intraoperative imaging, or may be excised from the organism for imaging.

In another embodiment, the imaging method is suitable for imaging studies of PSMA inhibitors, for example, by studying competitive binding of non-radiolabeled inhibitors. In still another embodiment, the imaging method is suitable for imaging of cancer, tumor or neoplasm. In a further embodiment, the cancer is selected from eye or ocular cancer, rectal cancer, colon cancer, cervical cancer, prostate cancer, breast cancer and bladder cancer, oral cancer, benign and malignant tumors, stomach cancer, liver cancer, pancreatic cancer, lung cancer, corpus uteri, ovary cancer, prostate cancer, testicular cancer, renal cancer, brain cancer (e.g., gliomas), throat cancer, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, neurofibromatosis, tuberous sclerosis, hemangiomas, and lymphangiogenesis.

The imaging methods of the invention are suitable for imaging any physiological process or feature in which PSMA is involved. Typically, imaging methods are suitable for identification of areas of tissues or targets which express high concentrations of PSMA. Typical applications include imaging glutamateric neurotransmission, presynaptic glutamatergic neurotransmission, malignant tumors or cancers that express PSMA, prostate cancer (including metastasized prostate cancer), and angiogenesis. Essentially all solid tumors express PSMA in the neovasculture. Therefore, methods of the present invention can be used to image nearly all solid tumors including lung, renal cell, glioblastoma, pancreas, bladder, sarcoma, melanoma, breast, colon, germ cell, pheochromocytoma, esophageal and stomach. Also, certain benign lesions and tissues including endometrium, schwannoma and Barrett's esophagus can be imaged according to the present invention.

The methods of imaging angiogenesis are suitable for use in imaging a variety of diseases and disorders in which angiogenesis takes place. Illustrative, non-limiting, examples include tumors, collagen vascular disease, cancer, stroke, vascular malformations, and retinopathy. Methods of imaging angiogenesis are also suitable for use in diagnosis and observation of normal tissue development.

PSMA is frequently expressed in endothelial cells of capillary vessels in peritumoral and endotumoral areas of various malignancies such that compounds of the invention and methods of imaging using same are suitable for imaging such malignancies.

In certain embodiments, the radiolabeled compound is stable in vivo.

In certain embodiments, the radiolabeled compound is detectable by positron emission tomography (PET) or single photon emission computed tomography (SPECT).

In some embodiments, the subject is a human, rat, mouse, cat, dog, horse, sheep, cow, monkey, avian, or amphibian. In another embodiment, the cell is in vivo or in vitro. Typical subjects to which compounds of the invention may be administered will be mammals, particularly primates, especially humans. For veterinary applications, a wide variety of subjects will be suitable, e.g. livestock such as cattle, sheep, goats, cows, swine and the like; poultry such as chickens, ducks, geese, turkeys, and the like; and domesticated animals particularly pets such as dogs and cats. For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids and cell samples of the above subjects will be suitable for use such as mammalian, particularly primate such as human, blood, urine or tissue samples, or blood urine or tissue samples of the animals mentioned for veterinary applications. In other in vitro applications, the cells or tissues are present in culture or in suspension.

Imaging agents of the invention may be used in accordance with the methods of the invention by one of skill in the art. Images can be generated by virtue of differences in the spatial distribution of the imaging agents which accumulate at a site when contacted with PSMA. The spatial distribution may be measured using any means suitable for the particular label, for example, a gamma camera, a PET apparatus, a SPECT apparatus, a fluorescence camera and the like. The extent of accumulation of the imaging agent may be quantified using known methods for quantifying radioactive emissions. A particularly useful imaging approach employs more than one imaging agent, or a bimodal agent having a fluorescent dye moiety and a metal chelating group, such as those described above, to perform simultaneous studies.

In general, a detectably effective amount of the imaging agent is administered to a subject. As used herein, "a detectably effective amount" of the imaging agent is defined as an amount sufficient to yield an acceptable image using equipment which is available for clinical use. A detectably effective amount of the imaging agent may be administered in more than one injection. The detectably effective amount of the imaging agent can vary according to factors such as the degree of susceptibility of the individual, the age, sex, and weight of the individual, idiosyncratic responses of the individual, and the dosimetry. Detectably effective amounts of the imaging agent can also vary according to instrument and film-related factors. Optimization of such factors is well within the level of skill in the art. The amount of imaging agent used for diagnostic purposes and the duration of the imaging study will depend upon the radionuclide used to label the agent, the body mass of the patient, the nature and severity of the condition being treated, the nature of therapeutic treatments which the patient has undergone, and on the idiosyncratic responses of the patient. Ultimately, the attending physician will decide the amount of imaging agent to administer to each individual patient and the duration of the imaging study.

In some embodiments, the compounds are excreted from tissues of the body quickly to prevent prolonged exposure to the radiation of the radiolabeled compound administered to the patient. Generally, the compounds are excreted from tissues of the body slowly enough to allow sufficient time for imaging or other use. Typically compounds of the invention are eliminated from the body in less than about 24 hours. More typically, compounds of the invention are eliminated from the body in less than about 16 hours, 12 hours, 8 hours, 6 hours, 4 hours, 2 hours, 90 minutes, or 60 minutes. Exemplary compounds are eliminated in between about 60 minutes and about 120 minutes.

In some embodiments of the invention, the compounds are designed to increase uptake in PSMA positive cells (i.e. tumor cells). For example, highly hydrophilic compounds may be excreted quickly. Compounds with increased hydrophobicity, such as compounds having hydrophobic linkers, may have longer circulation times, thereby providing more prolonged supply of tracer to bind to cells. According to embodiments of compounds according to the invention, hydrophobicity can be increased when, for example, p is 1 or more, or when $R^2$ or $R^3$ is $CO_2R^4$ Therapeutic Uses Embodiments of the invention include methods of treating a tumor comprising administering a therapeutically effective amount of a compound discussed above, where the compound includes a therapeutically effective radioisotope. The development of low molecular weight radiotherapeutic agents is much different from developing radiopharmaceuticals for imaging in that longer tumor residence times may be important for the former.

In some embodiments, the tumor cells may express PSMA, such as prostate tumor cells or metastasized prostate tumor cells. In other embodiments, a tumor may be treated by targeting adjacent or nearby cells which express PSMA. For example, vascular cells undergoing angiogenesis associated with a tumor may be targeted. Essentially all solid tumors express PSMA in the neovasculture. Therefore, methods of the present invention can be used to treat nearly all solid tumors including lung, renal cell, glioblastoma, pancreas, bladder, sarcoma, melanoma, breast, colon, germ cell, pheochromocytoma, esophageal and stomach. Also, certain benign lesions and tissues including endometrium, schwannoma and Barrett's esophagus can be treated according to the present invention. Examples of therapeutically effective radioisotopes include $^{90}Y$, $^{177}Lu$, $^{186}Re$, $^{188}Re$, $^{67}Cu$, $^{225}Ac$, $^{213}Bi$, $^{212}Bi$, $^{67}Ga$, $^{111}In$, $^{153}Sm$, $^{212}Pb$ $^{131}I$ and $^{211}At$.

Cell Sorting

Embodiments include methods for sorting cells by exposing the cells to a compound discussed above, where the compound includes a fluorescent dye moiety, followed by separating cells which bind the compound from cells which do not bind the compound.

Fluorescent compounds described above bind to PSMA on cells that express PSMA on the cell surface. In some cases, fluorescent compound is internalized. Cells binding the fluorescent compound appear fluorescent, and may be imaged using fluorescence microscopy. Fluorescence-activated cell sorting (FACS) or flow cytometry may be used to separate PSMA positive cells from PSMA negative cells.

Intraoperative Tumor Mapping

Embodiments of the invention include methods of intraoperative tumor mapping or intraoperative photodiagnosis (PDD) by administering an effective amount of a compound discussed above to a subject, where the compound includes a fluorescent dye moiety. According to such embodiments, an effective amount of a compound is an amount sufficient to produce a detectable level of fluorescence when used for intraoperative tumor mapping or PDD. The compounds bind to, and may be internalized into, cells, particularly tumor cells, that express PSMA. The fluorescent compounds thereby define the boundaries of the tumor, allowing for accurate surgical removal. The compounds that includes a fluorescent dye moiety may also be used to visualize circulating tumor cells that express PSMA.

Pharmaceutical Compositions and Kits

The compounds discussed herein can be formulated into various compositions, for use in diagnostic, imaging or therapeutic treatment methods. The compositions (e.g. pharmaceutical compositions) can be assembled as a kit. Generally, a pharmaceutical composition comprises an effective amount (e.g., a pharmaceutically effective amount, or detectably effective amount) of a compound described above.

A composition of the invention can be formulated as a pharmaceutical composition, which comprises a compound of the invention and pharmaceutically acceptable carrier. By a "pharmaceutically acceptable carrier" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, $18^{th}$ ed., Mack Publishing Company, 1990. Some suitable pharmaceutical carriers will be evident to a skilled worker and include, e.g., water (including sterile and/or deionized water), suitable buffers (such as PBS), physiological saline, cell culture medium (such as DMEM), artificial cerebral spinal fluid, or the like.

A pharmaceutical composition or kit of the invention can contain other pharmaceuticals, in addition to the compound. The other agent(s) can be administered at any suitable time during the treatment of the patient, either concurrently or sequentially.

One skilled in the art will appreciate that the particular formulation will depend, in part, upon the particular agent that is employed, and the chosen route of administration. Accordingly, there is a wide variety of suitable formulations of compositions of the present invention.

One skilled in the art will appreciate that a suitable or appropriate formulation can be selected, adapted or developed based upon the particular application at hand. Dosages for compositions of the invention can be in unit dosage form. The term "unit dosage form" as used herein refers to physically discrete units suitable as unitary dosages for animal (e.g. human) subjects, each unit containing a predetermined quantity of an agent of the invention, alone or in combination with other therapeutic agents, calculated in an amount sufficient to produce the desired effect in association with a pharmaceutically acceptable diluent, carrier, or vehicle.

One skilled in the art can easily determine the appropriate dose, schedule, and method of administration for the exact formulation of the composition being used, in order to achieve the desired effective amount or effective concentration of the agent in the individual patient.

The dose of a composition of the invention, administered to an animal, particularly a human, in the context of the present invention should be sufficient to produce at least a detectable amount of a diagnostic or therapeutic response in the individual over a reasonable time frame. The dose used to achieve a desired effect will be determined by a variety of factors, including the potency of the particular agent being administered, the pharmacodynamics associated with the agent in the host, the severity of the disease state of infected individuals, other medications being administered to the subject, etc. The size of the dose also will be determined by the existence of any adverse side effects that may accompany the particular agent, or composition thereof, employed. It is generally desirable, whenever possible, to keep adverse side effects to a minimum. The dose of the biologically active material will vary; suitable amounts for each particular agent will be evident to a skilled worker.

Other embodiments provide kits including a compound according to the invention. In certain embodiments, the kit provides packaged pharmaceutical compositions having a pharmaceutically acceptable carrier and a compound of the invention. In some embodiments the packaged pharmaceutical composition will include the reaction precursors necessary to generate the compound of the invention upon combination with a radionuclide. Other packaged pharmaceutical compositions provided by the present invention further comprise indicia comprising at least one of: instructions for preparing compounds according to the invention from supplied precursors, instructions for using the composition to image cells or tissues expressing PSMA, or instructions for using the composition to image glutamatergic neurotransmission in a patient suffering from a stress-related disorder, or instructions for using the composition to image prostate cancer.

In certain embodiments, a kit according to the invention contains from about 1 mCi to about 30 mCi of the radionuclide-labeled imaging agent described above, in combination with a pharmaceutically acceptable carrier. The imaging agent and carrier may be provided in solution or in lyophilized form. When the imaging agent and carrier of the kit are in lyophilized form, the kit may optionally contain a sterile and physiologically acceptable reconstitution medium such as water, saline, buffered saline, and the like. The kit may provide a compound of the invention in solution or in lyophilized form, and these components of the kit of the invention may optionally contain stabilizers such as NaCl, silicate, phosphate buffers, ascorbic acid, gentisic acid, and the like. Additional stabilization of kit components may be provided in this embodiment, for example, by providing the reducing agent in an oxidation-resistant form. Determination and optimization of such stabilizers and stabilization methods are well within the level of skill in the art.

A "pharmaceutically acceptable carrier" refers to a biocompatible solution, having due regard to sterility, p[Eta], isotonicity, stability, and the like and can include any and all solvents, diluents (including sterile saline, Sodium Chloride Injection, Ringer's Injection, Dextrose Injection, Dextrose and Sodium Chloride Injection, Lactated Ringer's Injection and other aqueous buffer solutions), dispersion media, coatings, antibacterial and antifungal agents, isotonic agents, and the like. The pharmaceutically acceptable carrier may also contain stabilizers, preservatives, antioxidants, or other additives, which are well known to one of skill in the art, or other vehicle as known in the art.

The contents of all cited references (including literature references, issued patents, published patent applications) as cited throughout this application are hereby expressly incorporated by reference. The invention and the manner and process of making and using it, are described in such full, clear, concise and exact terms as to enable any person skilled in the art to which it pertains, to make and use the same.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

It is to be understood that the foregoing describes exemplary embodiments of the present invention and that modifications may be made therein without departing from the spirit or scope of the present invention as set forth in the appended claims.

EXAMPLES

The present invention is further illustrated by the following examples which should not be construed as limiting in any way. The practice of the present invention will employ, unless otherwise indicated, conventional techniques, which are within the skill of the art. Such techniques are explained fully in the literature.

Example 1

2-{3-[5-(7-{5-[4-(2-Amino-2-carboxy-ethyl)-[1,2,3]triazol-1-yl]-1-carboxy-pentylcarbamoyl}-heptanoylamino)-1-carboxy-pentyl]-ureido}-pentanedioic acid, compound SRV32

The compound SRV32 was prepared in three steps following the scheme shown below.

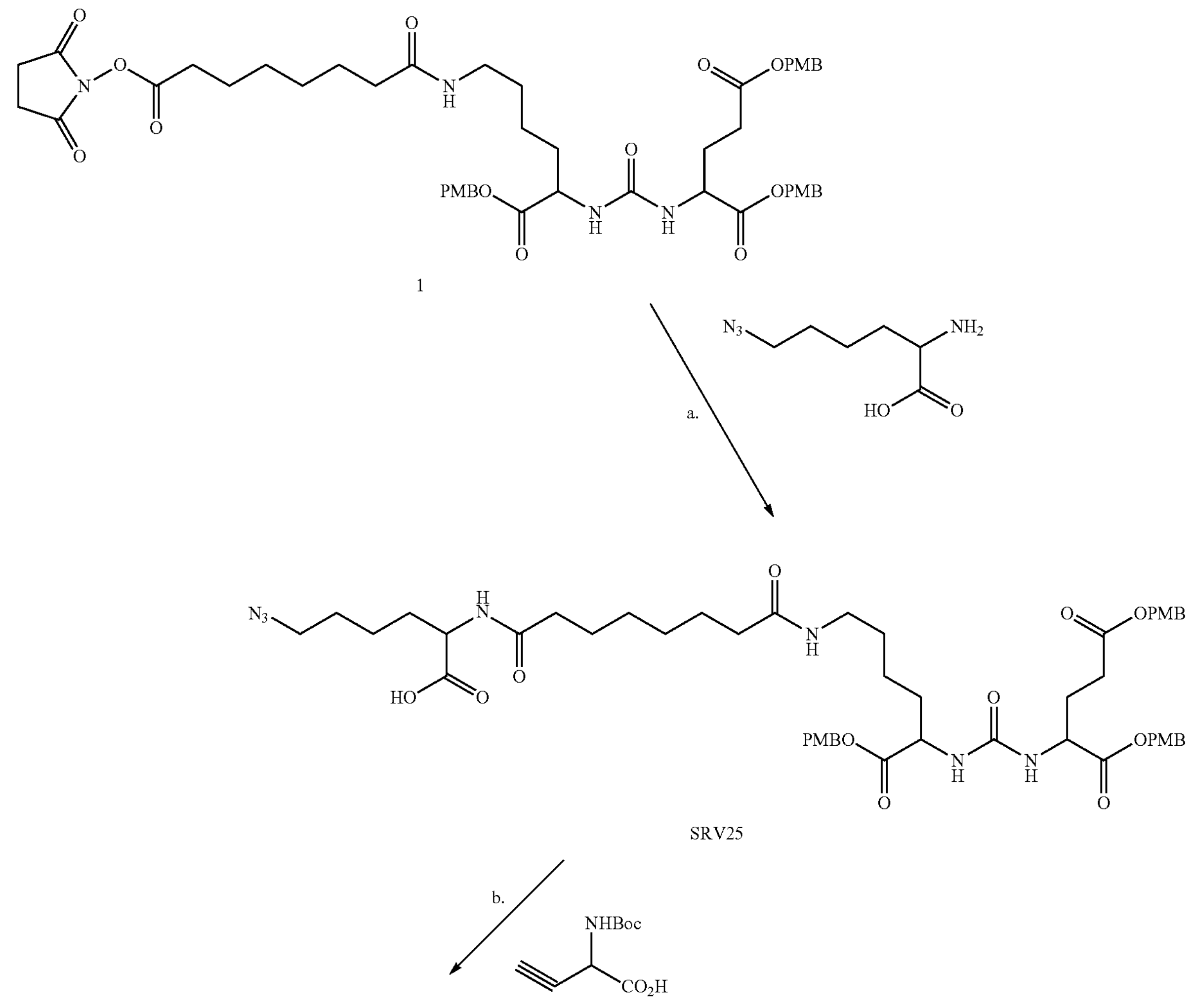

1

SRV25

-continued

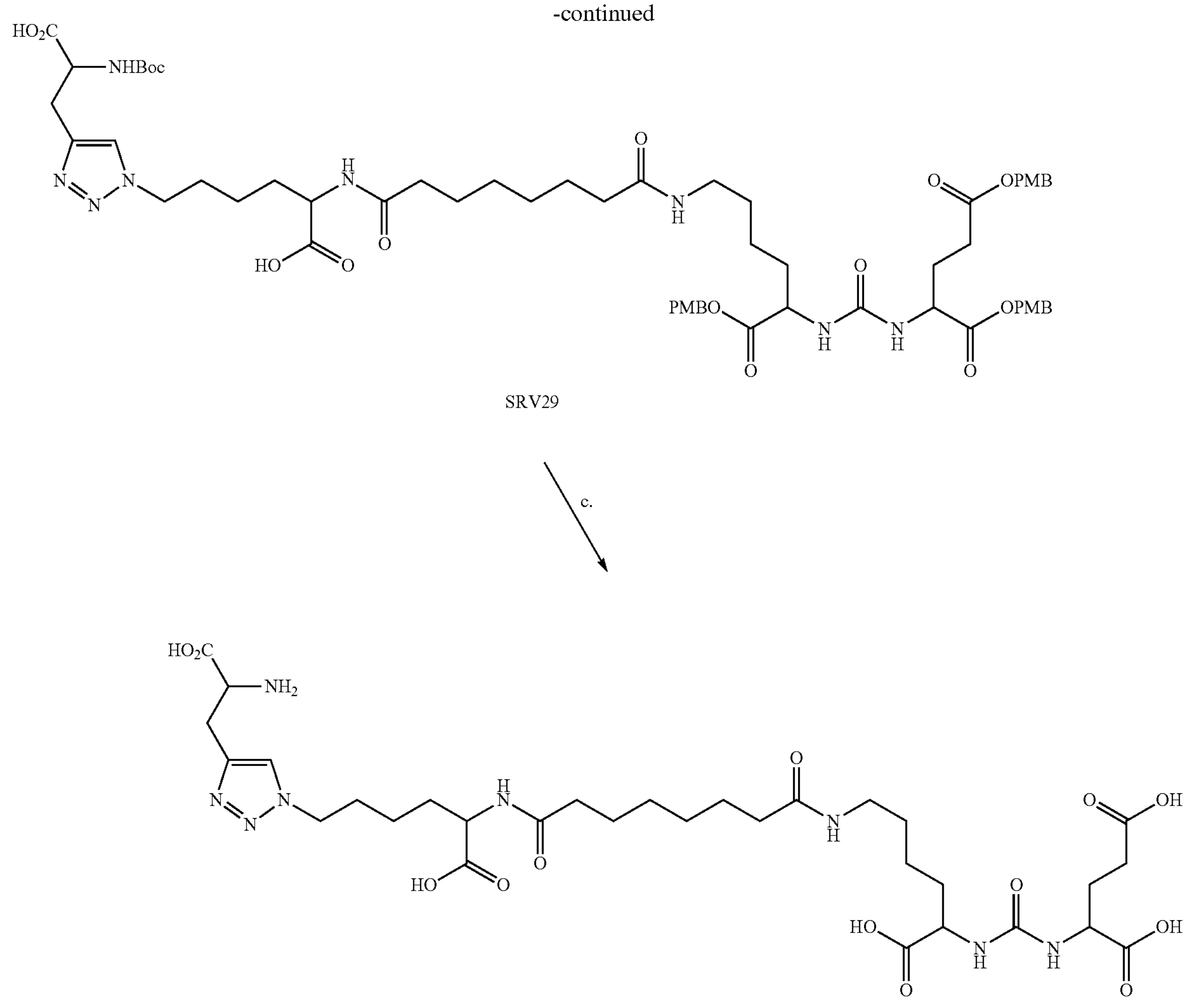

SRV29

SRV32 a. TEA, DMF, 16 h, rt, b. Cu(OAc)2, Sodium, ascorbate, water/t-BuOH(1:1), rt, 18 h;
b. $Cu(OAc)_2$, Na-ascrobate, $H_2O$, rt, 12 h;
c. $TFA/CH_2Cl_2$(1:1), 16 h, rt.

The compound 1 was prepared from literature method (Banerjee et al., J Med Chem, vol. 51, pp. 4504-4517, 2008). To a solution of compound 1 (100 mg, 0.107 mmol in 5 ml DMF) was added H-Lys(ϵ-azide)-OH (20 mg, 0.107 mmol) (Boc-Lys(Azide)-OH was purchased from Anaspec. The removal of Boc group was done by treating the commercial compound with 1:1 $TFA:CH_2Cl_2$ at room temperature for 4 hr, and the solution was stirred for 16 h at rt. The solvent was removed under vacuum. The solid residue thus obtained was dissolved in 10 ml ethyl acetate and extracted with 3×10 mL water. Organic layer was dried under vacuum to get a colorless solid as the protected azido urea compound SRV25. ESIMS: 991$[M+H]^+$. To the Compound SRV25 (60 mg, 0.06 mmol in 1 ml t-BuOH), was added N(a)-Boc-L-propargylglycine(Anaspec) (14 mg, 0.012 mmol in 1 ml t-BuOH), followed by $Cu(OAc)_2.H_2O$ (2 mg, 0.012 mmol in 1 ml water) and sodium ascorbate (4.75 mg, 0.024 mmol in 1 ml water) and the mixture stirred at room temperature for 12 h. The product was extracted into $CH_2Cl_2$ and washed twice with aqueous NaCl. The aqueous phases were re-extracted with $CH_2C_2$. The organic phases were combined, dried over $Na_2SO_4$ and evaporated. The product, compound SRV29, was purified by a silica gel pipette column eluted with solution of 90/10 $CH_2Cl_2$/MeOH. ESIMS: Calcd for $C_{60}H_{82}N_8O_{18}$ 1203.57, found 1204$[M+1]^+$.

The compound SRV29 was dissolved in 2 ml 1/1 $CHCl_3$/TFA and stirred overnight. The solution was removed under vacuum to get a colorless solid. The solid was washed 3 times with 5 ml $CH_2Cl_2$ to remove impurities. The crude solid, compound SRV32 was further purified by HPLC using a 85/15 water/acetonitrile (0.1% TFA in each) flow rate 4 ml, $R_t$=10.2 min. ESMS: 742.77[M+1]+, $^1$H NMR ($D_2O$) δ: 7.46 (M, 1H), 5.2 (m, 2H) 4.35 (m, 1H), 4.26 (m, 1H), 4.18 (m, 1H), 3.80-3.70 (m, 1H), 3.18 (t, J=6 Hz, 2H), 2.69 (m, 2H), 2.51 (t, J=7.6 Hz, 2H), 2.40-2.18 (m, 25H).

Radiolabeling with Tc-99m was performed by the same procedure described previously (Banerjee et al., J Med Chem, vol. 51, pp. 4504-4517, 2008).

Biodistribution and Imaging

A single SCID mouse implanted with both a PC-3 PIP (PSMA+) and a PC-3 flu (PSMA−) xenograft was injected intravenously with compound $^{99m}$Tc-SRV32 in saline. At 0.5 hr, 1 hr, 2 h, and 5 h p.i. the mouse was anesthetized with isoflurane and maintained under 1% isoflurane in oxygen. The mouse was positioned on the X-SPECT (Gamma Medica, Northridge, Calif.) gantry and was scanned using two low energy, high-resolution pinhole collimators (Gamma Medica) rotating through 360° in 6° increments for 45 seconds per increment. All gamma images were reconstructed using Lunagem software (Gamma Medica, Northridge, Calif.). Immediately following SPECT acquisition, the mice were then scanned by CT (X-SPECT) over a 4.6 cm field-of-view using a 600 μA, 50 kV beam. The SPECT and CT data were then coregistered using the supplier's software (Gamma Medica, Northridge, Calif.) and displayed using AMIDE (http://amide.sourceforge.net/). Data were reconstructed using the Ordered Subsets-Expectation Maximization (OS-EM) algorithm.

Tissue biodistribution was measured. Results are summarized in the following table. $^{99m}$Tc-SRV32 exhibited high uptake (~7% ID/g at 30 minutes), and good clearance from non-target tissues.

| Tissue | 30 min | 60 min | 120 min | 300 min |
|---|---|---|---|---|
| blood | 1.38 ± 0.4 | 0.63 ± 0.1 | 0.61 ± 0.3 | 0.19 ± 0.1 |
| liver | 14.26 ± 1.0 | 9.81 ± 2.0 | 5.65 ± 0.5 | 3.06 ± 0.6 |
| stomach | 0.77 ± 0.1 | 0.42 ± 0.09 | 0.29 ± 0.1 | 0.18 ± 0.1 |
| spleen | 26.10 ± 9.0 | 17.31 ± 6.6 | 5.80 ± 1.9 | 1.26 ± 0.5 |
| kidney | 139.53 ± 17.2 | 144.65 ± 15.1 | 151.23 ± 37.1 | 80.00 ± 8.4 |
| muscle | 0.56 ± 0.1 | 0.40 ± 0.2 | 0.16 ± 0.1 | 0.51 ± 0.6 |
| small intestine | 1.94 ± 1.1 | 0.74 ± 0.3 | 0.39 ± 0.2 | 0.26 ± 0.2 |
| large intestine | 0.61 ± 0.1 | 0.36 ± 0.1 | 0.53 ± 0.4 | 2.96 ± 1.3 |
| bladder | 1.07 ± 0.1 | 3.09 ± 2.6 | 5.39 ± 7.1 | 2.74 ± 2.1 |
| PC-3 PIP | 6.67 ± 1.6 | 5.32 ± 1.2 | 3.77 ± 0.8 | 2.19 ± 0.5 |
| PC-3 flu | 0.75 ± 0.2 | 0.45 ± 0.3 | 0.35 ± 0.2 | 0.43 ± 0.4 |

A single SCID mouse implanted with a PSMA+ LnCaP xenograft was injected intravenously with compound $^{99m}$Tc-SRV32 in saline. At 0.5 hr, and 3.5 hr p.i. the mouse was anesthetized with isoflurane and maintained under 1% isoflurane in oxygen. The mouse was positioned on the X-SPECT (Gamma Medica, Northridge, Calif.) gantry and was scanned using two low energy, high-resolution pinhole collimators (Gamma Medica) rotating through 360° in 6° increments for 45 seconds per increment. All gamma images were reconstructed using Lunagem software (Gamma Medica, Northridge, Calif.) Immediately following SPECT acquisition, the mice were scanned by CT (X-SPECT) over a 4.6 cm field-of-view using a 600 μA, 50 kV beam. The SPECT and CT data were then coregistered using the supplier's software (Gamma Medica, Northridge, Calif.) and displayed using AMIDE (http://amide.sourceforge.net/). Data were reconstructed using the Ordered Subsets-Expectation Maximization (OS-EM) algorithm. Images are shown in FIG. 1.

Comparative Example 1

Under the same conditions, tumor uptake for compound $^{99m}$Tc-L1, shown below, was determined. Results are summarized in the following table. The data show that while $^{99m}$TC-L1 shows good retention, compound $^{99m}$Tc-SRV32 has greater retention in vivo both for target tumor and non-target tissues, and lower GI uptake than the previous $^{99m}$TcL1 compound at initial time points.

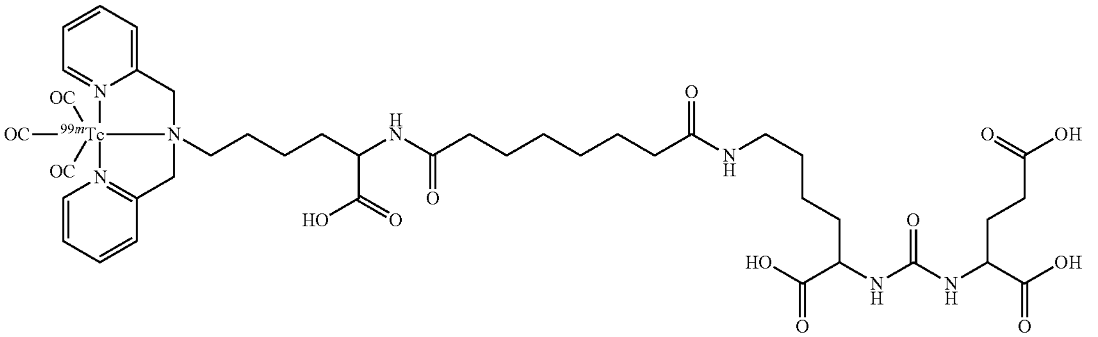

$^{99m}$Tc-L1

| Tissue | 30 min | 60 min | 120 min | 300 min |
|---|---|---|---|---|
| PC-3 PIP | 7.9 ± 4 | 3.9 ± 0.6 | 2.0 ± 0.8 | 0.8 ± 0.5 |
| PC-3 flu | 0.3 ± 0.2 | 0.2 ± 0.1 | 0.05 ± 0.02 | 0.01 ± 0.01 |

Example 2

$^{68}$Ga Compounds

General

Solvents and chemicals obtained from commercial sources were of analytical grade or better and used without further purification. All experiments were performed in duplicate or triplicate to ensure reproducibility. Analytical thin-layer chromatography (TLC) was performed using Aldrich aluminum-backed 0.2 mm silica gel Z19, 329-1 plates and visualized by ultraviolet light (254 nm), 12 and 1% ninhydrin in EtOH. Flash chromatography was performed using silica gel purchased from Bodman (Aston Pa.), MP SiliTech 32-63 D 60A. $^1$H NMR spectra were recorded on either a Varian Mercury 400 MHz or on a Bruker Ultrashield™ 400 MHz spectrometer. Chemical shifts (δ) are reported in ppm downfield by reference to proton resonances resulting from incomplete deuteration of the NMR solvent. Low resolution ESI mass spectra were obtained on a Bruker Daltonics Esquire 3000 Plus spectrometer. Higher-resolution FAB mass spectra were obtained on a JOEL JMS-AX505HA mass spectrometer in the mass spectrometer facility at the University of Notre Dame. Optical rotation was measured on a Jasco P-1010 polarimeter. Infrared spectra were obtained on a Bruker Tensor 27 spectrometer. High-performance liquid chromatography (HPLC) purification of new compounds was performed using a Phenomenex $C_{18}$ Luna 10-x□250 mm$^2$ column on a Waters 600E Delta LC system with a Waters 486 tunable absorbance UV/Vis detector, both controlled by Empower software.

For purification of radiolabeled [$^{68}$Ga]SRV100, a Varian Microsorb-Mv $C_{18}$ 250×4.6 mm$^2$ column was used. HPLC was performed using the following isocratic conditions: For Method 1, the mobile phase was 80% solvent A (0.1% TFA in water) and 20% solvent B (0.1% TFA in $CH_3CN$), flow rate 4 mL/min; for Method 2, the mobile phase was 80% solvent A and 20% solvent B, flow rate 1 mL/min. Method 1 was used for purification of compounds SRV27, [$^{69/71}$Ga]SRV27, SRV100, [$^{69/71}$Ga]SRV100 and [$^{68}$Ga]SRV27.

For purification of [$^{68}$Ga]SRV100 Method 2 was used. For radiosynthetic purification, HPLC was performed on a Varian Prostar System (Palo Alto, Calif.), equipped with a model 490 UV absorbance detector and a Bioscan NaI scintillation detector connected to a Bioscan Flow-count system controlled by Empower software.

Radiochemistry $^{68}$Ga labeling protocol for compound SRV27 was done following a literature procedure (Zhernosekov et al., J Nucl Med, vol. 48, pp. 1741-1748, 2007). A detailed description is given below.

1. 13.2mCi of $^{68}$Ga in 7 mL of 0.1N HCl were obtained from more than 1-year-old 740-MBq generator. The solution was transferred on a cation-exchange cartridge, Phenomenex Strata-X-C tubes (33 μm strong cation exchange resin, part no. 8B-S029-TAK, 30 mg/l ml).
2. The column was eluted with 5 ml of a solution of 20/80 0.10N hydrochloric acid/acetone. The eluant remaining on the cation-exchanger was removed by passage of nitrogen. These two processes aimed to remove most of the remaining chemical and radiochemical impurities from the resin, whereas $^{68}$Ga(III) should quantitatively remain on the column.
3. The column was filled with 150 μL of a 2.4/97.6 0.05N HCl/acetone solution. About 2 min standing appeared to be best for complete desorption of the $^{68}$Ga(III) from the resin into the liquid phase. An additional 250 μL of this mixture were applied, and the purified $^{68}$Ga(III) was obtained in 400 μL of this eluent overall.
4. The fraction (400 μL eluent) was used directly for the labeling of DOTA-urea compound. The processed activity was added to 500 μL pure $H_2O$ in a standard glass reagent vial containing 100 μl (92 nmol, 1 mg/mL solution) of ligand. No buffer solution was added. The reaction vial was heated at 95° C. for 10 min. The complexation was monitored by injecting aliquots of 100 μl (210 μCi) of the solution in HPLC. Product obtained=160 μCi. Radiochemical Yield=(160/210)×100=76.19% (without decay correction). Solvent system 80/20 water/acetonitrile (0.1% TFA in each), $R_t$ (retention time)=25 min for the compound and $R_t$=19 min for the free ligand. Product obtained=5.92 MBq. For [$^{68}$Ga]SRV27, radiochemical yield: 76.2% (without decay correction). HPLC was performed by Method 1 as described in the General experimental section. $R_t$=25 min for the desired product and $R_t$=19 min for the free ligand. For [$^{68}$Ga]SRV100, radiochemical yield: 70%. HPLC was performed by Method 2 as mentioned in General experimental section. $R_t$=22.5 min for the desired product and $R_t$=16 min for the free ligand.

Cell Lines and Tumor Models

PC-3 PIP (PSMA+) and PC-3 flu (PSMA) cell lines were obtained from Dr. Warren Heston (Cleveland Clinic) and were maintained as previously described (Mease et al., *Clin Cancer Res*, vol. 14, pp. 3036-3043, 2008). LNCaP cells were obtained from American Type Culture Collection (ATCC, Manassas, Va.) and were maintained as per ATCC guidelines. All cells were grown to 80-90% confluence before trypsinization and formulation in Hank's Balanced Salt Solution (HBSS, Sigma, St. Louis, Mo.) for implantation into mice.

Animal studies were undertaken in compliance with institutional guidelines related to the conduct of animal experiments. For biodistribution studies of [$^{68}$Ga]SRV27, and [$^{68}$Ga]SRV100 and imaging studies of [$^{68}$Ga]SRV100, male SCID mice (NCI) were implanted subcutaneously with 1-5×10$^6$ PSMA+ PC-3 PIP and PSMA− PC-3 flu cells behind either shoulder. For imaging studies of [$^{68}$Ga]SRV27, male SCID mice (NCI) were implanted subcutaneously with 5×10$^6$ LNCaP cells behind the right shoulder. Mice were imaged or used in biodistribution studies when the tumor xenografts reached 3-5 mm in diameter.

Synthesis of SRV27

2-{3-[5-(7-{1-Benzyloxycarbonyl-5-[2-(4,7,10-tris-carboxymethyl-1,4,7,10tetraazacyclododec-1-yl)-acetylamino]pentylcarbamoyl}-heptanoylamino)-1-carboxy-pentyl]-ureido}-pentanedioic acid (SRV27)

Compound SRV27 was prepared in three steps according the following scheme.

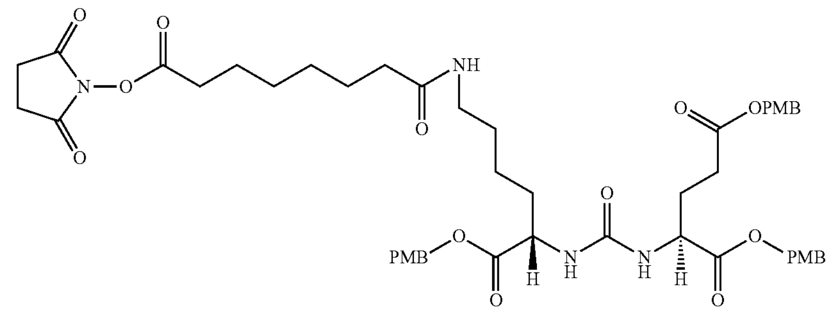
1
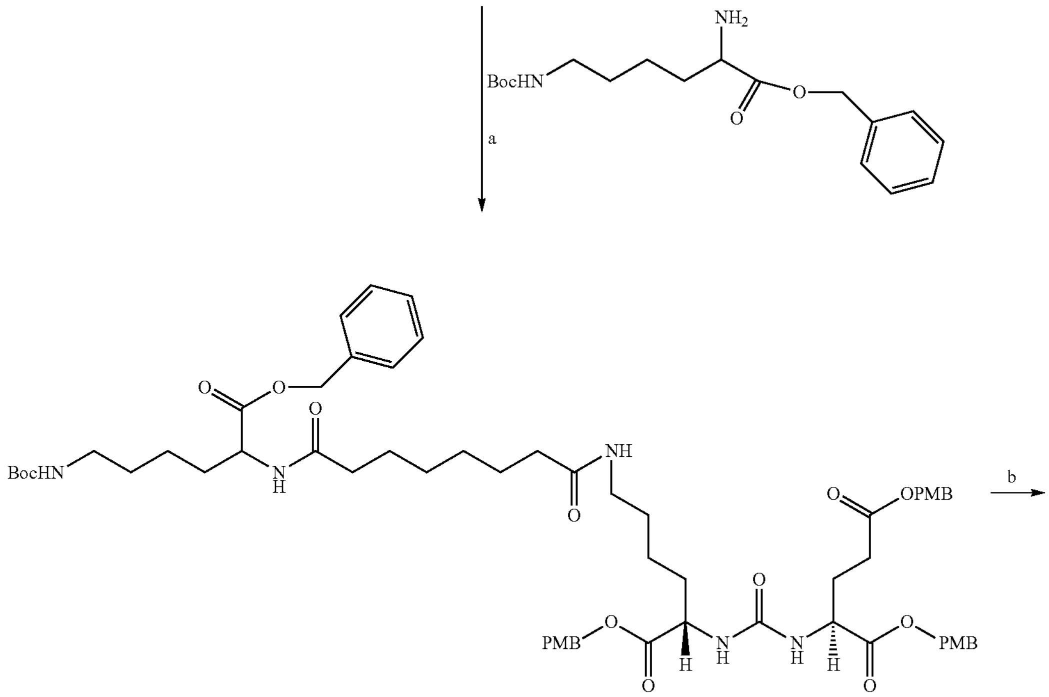
2
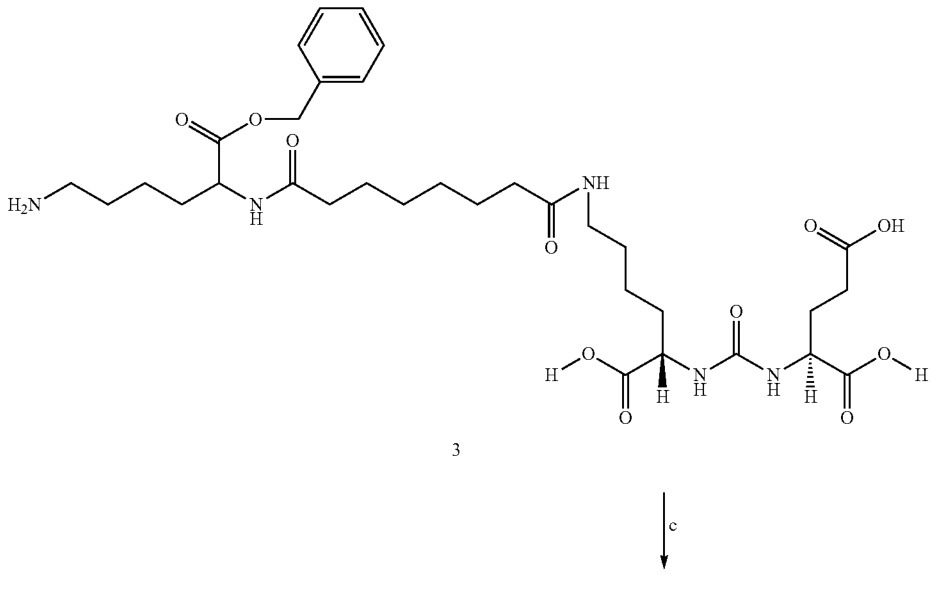
3

-continued

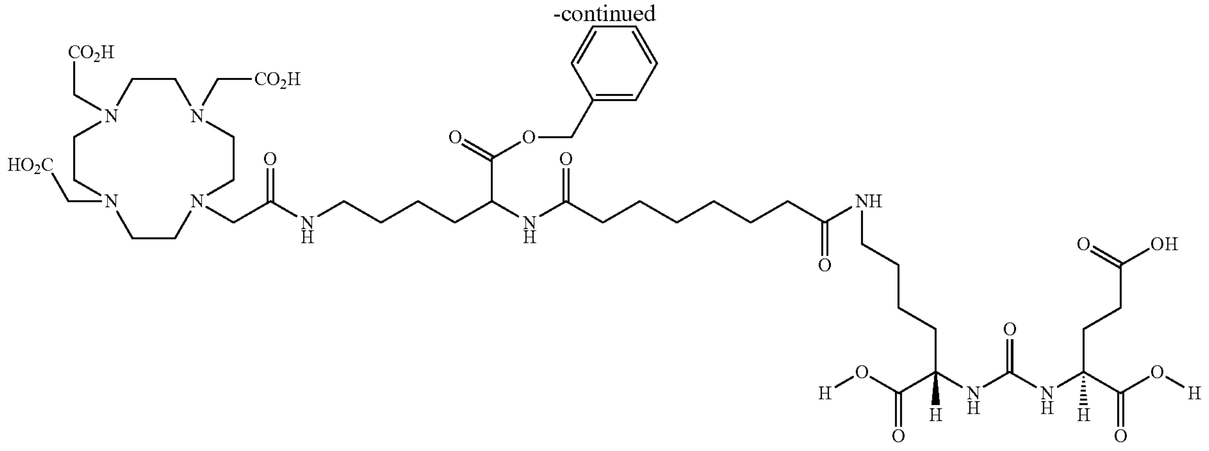

SRV27 a) $NEt_3$, DMF, rt, 16 h; b) TFA/$CH_2Cl_2$, rt, 16 h; c)DOTA—NHS,DMF, TEA, rt, 16 h.

Compound 1 was prepared according to a literature method (Banerjee et al., J Med Chem, vol. 51, pp. 4504-4517, 2008). To a solution of compound 1 (100 mg, 0.11 mmol in mL DMF) was added H-Lys(Boc)-OBz (36 mg, 0.11 mmol) (Hamachi et al., *Chem. Eur. J.*, vol. 5, pp. 1503-1511, 1999). The solution was stirred for 16 h at ambient temperature. The solvent was removed under vacuum. The solid residue thus obtained was dissolved in 10 mL ethyl acetate and extracted with 3x10 mL water. The organic layer was dried under vacuum to provide a colorless solid ESIMS: 1154 $[M+1]^+$. This crude compound was dissolved in 3 mL $CHCl_3$ followed by addition of 3 mL TFA at 0° C. The solution was allowed to stir overnight at ambient temperature. The volume of the solution was reduced under vacuum and the solid residue was washed with 3x5 mL $CH_2Cl_2$ to remove impurities. The colorless solid residue, 3, was dried under vacuum to give 80 mg of compound 3. Compound 3 was purified further by using a 2 g Sep Pak $C_{18}$ cartridge with a solution of 85/15 water/acetonitrile (0.1% TFA in each). $^1H$ NMR ($D_2O$, δ): 7.5 (bm, 5H), 4.27 (m, 1H), 4.12 (m, 1H), 3.99 (m, 1H), 3.04 (m, 4H), 2.38 (m, 2H), 2.3-1.0 (m, 27H). ESIMS: 694 $[M+1]^+$. To a solution of DOTA-mono-NHS (54 mg, 0.11 mmol in 5 mL DMF) was added 3 (80 mg, 0.08 mmol) and TEA (60 μL, 0.43 mmol) and the solution was allowed to stir for 16 h at ambient temperature. Solvent was removed under vacuum and the crude solid, SRV27, was purified by HPLC Method 1, retention time 19 min. Yield: ~40%. ESMS: $1080[M+H]^+$, HRESI$^+$-MS: Calcd. for $C_{49}H_{77}N_9O_{18}$, 1080.5487 [M+H], found: 1080.5459. $^1$HNMR ($D_2O$) δ: 7.88 (m, 4H), 4.26-4.1 (m, 5H), 3.45-3.18 (m, 16H), 2.52-2.43 (m, 16H), 2.40-2.18 (m, 25H). 13C ($CD_3CO_2D$) d: 177.5, 177.6, 175.3, 172.3, 160.6, 160.2, 159.8, 159.5, 135.5, 128.5, 128.4, 119.9, 117, 114.0, 111.3, 67.3, 55.5, 53.1, 51.0, 49.9, 30.7, 28.0, 26.4, 25.1.

2-{3-[5-(7-{1-Benzyloxycarbonyl-5-[2-(4,7,10-tris-carboxymethyl-1,4,7,10tetraaza-cyclododec-1-yl)-acetylamino]pentylcarbamoyl}-heptanoylamino)-1-carboxy-pentyl]-ureido}-pentanedioic acid Gallium (III), SRV31 ([$^{69/71}$Ga]-SRV27)

To a solution of $GaNO_3$ (10 mg, 39 μmol) in deionized water was added compound SRV27 (4.2 mg, 39 μmol) in 1 mL deionized water and the resulting solution was heated in boiling water for 10 min. The solvent was evaporated to dryness and the crude residue was purified by HPLC using a 80/20 water/acetonitrile (0.1% TFA in each), flow rate 8 ml/min. Retention time for the product was at 12 min. Yield: ~35% ESMS: $1146[M+H]^+$, $^1H$ NMR ($D_2O$) δ: 7.88 (m, 4H), 4.26-4.1 (m, 5H), 3.45 (m, 8H) 3.18 (m, 8H), 2.69 (m, 8H), 2.51 (m, 8H), 2.40-2.18 (m, 25H).

SRV100

2-[3-(1-Carboxy-5-{7-[5-carboxy-5-(3-phenyl-2-{3-phenyl-2-[2-(4,7,10-tris-carboxymethyl-1,4,7,10-tetraaza-cyclododec-1-yl)-acetylamino]-propionylamino}-propionylamino)-pentylcarbamoyl]-heptanoylamino}-pentyl)-ureido]-pentanedioic acid, (SRV100)

Figure 4:
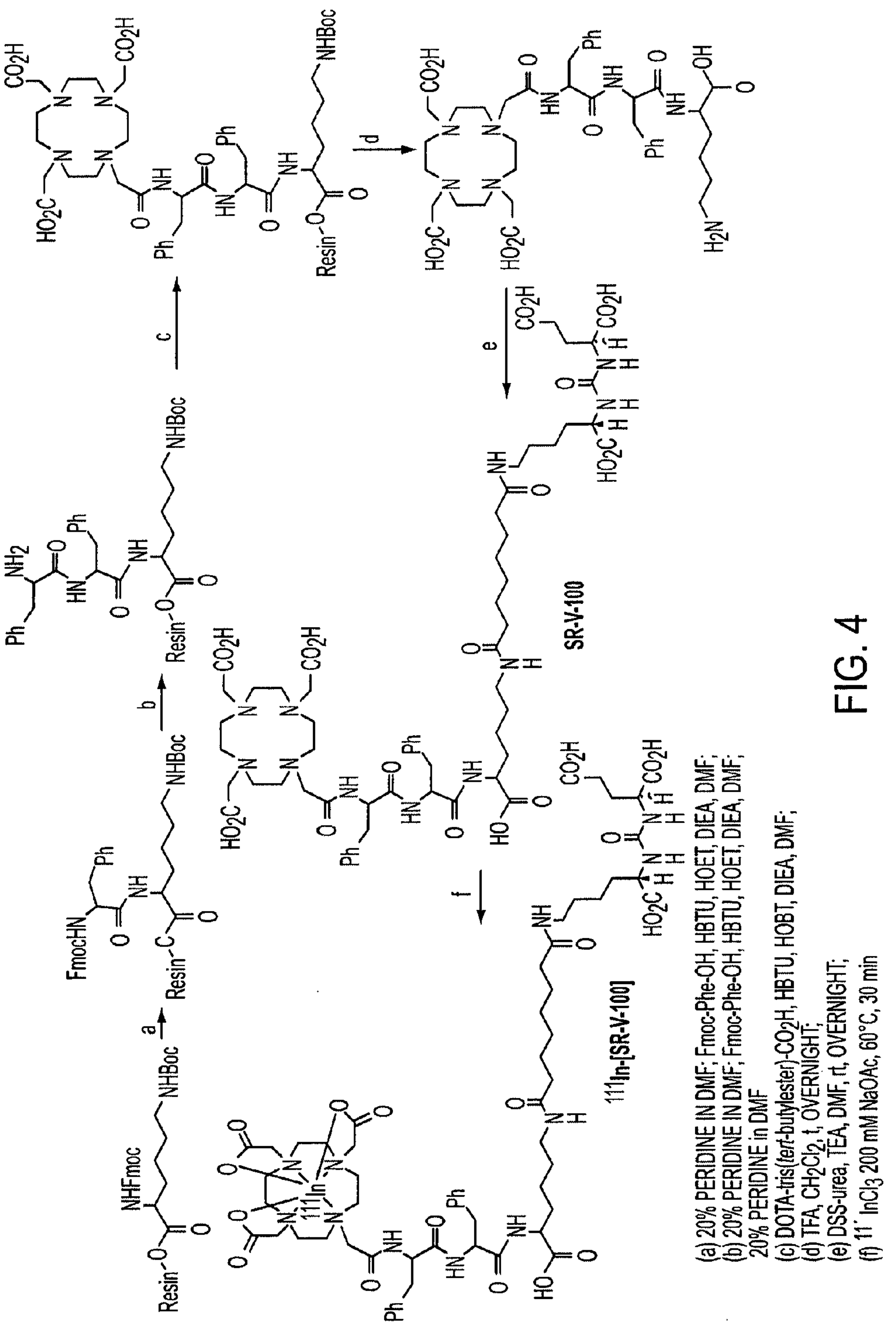
FIG. 4 shows a synthetic scheme for exemplary compound SRV100 and [$^{111}$In]SRV100.

Compound SRV100 was prepared according to the scheme shown in FIG. 4. Fmoc-Lys(Boc)-Wang resin (100 mg, 0.43 mM) was allowed to swell with $CH_2Cl_2$ (3 mL) followed by DMF (3 mL). A solution of 20% piperidine in DMF (3x3 mL) was added to the resin that was then shaken gently on a mechanical shaker for 30 min at ambient temperature. The resin was washed with DMF (3x3 mL) and $CH_2Cl_2$ (3x3 mL). Formation of free amine was assessed by the Kaiser test (Kaiser et al., *Anal Biochem, vol.* 34, pp. 595-598, 1970). After swelling the resin in DMF, a solution of Fmoc-Phe-OH (3 eq), HBTU (3 eq), HOBt (3 eq), and DIPEA (4.0 eq) in DMF was added and gently shaken for 2 h. The resin was then washed with DMF (3x3 mL) and $CH_2Cl_2$ (3x3 mL). The coupling efficiency was assessed by the Kaiser Test. That aforementioned sequence was repeated for two more coupling steps with Fmoc-Phe-OH and DOTA-(t-butyl ester)$_3$-$CO_2H$. The resulting compound was cleaved from the resin using TFA: $CH_2Cl_2$ (1:1) and concentrated under vacuum to produce the free amine. The concentrated product was purified by using a $C_{18}$ SepPak Vac 2 g column. The product was eluted with a solution 70/30 water/acetonitrile (0.1% TFA in each). ESIMS:827 $[M+1]^+$. Lyophilized amine (10 mg, 12 mmol in 2 mL DMF) was added to 1 (prepared separately) (20 mg, 21.4 mmol in 1 mL DMF) followed by TEA (214 mmol, 30 μL) and then stirred at 25° C. for 16 h. After solvent removal, solid residue was treated with 3 mL TFA: $CH_2Cl_2$ to remove the PMB group. The residue was washed 2x5 mL $CH_2Cl_2$ to remove impurities. The colorless solid residue thus obtained was purified by a C18 SepPak Vac 2 g column using an eluent of 70/30 water/acetonitrile (0.1% TFA in each) to produce SRV100 (SR-V-100). The product was further purified using preparative RP-HPLC by Method 1, retention time 17 min. Yield: ~30%. ESMS m/Z: 1284[M+H]+, HRESI+-MS: Calcd. for $C_{68}H_{90}N_{11}O_{20}$, 1284.6365 [M+H], found: 1284.6358. $^1H$ NMR ($CD_3CO_2D$) δ: 7.35-7.20 (m, 10H), 4.86 (bm, 2H), 4.57-4.46 (4H), 4.4-2.8 (m, 14H), 2.51 (t, 2h), 2.4-1.2 (m, 28H). 13C ($CD_3CO_2D$) δ: 176.5, 177, 177.06, 177.6, 173.6, 173.24, 161.3, 160.92, 160.53, 160.14, 159.77, 137.95, 137.06, 130.5, 129.5, 127.9, 127.71, 120.8, 118.0, 115.1, 112.3, 56.1, 55.5, 53.5, 53.3, 40.1, 38.8, 36.832.6, 31.8, 30.7, 29.42, 27.9, 26.53.

2-[3-(1-Carboxy-5-{7-[5-carboxy-5-(3-phenyl-2-{3-phenyl-2-[2-(4,7,10-tris-carboxymethyl-1,4,7,10tetraaza-cyclododec-1-yl)-acetylamino]propionylamino}-propionylamino)-pentylcarbamoyl]-heptanoylamino}-pentyl)-ureido]-pentanedioic acid Gallium (III), [$^{69/71}$Ga]SRV100

This compound was prepared according to the same general procedure as described for [$^{69/71}$Ga]SRV27. Compound [$^{69/71}$Ga]SRV100 was purified by Method 1, retention time 22 min. Yield: ~30%. ESMS m/Z: 1351[M+H]$^+$, HRESI$^+$-MS: Calcd. For $C_{68}H_{86}GaN_{11}NaO_{20}$, 1372.5204 [M+Na]$^+$, found: 1372.5199.

Compound Characterization—Lipophilicity

Partition coefficients, $\log_{o/w}$ (pH=7.4) values were determined according to a literature procedure (Antunes et al., *Bioconjug Chem*, vol. 18, pp. 84-92, 2007). Briefly, a solution of either [$^{68}$Ga]SRV27 or [$^{68}$Ga]SRV100 was added to a presaturated solution of 1-octanol (5 mL) mixed with phosphate buffered saline (PBS) (5 mL) in a 15 mL centrifuge tube. After vigorously shaking the mixture, it was centrifuged at 3,000 rpm for 5 min. Aliquots (100 μL) were removed from the two phases and the radioactivity was measured in a γ-counter, 1282 Compugamma CS (LKB, Wallac, Turku, Finland).

On analysis of the reaction mixture by HPLC, the retention time of the radiolabeled compound was slightly longer than the corresponding free ligand. The specific radioactivity of purified [$^{68}$Ga]SRV27 and [$^{68}$Ga]SRV100 was between 3.0 and 6.0 MBq/nmol. The log $P_{octanol/water}$ values for [$^{68}$Ga]SRV27 and [$^{68}$Ga]SRV100 were approximately −3.9 as determined by the shake-flask method (Antunes et al., Bioconjug Chem, vol. 18, pp. 84-92, 2007). However, using an HPLC method, we found that the HPLC retention times for SRV100 (28 min) and [$^{69/71}$Ga]SRV100 (32 min) were longer than for SRV27 (19 min) and [$^{69/71}$Ga]SRV27 (24 min). It is evident that SRV100 and the corresponding gallium compound were more lipophilic than SRV27 and its gallium-labeled analog, which is reasonable in light of the presence of two phenylalanine residues in the long linker of SRV100, while SRV27 has only one lysine residue protected as the benzyl ester.

Cell Binding Assay

Ki values for SRV27, [$^{69,71}$Ga]SRV27, SRV100 and [$^{69,71}$Ga]SRV100 were determined using a competitive N-acetyl aspartyl glutamate (NAAG) fluorescence cell binding assay adapted from the literature (Kozikowski et al., *J Med Chem*, vol. 47, pp. 1729-1738, 2004). All compounds were found to be strong inhibitors of PSMA. Compounds SRV27 and [$^{69,71}$Ga]SRV27 had inhibitory capacities of 2.9 nM and 29 nM, respectively. For SRV100 and [$^{69,71}$Ga]SRV100, values were 1.23 nM and 0.44 nM, respectively.

Ex Vivo Biodistribution

PSMA+ PC-3 PIP and PSMA− PC-3 flu xenograft-bearing SCID mice were injected via the tail vein with 30 μCi (1.1 MBq) of [$^{68}$Ga]SRV27 or [$^{68}$Ga]SRV100. In case each four mice were sacrificed by cervical dislocation at 30, 60, 120, 180 min p.i. For [$^{68}$Ga]SRV27 and at 5, 60, 120, 180 min p.i. for [$^{68}$Ga]SRV100. The heart, lungs, liver, stomach, pancreas, spleen, fat, kidney, muscle, small and large intestines, urinary bladder, and PC-3 PIP and flu tumors were quickly removed. A 0.1 mL sample of blood was also collected. Each organ was weighed, and the tissue radioactivity was measured with an automated gamma counter (1282 Compugamma CS, Pharmacia/LKB Nuclear, Inc., Gaithersburg, Md.). The % ID/g was calculated by comparison with samples of a standard dilution of the initial dose. All measurements were corrected for decay.

Compound [$^{68}$Ga]SRV27 was assessed for its pharmacokinetics ex vivo in severe-combined immunodeficient (SCID) mice bearing both PSMA+ PC3-PIP and PSMA− PC3-flu xenografts (Chang et al., *Cancer Res*, vol. 59, pp. 3192-3198, 1999). Table 1 shows the percent injected dose per gram (% ID/g) of radiotracer in selected organs for [$^{68}$Ga]SRV27.

TABLE 1

Ex vivo tissue biodistribution of [$^{68}$Ga]SRV27

| Tissue | 30 min | 60 min | 120 min | 180 min |
|---|---|---|---|---|
| blood | 2.20 ± 0.90 | 1.93 ± 0.70 | 0.80 ± 0.30 | 0.62 ± 0.34 |
| heart | 0.70 ± 0.13 | 0.50 ± 0.08 | 0.21 ± 0.08 | 0.20 ± 0.02 |
| liver | 0.84 ± 0.24 | 0.83 ± 0.10 | 0.42 ± .0.07 | 0.50 ± 0.03 |
| stomach | 0.73 ± 0.13 | 0.75 ± 0.32 | 0.24 ± 0.07 | 0.24 ± 0.05 |
| spleen | 4.90 ± 1.10 | 3.35 ± 1.20 | 0.43 ± 0.19 | 0.32 ± 0.13 |
| kidney | 97.19 ± 16.07 | 64.68 ± 4.10 | 5.35 ± 2.12 | 2.13 ± 0.11 |
| muscle | 0.46 ± 0.16 | 0.25 ± 0.07 | 0.08 ± 0.04 | 0.05 ± 0.01 |
| small intestine | 0.79 ± 0.12 | 0.70 ± 0.34 | 0.26 ± 0.11 | 0.34 ± 0.20 |
| large intestine | 0.77 ± 0.14 | 0.95 ± 0.53 | 0.34 ± 0.10 | 0.46 ± 0.10 |
| bladder | 8.96 ± 5.30 | 25.29 ± 8.63 | 2.70 ± 4.02 | 5.39 ± 2.98 |
| PC-3 PIP | 3.78 ± 0.90 | 3.32 ± 0.33 | 1.31 ± 0.06 | 1.10 ± 0.19 |
| PC-3 flu | 0.82 ± 0.20 | 0.67 ± 0.08 | 0.41 ± 0.09 | 0.39 ± 0.02 |
| PIP: flu | 4.61 | 4.93 | 3.24 | 2.77 |
| PIP: muscle | 8.30 | 13.13 | 17.40 | 20.37 |
| flu: muscle | 1.80 | 2.67 | 5.37 | 7.34 |

Compound [$^{68}$Ga]SRV27 showed clear PSMA-dependent binding in PSMA+ PC3 PIP xenografts, reaching a maximum uptake of 3.78±0.90 (SEM) % ID/g at 30 min post-injection (p.i.). The blood, spleen and kidney displayed highest uptake at 30 min. By 60 min, the urinary bladder showed highest uptake, however, this uptake represents excretion at all time points. The high values noted in kidney are partially due to high expression of PSMA within proximal renal tubules (Silver et al., *Clin Cancer Res*, vol. 3, pp. 81-85, 197; Slusher et al., *J Comp Neurol*, vol. 315, pp. 271-229, 1992). Rapid clearance from the kidneys was demonstrated, decreasing from 97.19±16.07% ID/g at 30 min to 2.31±0.11% ID/g at 3 h. The radioactivity in the PSMA+ PIP tumor cleared more slowly, from its aforementioned value at 30 min to 1.08±0.19% ID/g at 3 h.

Compound [$^{68}$Ga]SRV100 was also investigated for its pharmacokinetic characteristics in tumor bearing mice at 5 min, 1 h, 2 h and 3 h p.i. Table 2 shows the % ID/g of radiotracer in selected organs for [$^{68}$Ga]SRV100.

TABLE 2

Ex vivo tissue biodistribution of [$^{68}$Ga]SRV100

| Tissue | 5 min | 60 min | 120 min | 180 min |
|---|---|---|---|---|
| blood | 6.28 ± 0.08 | 0.41 ± 0.05 | 0.15 ± 0.07 | 0.13 ± 0.01 |
| heart | 2.01 ± 0.24 | 0.19 ± 0.07 | 0.05 ± 0.03 | 0.03 ± 0.01 |
| lung | 4.59 ± 0.68 | 0.74 ± 0.54 | 0.20 ± 0.05 | 0.14 ± 0.03 |
| liver | 1.57 ± 0.16 | 0.24 ± 0.09 | 0.19 ± 0.03 | 0.14 ± 0.02 |
| stomach | 2.38 ± 0.35 | 0.38 ± 0.16 | 0.18 ± 0.02 | 0.04 ± 0.02 |
| pancreas | 1.52 ± 0.19 | 0.25 ± 0.14 | 0.08 ± 0.03 | 0.04 ± 0.02 |
| spleen | 5.17 ± 2.22 | 2.43 ± 1.07 | 0.78 ± 0.15 | 0.34 ± 0.09 |
| fat | 1.03 ± 0.02 | 0.40 ± 0.04 | 0.08 ± 0.02 | 0.02 ± 0.01 |
| kidney | 64.75 ± 12.00 | 26.57 ± 10.93 | 12.25 ± 1.79 | 10.04 ± 1.22 |
| muscle | 1.58 ± 0.33 | 0.12 ± 0.08 | 0.03 ± 0.02 | 0.00 ± 0.01 |
| small intestine | 2.04 ± 0.25 | 0.23 ± 0.05 | 0.09 ± 0.04 | 0.06 ± 0.03 |
| large intestine | 2.02 ± 0.49 | 0.50 ± 0.70 | 0.12 ± 0.03 | 0.12 ± 0.03 |
| bladder | 5.97 ± 1.50 | 7.65 ± 3.34 | 1.41 ± 1.17 | 0.75 ± 0.54 |
| PC-3 PIP | 6.61 ± 0.55 | 2.80 ± 1.32 | 3.29 ± 0.77 | 1.80 ± 0.16 |
| PC-3 flu | 2.63 ± 0.51 | 0.16 ± 0.08 | 0.18 ± 0.03 | 0.12 ± 0.03 |
| PIP: flu | 2.50 | 17.30 | 18.28 | 15.20 |
| Pip: muscle | 4.17 | 23.27 | 122.13 | 436.29 |
| flu: muscle | 1.67 | 1.34 | 6.68 | 28.70 |

As for [$^{68}$Ga]SRV27, [$^{68}$Ga]SRV100 showed PSMA-dependent tumor uptake. After a peak, flow-related, uptake at 5 min p.i. of 6.61±0.55%, [$^{68}$Ga]SRV100 demonstrated a 2 h tumor uptake value of 3.29±0.77%, which dropped to 1.80±0.16% at 3 h. Uptake in blood was high at 5 min and rapidly washed out within 1 h. Non-target organs such as kidney, spleen and lung showed high uptake at 5 min and rapidly washed out with time. With the exception of the kidneys and spleen, clearance from blood and normal organs was faster for [$^{68}$Ga]SRV100 than for [$^{68}$Ga]SRV27. Again, high kidney uptake is associated with high expression of PSMA within proximal renal tubules (Silver et al., *Clin Cancer Res*, vol. 3, pp. 81-85, 197; Slusher et al., *J Comp Neurol*, vol. 315, pp. 271-229, 1992). Similar to [$^{68}$Ga]SRV27, [$^{68}$Ga]SRV100 demonstrated faster clearance of radioactivity from kidney than from the PSMA+ tumor. However, the rate of clearance from kidney for [$^{68}$Ga]SRV100 was much slower than for [$^{68}$Ga]SRV27, i.e., 65±12% at 5 min p.i. and 10.04±1.22% at 3 h.

Small Animal PET Imaging

A single SCID mouse implanted with a PSMA+ LNCaP xenograft was injected intravenously with 0.2 mCi (7.4 MBq) of [$^{68}$Ga]SRV27 in 200 μL 0.9% NaCl. At 0.5 h p.i., the mouse was anesthetized with 3% isoflurane in oxygen for induction and maintained under 1.5% isoflurane in oxygen at a flow rate of 0.8 L/min. The mouse was positioned in the prone position on the gantry of a GE eXplore VISTA small animal PET scanner (GE Healthcare, Milwaukee, Wis.). Image acquisition was performed using the following protocol: The images were acquired as a pseudodynamic scan, i.e., a sequence of successive whole-body images were acquired in three bed positions for a total of 120 min. The dwell time at each position was 5 min, such that a given bed position (or mouse organ) was revisited every 15 min. An energy window of 250-700 keV was used. Images were reconstructed using the FORE/2D-OSEM method (two iterations, 16 subsets) and included correction for radioactive decay, scanner dead time, and scattered radiation. After PET imaging, the mobile mouse holder was placed on the gantry of an X—SPECT (Gamma Medica Ideas, Northridge, Calif.) small animal imaging device to acquire the corresponding CT. Animals were scanned over a 4.6 cm field-of-view using a 600 μA, 50 kV beam. The PET and CT data were then co-registered using Amira 5.2.0 software (Visage Imaging Inc., Carlsbad, Calif.).

Imaging studies of [$^{68}$Ga]SRV100 and blocking studies of [$^{68}$Ga]SRV27 were carried out on PSMA+ PC-3 PIP and PSMA− PC-3 flu xenograft-bearing SCID mice or PSMA+ PC-3 PIP (25.9 MBq in 100 μL NaCl) xenograft-bearing SCID mice. At 30 min, 1 h and 2 h p.i. the mice were anesthetized and whole-body images were obtained using the PET scanner as mentioned above, in two bed positions, 15 min at each position for a total of 30 min using the same energy window. Images were reconstructed and co-registered with the corresponding CT images using the same methods as described above.

Figure 2:
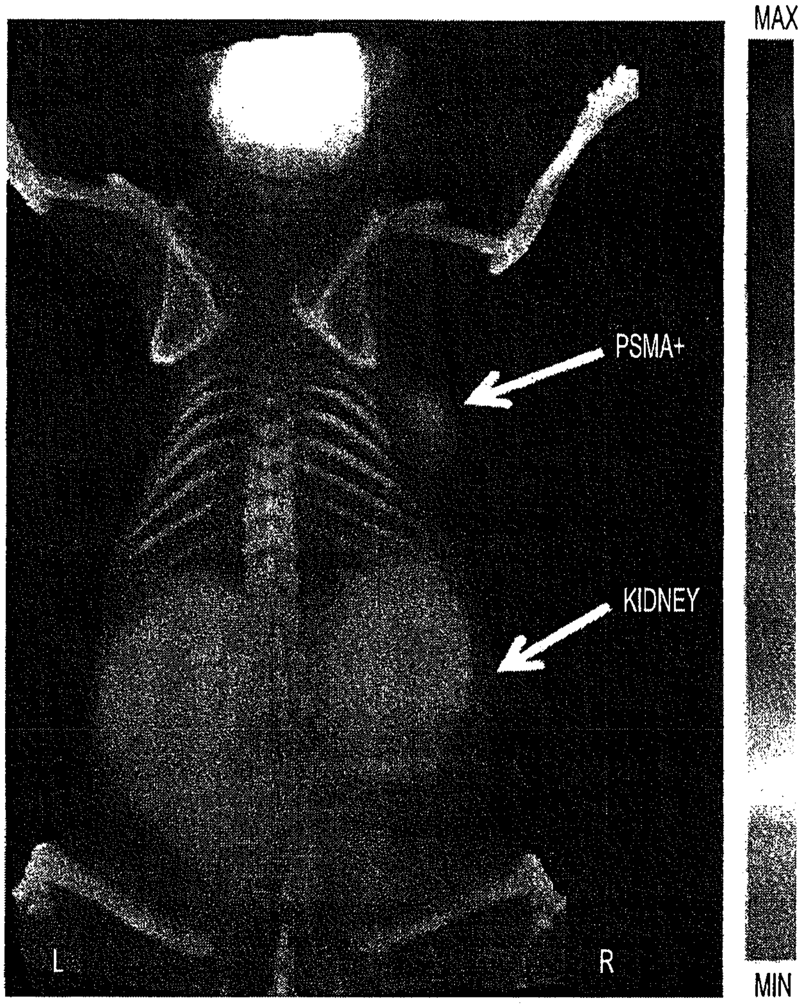
FIG. 2. GE eXplore VISTA pseudodynamic PET image (co-registered with the corresponding CT image) of a PSMA+ LNCaP tumor-bearing mouse injected intravenously with 0.2 mCi (7.4 MBq) of exemplary compound [$^{68}$Ga]SRV27.
Figure 3:
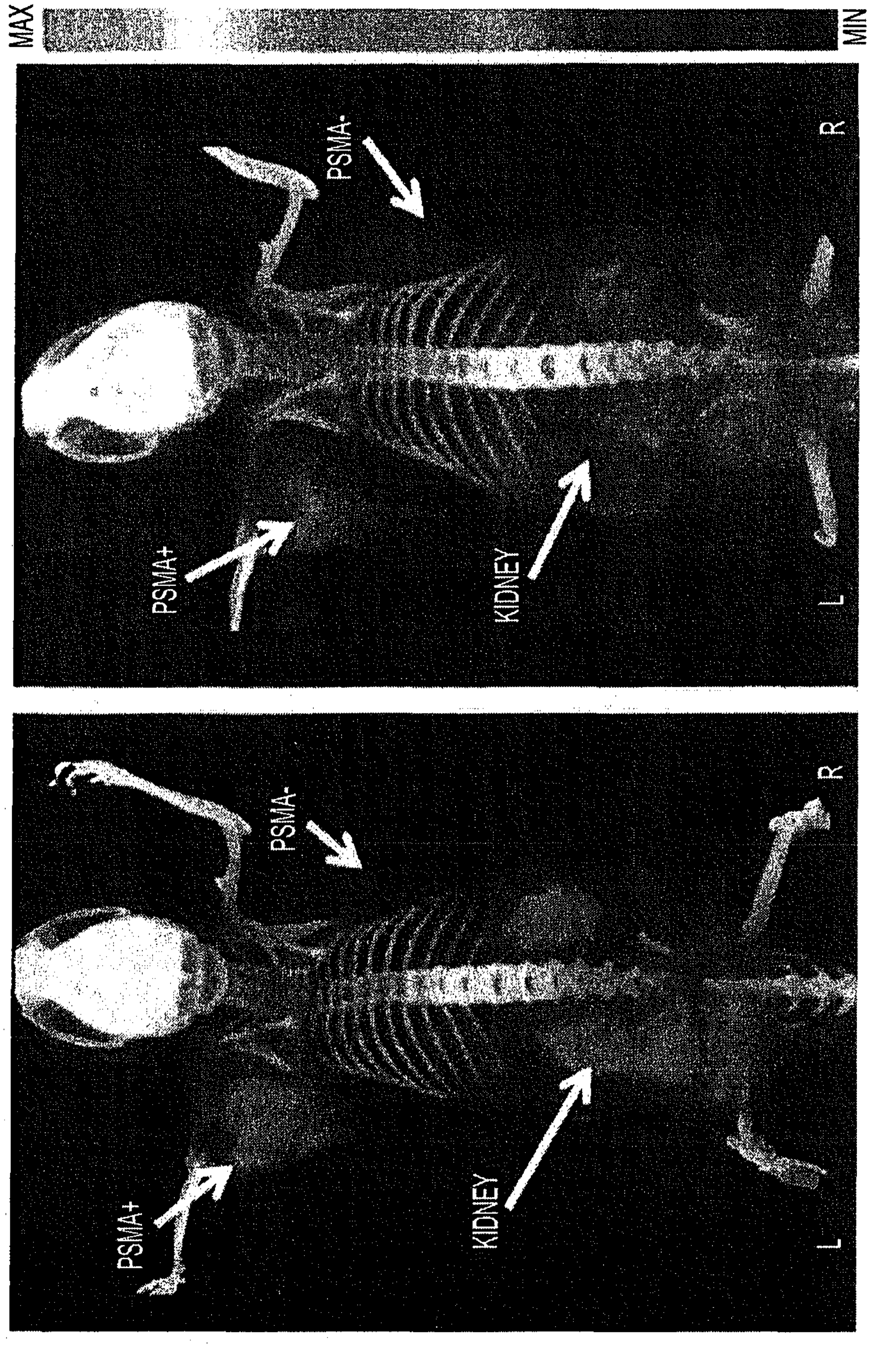
FIG. 3. GE eXplore VISTA PET image (co-registered with the corresponding CT image) of a PSMA+ PIP and PSMA− flu tumor-bearing mouse injected intravenously with 0.2 mCi (7.4 MBq) of exemplary compound [$^{68}$Ga]SRV100.

FIGS. 2 and 3 demonstrate the high target selectivity of [$^{68}$Ga]SRV27 and [$^{68}$Ga]SRV100 by delineating the PSMA+ tumors. Although a PSMA− control tumor was not included in FIG. 2, a separate blocking study was performed for [$^{68}$Ga]SRV27, in which an animal pre-treated with 50 mg/kg of the known PSMA-binding ligand, 2-(phosphonomethyl)pentanedioic acid (2-PMPA) (Jackson et al., *J Med Chem*, vol. 39, pp. 619-622, 1996), did not demonstrate PSMA+ tumor uptake, attesting to the binding specificity of this compound. The more quantitative, ex vivo studies of [$^{68}$Ga]SRV27 and [$^{68}$Ga]SRV100 further supported high PSMA target specificity, demonstrating target-to-nontarget (PIP/flu) ratios of approximately 5 and 18 at 1 h and 2 h p.i., respectively. One hour and 2 h PSMA+ tumor uptake values for these compounds, 3.32±0.33% and 3.29±0.77%, respectively, for

[$^{68}$Ga]SRV27 and [$^{68}$Ga]SRV100, are comparable to other radiometallated PSMA inhibitors (Banerjee et al., *J Med Chem*, vol. 51, pp. 4504-4517, 2008). As shown in FIGS. 2 and 3 those values are sufficient for clear tumor imaging. Notably, PIP tumors contain about one order of magnitude lower PSMA than LNCaP tumors (data not shown), which are often employed to assess for binding specificity of PSMA-targeting agents. PIP/flu is the preferred comparison as both are derived from PC-3 cells, providing a more controlled study.

Intense radiotracer uptake was seen only in the kidneys and tumor for both [$^{68}$Ga]SRV27 (FIG. 2) and [$^{68}$Ga]SRV100 (FIG. 3). As noted above for the ex vivo study, the intense renal uptake was partially due to specific binding of the radiotracer to proximal renal tubules (Silver et al., *Clin Cancer Res*, vol. 3, pp. 81-85, 197; Slusher et al., *J Comp Neurol*, vol. 315, pp. 271-229, 1992) as well as to excretion of this hydrophilic compound. Apart from the kidneys, only the PSMA+ tumor demonstrated significant radiotracer uptake.

Discussion

Because of its demonstrated clinical utility and the appearance of dual modality (PET/computed tomography (CT)) systems, clinical PET imaging has been accelerating worldwide and may soon become the dominant technique in nuclear medicine. PET isotopes tend to be short-lived and enable synthesis of "physiologic" radiotracers, namely, those that incorporate $^{15}$O, $^{13}$N or $^{11}$C, enabling precise conformity to the tracer principle. Being essentially isosteric to H, $^{18}$F enables nearly tracer-level studies, with important caveats, particularly for [$^{18}$F]fluorodeoxyglucose (FDG), which is by far the most commonly used radiopharmaceutical for PET. But, in part because FDG does not accumulate well within many tumor types, including prostate cancer, there has been a re-emergence in the development of radiometallated peptides, often employing $^{99m}$Tc, that target G-protein coupled receptors. Gallium-68 provides a link between PET and single photon emission computed tomography (SPECT) since metal chelating methodology needed for $^{99m}$Tc can also be applied to $^{68}$Ga. A further analogy is the convenience of use of a $^{68}$Ge/$^{68}$Ga generator (PET), as with $^{99}$Mo/$^{99m}$Tc (SPECT), to provide readily available isotope, with no need for an in-house cyclotron. Although $^{18}$F-labeled, low molecular weight PSMA inhibitors have shown promise in preclinical imaging studies (Mease et al., *Clin Cancer Res*, vol. 14, pp. 3036-3043, 2008; Lapi et al., *J Nucl Med*, vol. 50, pp. 2042-2048, 2009), the availability of generator-produced $^{68}$Ga and the extension to PET from our published $^{99m}$Tc-labeled series of PSMA-binding radiometallated imaging agents (Banerjee et al., J Med Chem, vol. 51, pp. 4504-4517, 2008) provided the rationale for this study.

Example 3

Compound SRV27 and SRV100 were prepared as described in Example 2. In-111 labeling was generally performed by treatment of SRV27 or SRV100 or SRV73 with $^{111}$ $InCl_3$, in 200 mM aqueous NaOAc ~60° C. for 30 minutes. Specifically, for SRV27, 60 μl of SRV27 (2 mg/mL, sodium acetate) was combined with 100 μl sodium acetate and 3mCi $^{111}$ $InCl_3$ in a 1.5 ml appendorf tube and left at for 60° C. for 30 min. The radiolabled product was diluted with 800 μl water and purified by HPLC. Radiolabeling yield is 1.7 mCi (~57%) and radiochemical purity was >99.9%

SRV73

Compound SRV73 was prepared by the method outlined in the scheme below. Compound SRV73 is a bimodal compound having a fluorescent dye moiety and a metal chelating moiety

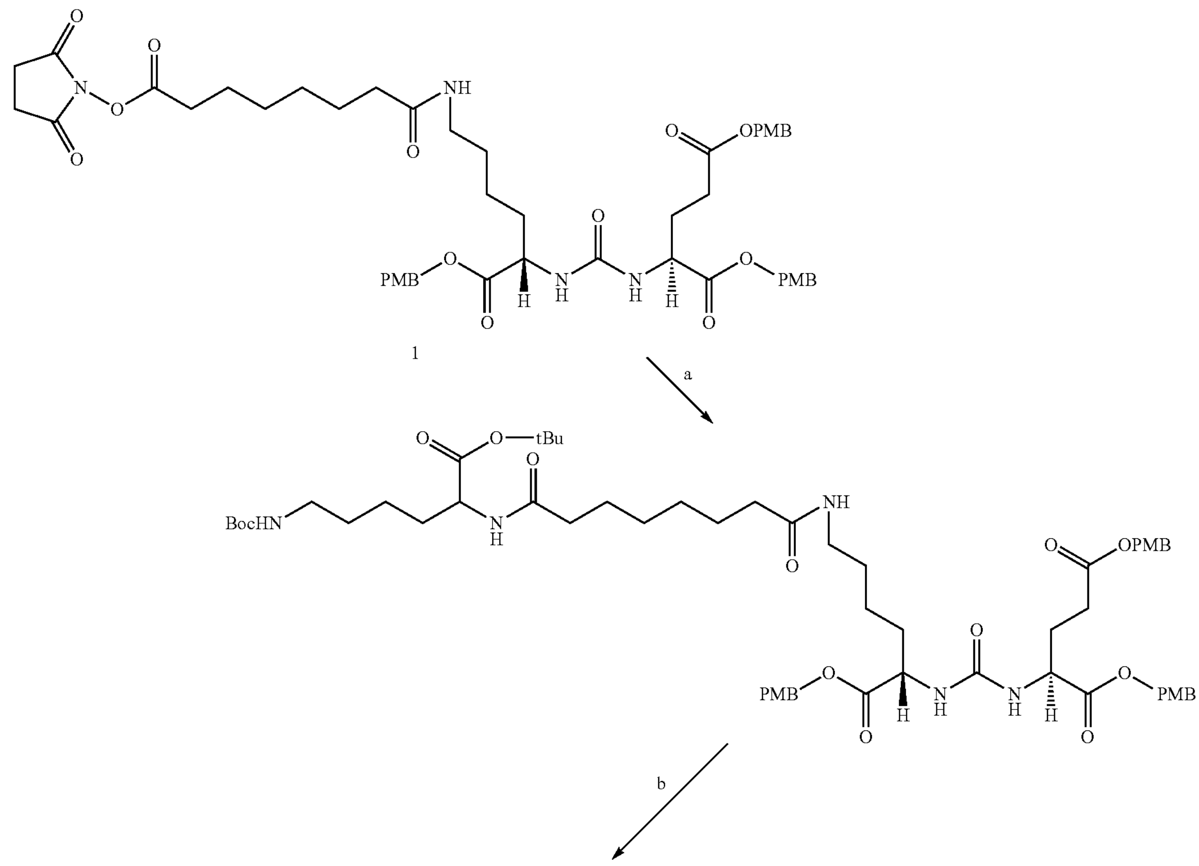

-continued

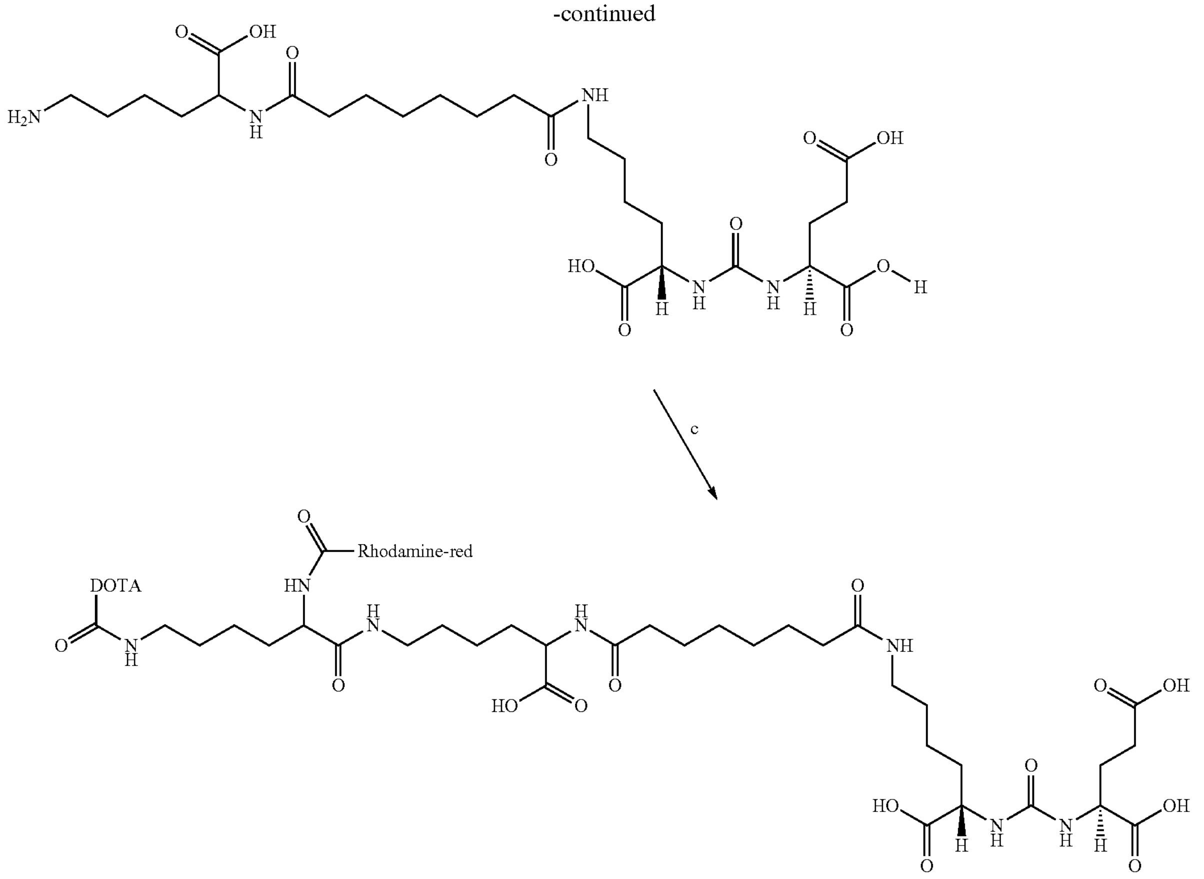

SRV73, Ki(17 nM)

a. (i) H-Lys-(Boc)—O—tBu, DMF, TEA;
b. (i) TFA/$CH_2Cl_2$;
c. (i) Fmoc-Lys(Boc)—OSu, TEA, DMF; (ii) $CH_2Cl_2$/TFA; (iii) DOTA—NHS, TEA, DMF; (iv) 20% piperidine/DMF; (v) Rhodamine-red-X, TEA, DMF;

Small Animal PET Imaging

SPECT imaging experiments for [$^{111}$In]SRV27, [$^{111}$In]SRV100 and [$^{111}$In]SRV73 were performed using the same general procedure described for [$^{99m}$Tc]SRV32 described in Example 1.

Figure 5:
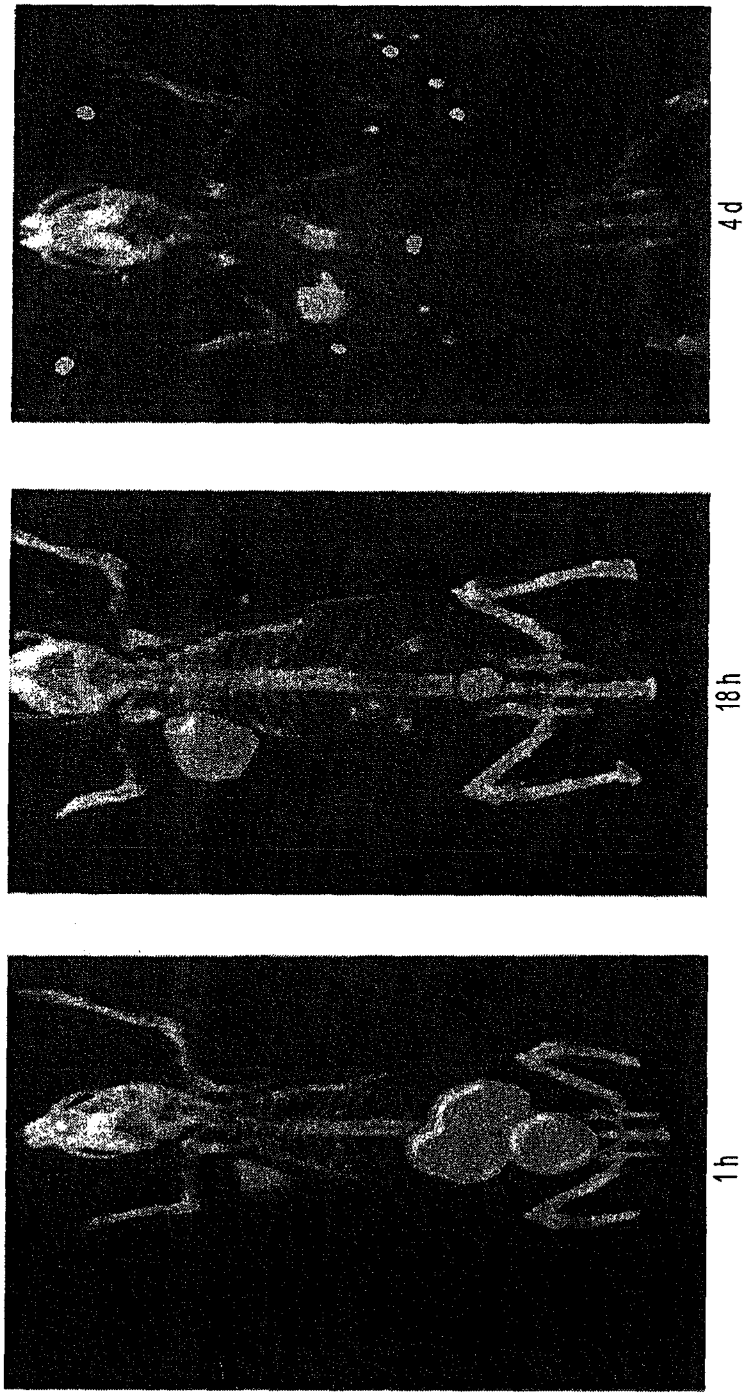
FIG. 5 shows SPECT-CT images of a PSMA+ PC-3 PIP tumor-bearing mouse injected intravenously with exemplary compound [$^{111}$In]SRV27.

SPECT-CT imaging experiment of compound [$^{111}$In]SRV27 (FIG. 5) illustrated clear PSMA-dependent binding in PSMA+ PC3 PIP xenografts within 1 h post injection. The high values noted in kidney are partially due to high expression of PSMA within proximal renal tubules (Silver et al., Clin Cancer Res, vol. 3, pp. 81-85, 197; Slusher et al., J Comp Neurol, vol. 315, pp. 271-229, 1992). Rapid clearance from the kidneys was observed while the activity retained in PSMA+ tumor even after four days post injection.

Figure 6:
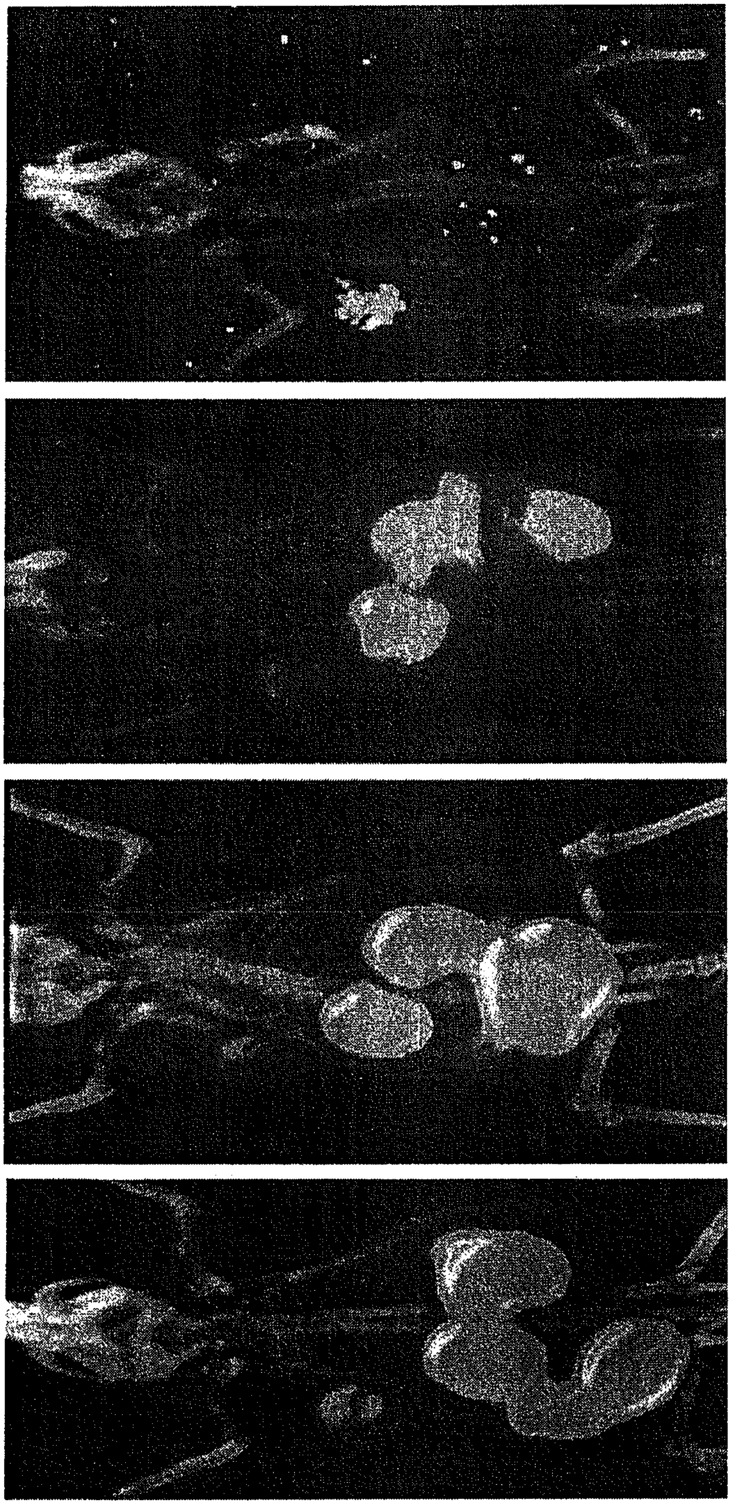
FIG. 6 shows SPECT-CT images of a PSMA+ PC-3 PIP tumor-bearing mouse injected intravenously with exemplary compound [$^{111}$In]SRV100.

SPECT-CT imaging experiment of compound [$^{111}$In]SRV100 (FIG. 6) demonstrated similar clear PSMA-dependent binding in PSMA+ PC3 PIP xenografts within 2 h post injection. The high values noted in kidney are partially due to high expression of PSMA within proximal renal tubules (Silver et al., Clin Cancer Res, vol. 3, pp. 81-85, 197; Slusher et al., J Comp Neurol, vol. 315, pp. 271-229, 1992). Rapid clearance from the kidneys was observed while the activity retained in PSMA+ tumor even after four days post injection. The longer tumor activity retention for [$^{111}$In]SRV27 and [$^{111}$In]SRV100 might be useful Y-90/Lu-177 based radiotherapeutic application.

Figure 7:
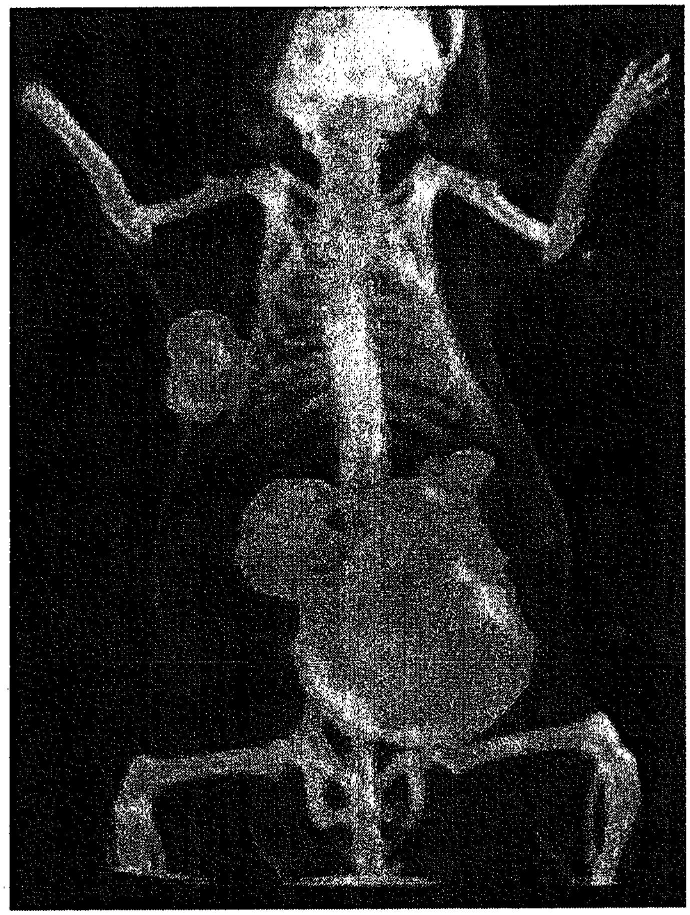
FIG. 7 shows SPECT-CT images of a PSMA+ PC-3 PIP tumor-bearing mouse injected intravenously with exemplary dual modality compound [$^{111}$In]SRV73.

FIG. 7 demonstrates clear tumor uptake for [$^{111}$In]SRV73 at 7 h post injection. This is significant since after attaching a bulky fluorescent dye, rhodamine, the compound retains its PSMA binding activity. This is an example of dual modality application for this class of compounds.

Example 4

SRVI34

2-{3-[1-Carboxy-5-(7-{5-carboxy-5-[3-phenyl-2-(3-phenyl-2-{2-[2-(2-tritylsulfanyl-acetylamino)-acetylamino]-acetylamino}-propionylamino)-propionylamino]-pentylcarbamoyl}-heptanoylamino)-pentyl]-ureido}-pentanedioic acid (SRVI34)

SRVI34 was prepared according to the scheme below. Lys(Boc)-Wang resin (100 mg, 0.43 mM) was allowed to swell with $CH_2Cl_2$ (3 mL) followed by DMF (3 mL). A solution of 20% piperidine in DMF (3x3 mL) was added to the resin that was then shaken gently on a mechanical shaker for 30 min at ambient temperature. The resin was washed with DMF (3x3 mL) and $CH_2Cl_2$ (3x3 mL). Formation of free amine was assessed by the Kaiser test. After swelling the resin in DMF, a solution of Fmoc-Phe-OH (3 eq), HBTU (3 eq), HOBt (3 eq), and DIPEA (4.0 eq) in DMF was added and gently shaken for 2 h. The resin was then washed with DMF (3×3 mL) and $CH_2Cl_2$ (3×3 mL). The coupling efficiency was assessed by the Kaiser Test. That aforementioned sequence was repeated for four more coupling steps with Fmoc-Phe-OH, Fmoc-Gly-OH, Fmoc-Gly-OH and S-trityl mercaptoacetic acid. Finally the product was cleaved from the resin using TFA:$CH_2Cl_2$ (1:1) and concentrated under vacuum to produce the free amine (SRVI32). The concentrated product was purified by using a $C_{18}$ SepPak Vac 2 g column. The product was eluted with a solution 70/30 water/acetonitrile (0.1% TFA in each). ESIMS: [M+1]+. Lyophilized SRVI32 (10 mg, 12 μmol in 2 mL DMF) was added to the urea (compound 1 described in Example 2) (20 mg, 21.4 μmol in 1 mL DMF) followed by TEA (214 μmol, 30 μL) and then stirred at 25° C. for 16 h. The residue was washed 2×5 mL $CH_2Cl_2$ to remove impurities. The colorless solid residue thus obtained was purified by a $C_{18}$ SepPak Vac 2 g column using an eluent of 70/30 water/acetonitrile (0.1% TFA in each). The product was further purified using preparative RP-HPLC by Method 1, retention time 17 min. Yield: ~30%. ESMS m/Z: 1328 $[M+H]^+$, $^1H$ NMR ($D_2O/CD_3CN$ (1:1) δ: 7.98 (m, 5H), 7.90-7.76 (m, 18H), 7.66 (m, 2H), 5.11 (m, 1H), 4.82-4.72 (m, 3H), 4.28 (m, 2H), 4.16 (m, 2H), 3.68 (m, 5H), 3.49-3.32 (m, 2H), 3.00 (m, 2H), 2.69 (m, 4H), 2.64-1.74 (m, 26H).

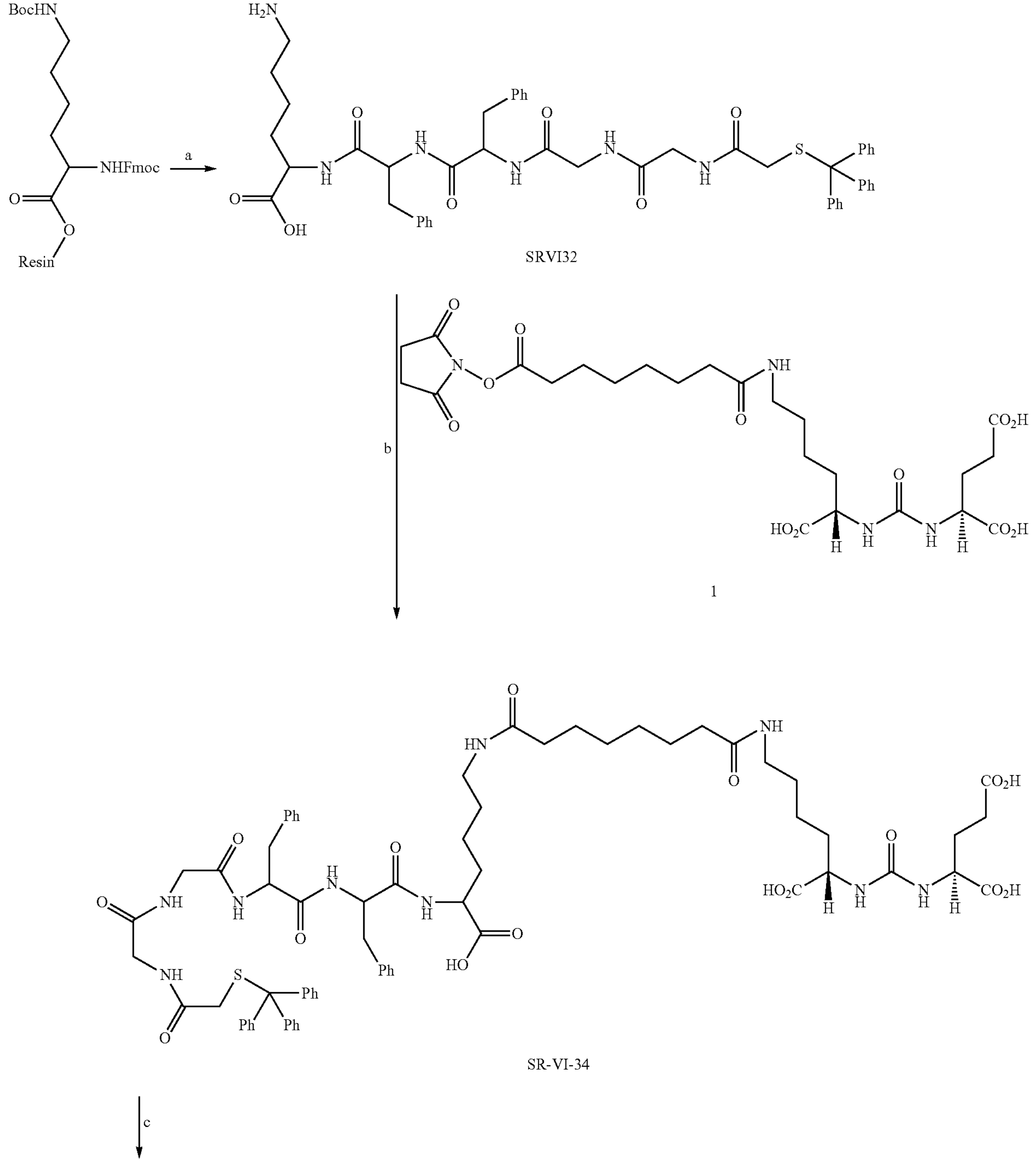

SRVI32

1

SR-VI-34

-continued

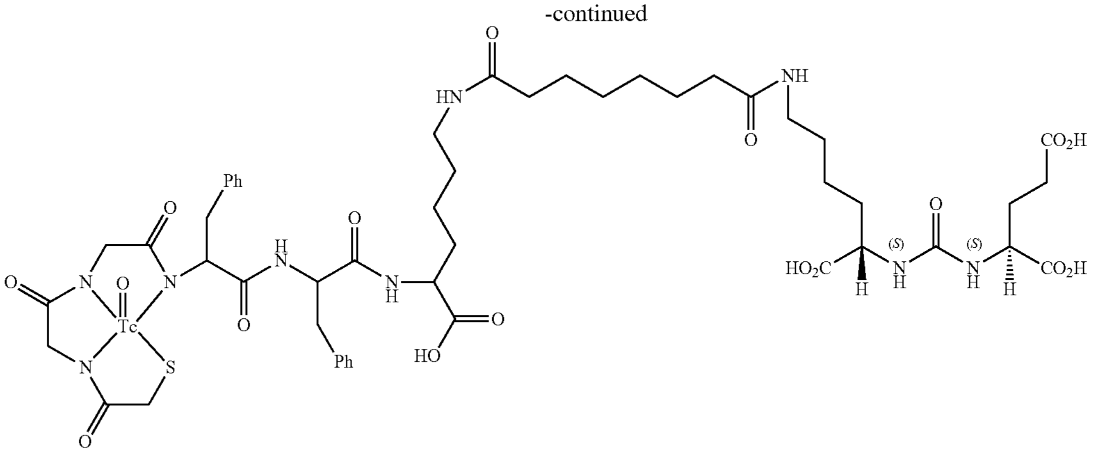

a. (i) 20% piperdine/DMF; (ii) Fmoc-Phe-OH, HOBt, HBTU, DIEA; (iii) 20% piperdine/DMF; (iv) Fmoc-Phe-OH, HOBt, HBTU, DIEA; (v) 20% piperidine/DMF; (vi)Fmoc-Gly-OH, HOBt, HBTU, DIEA; (vii) 20% piperidine/DMF; (viii)Fmoc-Gly-OH, HOBt, HBTU, DIEA; (ix) 20% piperidine/DMF; (x) (S—Ph3)—CH2CO2H, HOBt, HBTU, DIEA; (xi) TFA/$CH^2Cl^2$; b. TEA, DMF; c. $TcO4^-$, SnCl2, sodium ascorbate, Na-tartarate, NH4OAc, pH 7.5.

Radiolabeling with Tc-99m:

Radiolabeling was performed following a literature procedure (Wang et al., Nature Protocols, vol. 1, pp. 1477-1480, 2006). Briefly, 1 mg (75.3 mmol) of compound SRVI34 was dissolved in 1 ml of 0.5 M ammonium acetate buffer at pH 8. Disodium tartarate dihydrate was dissolved in the labelling buffer of 0.5 M ammonium acetate (pH 8) to a concentration of 50 mg/ml. Ascorbic acid-HCl solution was prepared by dissolving ascorbic acid in 10 mM HCl to a concentration of 1.0 mg/ml. A solution of SRVI34 (80 µl) was combined to a solution of 45 µl 0.25 M ammonium acetate, 15 µl tartarate buffer, followed by 5 µl of the freshly prepared 4 mg/ml $SnCl_2.2H_2O$ solution in the ascorbate-HCl solution. The final pH will be about 8-8.5. After vortexing, was added 20 mCi of $^{99m}$Tc-pertechnetate in 200 µl saline and was heated the solution at 90-100° C. for 20 min. Reaction mixture was cooled, diluted 850 µl of water and purified by HPLC using a Phenomenex $C_{18}$ Luna 10×250 $mm^2$ column on a Waters 600E Delta LC system with a Waters 486 tunable absorbance UV/Vis detector, both controlled by Empower software. HPLC solvent system, flow rate=4 ml/min, a gradient, 0-5 min, 80/20 water/acetonitrile (0.1% TFA in each solvent), 5-25 min 40/60 water/acetonitrile (0.1% TFA in each solvent) and 25-35 min 80/20 (0.1% TFA in each solvent) was used. Two radiolabeled products were found, called as [$^{99m}$Tc] SRVI34A (5.52 mCi) (retention time 17.5 min) and [$^{99m}$Tc] SRVI34B (6 mCi) (retention time 18.9 min) SRVI34A and SRVI32B are diastereomers, syn and anti-isomers with respect to the Tc═O group. Each product was neutralized with 50 µl of 1 M sodium bicarbonate and evaporated to dryness under vacuum. The obtained solid residues was dissolved in 200 µl saline and used for imaging and biodistribution studies.

Ex Vivo Biodistribution

PSMA+ PC-3 PIP and PSMA− PC-3 flu xenograft-bearing SCID mice were injected via the tail vein with 30 µCi [$^{99m}$Tc] SRVI34B. Four mice were sacrificed by cervical dislocation at 30, 60, 120, and 300 min p.i. The heart, lungs, liver, stomach, pancreas, spleen, fat, kidney, muscle, small and large intestines, urinary bladder, and PC-3 PIP and flu tumors were quickly removed. A 0.1 mL sample of blood was also collected. Each organ was weighed, and the tissue radioactivity was measured with an automated gamma counter (1282 Compugamma CS, Pharmacia/LKB Nuclear, Inc., Gaithersburg, Md.). The % ID/g was calculated by comparison with samples of a standard dilution of the initial dose. All measurements were corrected for decay.

Compound [$^{99m}$Tc]SRVI34B was assessed for its pharmacokinetics ex vivo in severe-combined immunodeficient (SCID) mice bearing both PSMA+ PC3-PIP and PSMA− PC3-flu xenografts (Chang et al., *Cancer Res*, vol. 59, pp. 3192-3198, 1999). Table 3 shows the percent injected dose per gram (% ID/g) of radiotracer in selected organs for [$^{99m}$Tc]SRVI34B.

TABLE 3

Biodistribution data for [$^{99m}$Tc]SRVI34B (n = 4)

| | 30 min | 60 min | 120 min | 300 min |
|---|---|---|---|---|
| Blood | 1.13 ± 1.06 | 0.69 ± 0.08 | 0.27 ± 0.09 | 0.23 ± 0.00 |
| heart | 1.11 ± 0.06 | 0.70 ± 0.16 | 0.61 ± 0.07 | 0.46 ± 0.05 |
| lung | 4.08 ± 0.31 | 4.84 ± 1.26 | 4.02 ± 0.73 | 2.79 ± 0.74 |
| liver | 1.55 ± 0.23 | 0.92 ± 0.37 | 0.50 ± 0.085 | 0.24 ± 0.09 |
| stomach | 0.79 ± 0.23 | 0.77 ± 0.17 | 0.54 ± 12 | 0.27 ± 0.08 |
| pancreas | 1.72 ± 0.74 | 1.42 ± 0.45 | 1.02 ± 0.29 | 0.94 ± 0.46 |
| spleen | 56.44 ± 16.49 | 64.24 ± 13.29 | 58.27 ± 18.26 | 24.49 ± 3.63 |
| fat | 2.18037 ± 0.50 | 2.13 ± 0.58 | 1.82 ± 0.37 | 0.99 ± 0.03 |
| kidney | 62.45 ± 1.63 | 96.38 ± 22.74 | 104.84 ± 19.03 | 116.14 ± 2.71 |
| muscle | 1.20 ± 0.12 | 0.74 ± 0.04 | 1.29 ± 1.31 | 0.45 ± 0.31 |
| small intestine | 1.03 ± 0.40 | 1.43 ± 0.66 | 0.79 ± 0.33 | 0.23 ± 0.12 |

TABLE 3-continued

| Biodistribution data for [$^{99m}$Tc]SRVI34B (n = 4) | | | | |
|---|---|---|---|---|
| | 30 min | 60 min | 120 min | 300 min |
| large intestine | 0.61 ± 0.03 | 0.63 ± 0.38 | 0.35 ± 0.12 | 1.30 ± 0.08 |
| bladder | 1.28 ± 0.25 | 2.07 ± 0.96 | 0.87 ± 0.33 | 0.51 ± 0.00 |
| PC-3 PIP | 6.11 ± 0.94 | 7.99 ± 2.26 | 6.96 ± 1.13 | 4.81 ± 0.66 |
| PC-3 flu | 0.98 ± 0.38 | 0.76 ± 0.51 | 0.50 ± 0.28 | 0.22 ± 0.11 |
| PIP: flu | 6.28 | 10.56 | 14.05 | 22.18 |

Small Animal SPECT-CT Imaging

Imaging experiments for [$^{99m}$Tc]SRVI34A and [$^{99m}$Tc]SRVI34B were done following the same procedures as was done for [$^{99m}$Tc]SRV32 (Example 1).

FIGS. 13, 14, 15, and 16 demonstrate the high target selectivity of [$^{99m}$Tc]SRVI34B by delineating the PSMA+ tumors. The compound [$^{99m}$Tc]SRVI34B exhibited high uptake in PSMA+ tumor and no uptake in PSMA− tumor. The tumor uptake remains high 4.88% ID/g even at 5 hr post inject (p.i.). However this compound showed very high kidney uptake 116% ID/g even at 5 hr p.i. In addition this compound showed high spleen uptake 24.5% ID/g at 5 hr p.i.

Example 5

General

All reagents and solvents were purchased from either Sigma-Aldrich (Milwaukee, Wis.) or Fisher Scientific (Pittsburgh, Pa.). 2-{3-[5-[7-(2,5-Dioxo-pyrrolidin-1-yloxycarbonyl)-heptanoylamino]-1-(4-methoxy-benzyloxycarbonyl)-pentyl]-ureido}-pentanedioic acid bis-(4-methoxy-benzyl) ester (1) was prepared according to (Banerjee et al., J. Med. Chem., vol. 51, pp. 4504-4517, 2008). H-Lys(Boc)-OBu.HCl was purchased from Chem-Impex International (Wood Dale, Ill.). The N-hydroxysuccinimide (NHS) ester of IRDye 800CW was purchased from LI-COR Biosciences (Lincoln, Nebr.). $^{1}$H NMR spectra were obtained on a Bruker Avance 400 mHz Spectrometer. ESI mass spectra were obtained on a Bruker Esquire 3000 plus system. Purification by high-performance liquid chromatography (HPLC) was performed on a Varian Prostar System (Varian Medical Systems, Palo Alto, Calif.).

YC-27

Compound YC-27 was prepared according the scheme shown below.

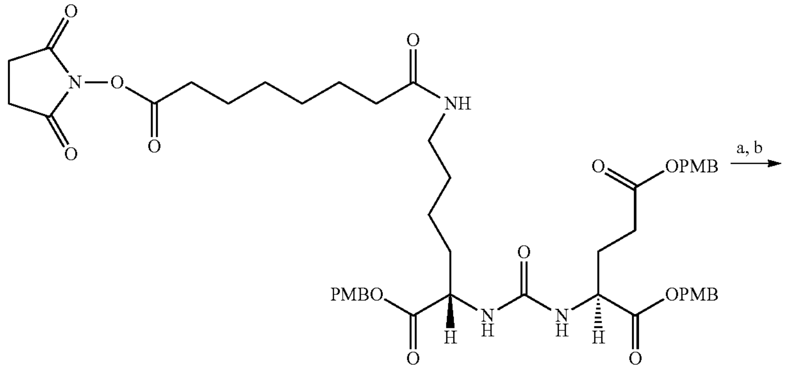

PMB = p-methoxybenzyl

1

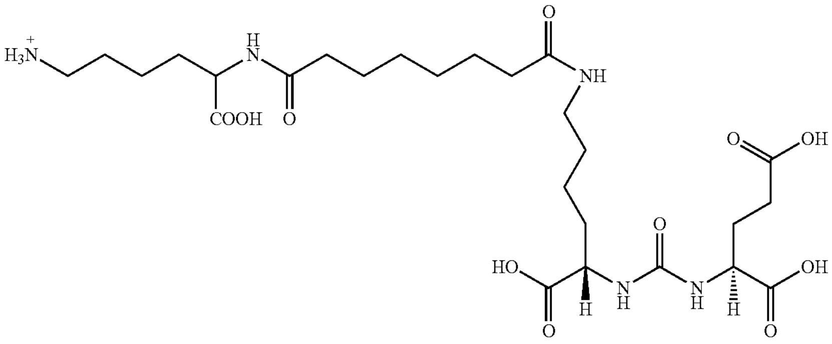

YC-VIII-24

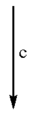

-continued

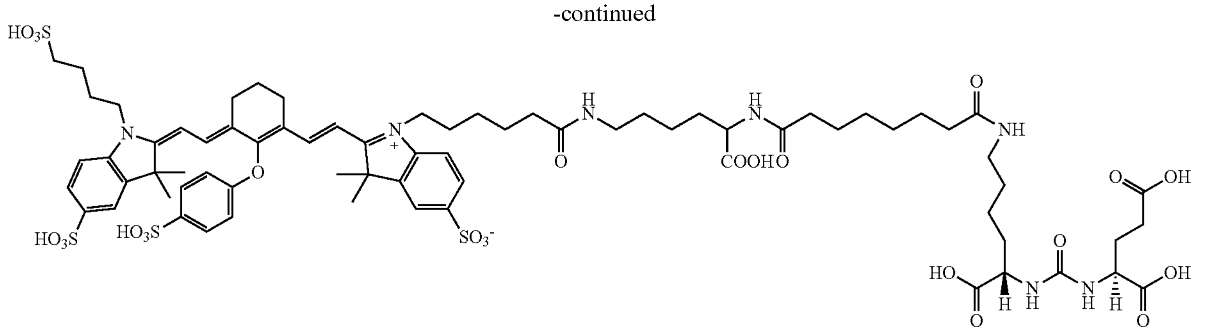

YC-27

(a) H-Lys(Boc)—OBu•HCl, $ET_3N$, $CH_2Cl_2$; (b) TFA:$CH_2Cl_2$ = 1:1;
(c) IRDye800CW-NHS, DIPEA, DMSO

Trifluoroacetate salt of 2-(3-{5-[7-(5-amino-1-carboxy-pentylcarbamoyl)-heptanoylamino]-1-carboxy-pentyl}-ureido)-pentanedioic acid (YC-VIII-24)

To a solution of 1 (0.065 g, 0.020 mmol) in $CH_2Cl_2$ (2 mL) was added triethylamine (0.040 mL, 0.285 mmol), followed by H-Lys(Boc)-OBu.HCl (0.028 g, 0.083 mmol). After stirring for 2 h at room temperature, the solvent was evaporated on a rotary evaporator. A solution of TFA/$CH_2Cl_2$ 1:1 (2 mL) was then added to the residue and stirred for 1 h at room temperature. The crude material was purified by HPLC (column, Econosphere C18, 10μ, 250×10 mm; retention time, 15 min; mobile phase, A=0.1% TFA in $H_2O$, B=0.1% TFA in $CH_3CN$; gradient, 0 min=5% B, 25 min=25% B; flow rate, 4 mL/min) to afford 0.032 g (66%) of YC-VIII-24. $^1H$ NMR (400 MHz, $D_2O$) δ 4.24-4.28 (m, 1H), 4.17-4.20 (m, 1H), 4.08-4.12 (m, 1H), 3.08-3.12 (m, 2H), 2.88-2.92 (m, 2H), 2.41-2.44 (m, 2H), 2.19-2.21 (m, 2H), 2.05-2.16 (m, 3H), 1.57-1.93 (m, 7H), 1.21-1.50 (m, 10H), 1.21 (m, 4H). ESI-Mass calcd for $C_{26}H_{46}N_5O_{11}$ $[M]^+$ 604.3, found 604.0.

YC-27.

To a solution of YC-VIII-24 (0.3 mg, 0.43 μmol) in DMSO (0.1 mL) was added N,N-diisopropylethylamine (0.002 mL, 11.4 μmol), followed by the NHS ester of IRDye 800CW (0.3 mg, 0.26 μmol). After stirring for YC-VIII-24 for 2 h at room temperature, the reaction mixture was purified by HPLC (column, Econosphere C18 5μ, 150×4.6 mm; retention time, 22 min, mobile phase, A=0.1% TFA in $H_2O$, B=0.1% TFA in $CH_3CN$; gradient, 0 min=0% B, 5 min=0% B, 45 min=100% B; flow rate, 1 mL/min) to afford 0.3 mg (72%) of YC-27. ESI-Mass calcd for $C_{72}H_{97}N_7O_{25}S_4$ $[M]^+$1587.5, found 794.3 $[M+H]^{2+}$, 1587.6 $[M]^+$.

Synthesis of precursor YC-VI-54

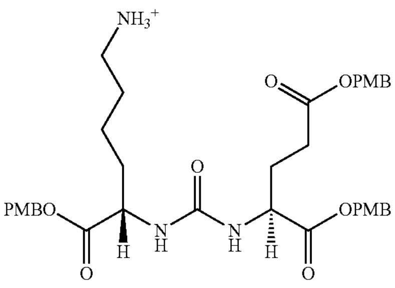

Lys-Urea-Glu

+

-continued

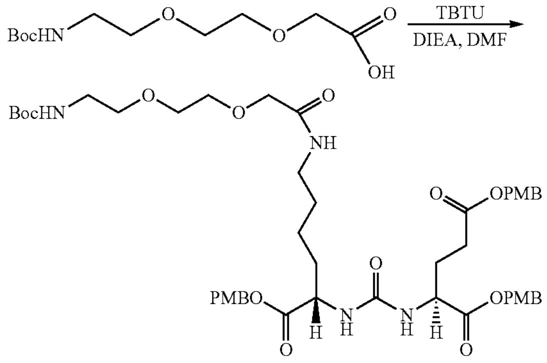

YC-VI-53

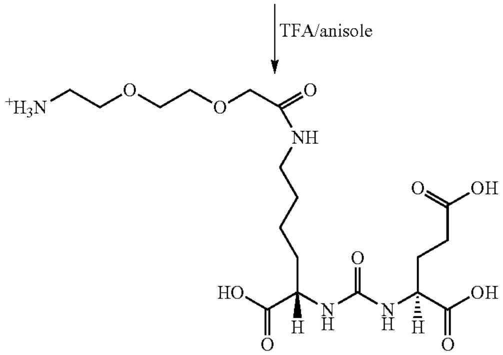

YC-VI-54

To a solution of Lys-Urea-Glu (0.103 g, 0.121 mmol, Banerjee et al *J. Med. Chem.*, vol. 51, pp. 4507-4517, 2008) in DMF (2 mL) was added Boc-NH-PEG-COOH (0.060 g, 0.135 mmol) and TBTU (0.040 g, 0.125 mmol), followed by N,N'-diisopropylethylamine (0.042 mL, 0.241 mmol). After stirring overnight at room temperature, the solvent was evaporated on a rotary evaporator. The crude material was purified by a silica column using methanol/methylene chloride (5:95) to afford 0.101 g (0.109 mmol, 90%) of YC-VI-53, which was dissolved in a solution of 3% anisole in TFA (1 mL). The mixture was reacted at room temperature for 10 min, then concentrated on a rotary evaporator. The crude material was purified by HPLC (Econosphere C18 10u, 250×10 mm, $H_2O$/$CH_3CN$/TFA (92/8/0.1), 4 mL/min, Compound YC-VI-54 eluting at 11 min) to afford 0.035 g (57%) of compound YC-VI-54. $^1$H NMR (400 MHz, $D_2O$) δ 4.17-4.21 (m, 1H), 4.10-4.13 (m, 1H), 4.00 (s, 2H), 3.67-3.71 (m, 6H), 3.14-3.20 (m, 4H), 2.43-2.46 (m, 2H), 2.08-2.13 (m, 1H), 1.87-1.93 (m, 1H), 1.76-1.79 (m, 1H), 1.63-1.67 (m, 1H), 1.45-1.50 (m, 2H), 1.33-1.40 (m, 2H). ESI-Mass calcd for $C_{18}H_{33}N_4O_{10}$ $[M]^+$465.2, found 465.2.

YC-VIII-11

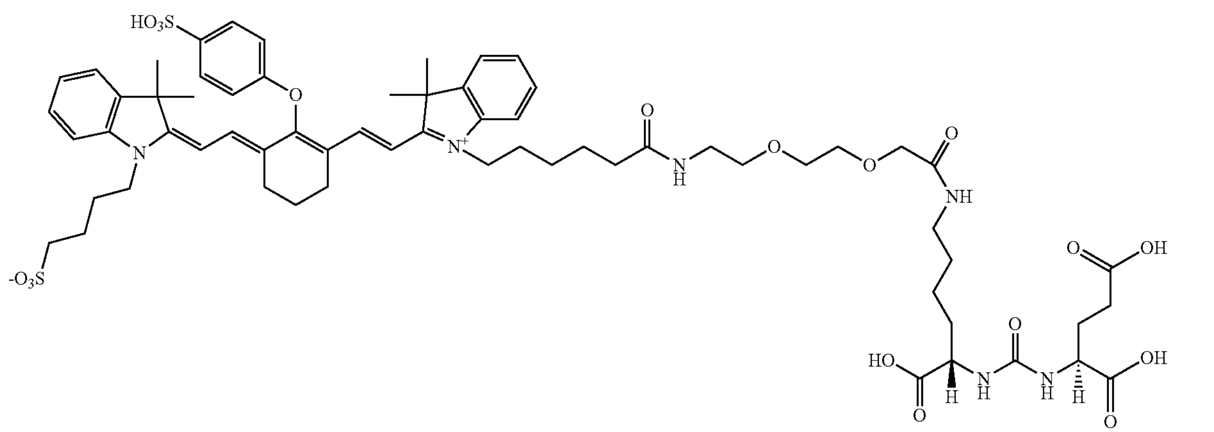

To a solution of compound YC-VI-54 (0.3 mg, 53 μmol) in DMSO (0.05 mL) was added N,N-diisopropylethylamine (0.002 mL, 11.4 μmol), followed by NHS ester of IRDye 800RS (0.2 mg, 0.21 μmol). After 2 hour at room temperature, the reaction mixture was purified by HPLC (column, Econosphere C18 5μ, 150×4.6 mm; retention time, 28 min; mobile phase, A=0.1% TFA in $H_2O$, B=0.1% TFA in $CH_3CN$; gradient, 0 mins=0% B, 5 mins=0% B, 45 mins=100% B; flow rate, 1 mL/min) to afford 0.2 mg (75%) of compound YC-VIII-11. ESI-Mass calcd for $C_{64}H_{84}N_6O_{18}S_2$ $[M]^+$ 1288.5, found 1288.9.

YC-VIII-12

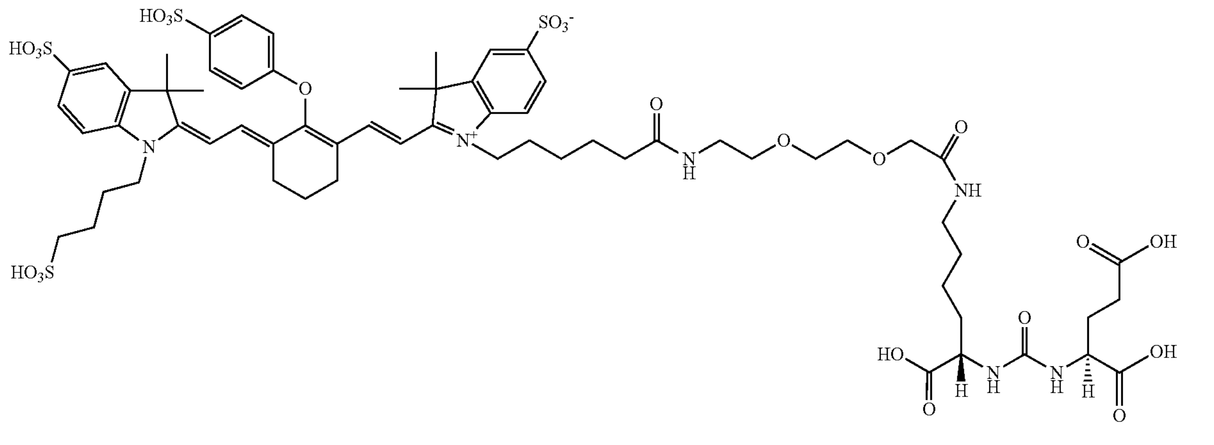

To a solution of compound YC-VI-54 (0.3 mg, 53 μmol) in DMSO (0.05 mL) was added N,N-diisopropylethylamine (0.002 mL, 11.4 μmol), followed by NHS ester of IRDye800CW (0.2 mg, 0.17 μmol). After 2 hour at room temperature, the reaction mixture was purified by HPLC (column, Econosphere C18 5μ, 150×4.6 mm; retention time, 22 min; mobile phase, A=0.1% TFA in $H_2O$, B=0.1% TFA in $CH_3CN$; gradient, 0 mins=0% B, 5 mins=0% B, 45 mins=100% B; flow rate, 1 mL/min) to afford 0.2 mg (80%) of compound YC-VIII-12. ESI-Mass calcd for $C_{64}H_{84}N_6O_{24}S_4$ $[M]^+$ 1448.4, found 1448.7.

YC-VIII-28

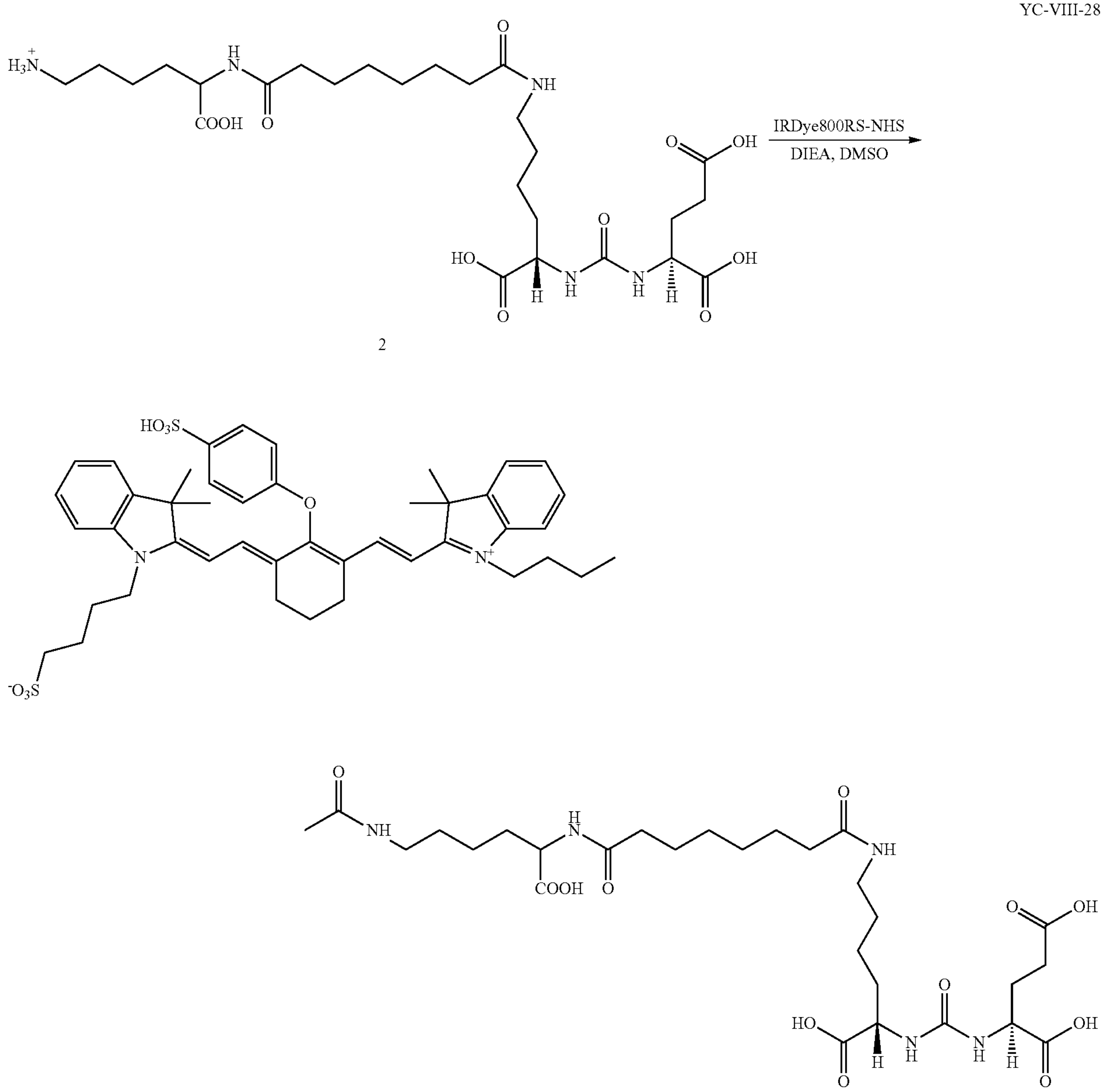

2

To a solution of YC-VIII-24 (prepared as described previously for YC-27) (0.3 mg, 0.42 μmol) in DMSO (0.1 mL) was added N,N-diisopropylethylamine (0.002 mL, 11.5 μmol), followed by NHS ester of IRDye 800RS (0.3 mg, 0.31 μmol). After 2 hour at room temperature, the reaction mixture was purified by HPLC (column, Econosphere C18 5μ, 150×4.6 mm; retention time, 27 min; mobile phase, A=0.1% TFA in $H_2O$, B=0.1% TFA in $CH_3CN$; gradient, 0 mins=0% B, 5 mins=0% B, 45 mins=100% B; flow rate, 1 mL/min) to afford 0.3 mg (67%) of compound YC-VIII-28. ESI-Mass calcd for $C_{72}H_{97}N_7O_{19}S_2$ $[M]^+$1427.6, found 714.4 $[M+H]^{2+}$, 1427.8 $[M]^+$.

YC-VIII-30

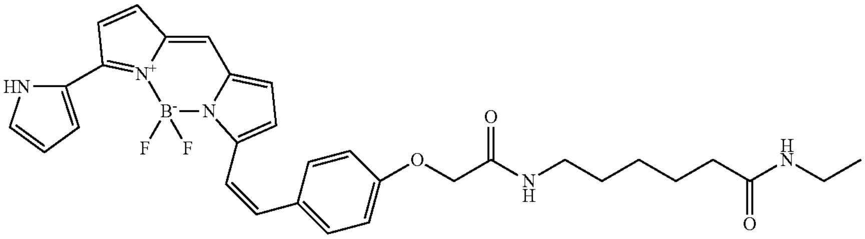

-continued

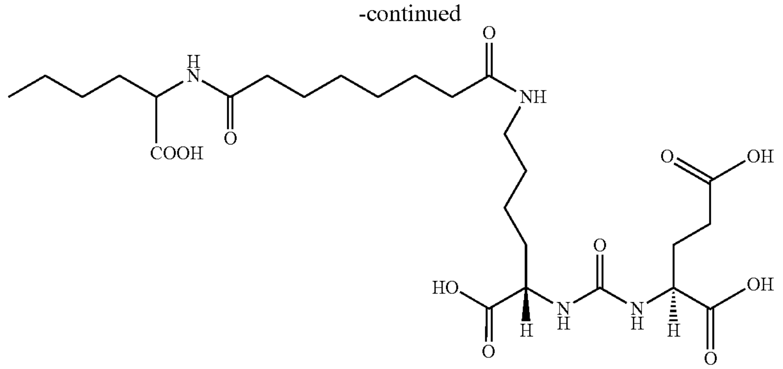

To a solution of YC-VIII-24 (0.5 mg, 0.70 μmol) in DMSO (0.1 mL) was added N,N-diisopropylethylamine (0.005 mL, 28.7 μmol), followed by NHS ester of BODIPY 650/665-X (0.3 mg, 0.47 μmol). After 2 hour at room temperature, the reaction mixture was purified by HPLC (column, Econosphere C18 5μ, 150×4.6 mm; retention time, 28 min; mobile phase, A=0.1% TFA in $H_2O$, B=0.1% TFA in $CH_3CN$; gradient, 0 mins=0% B, 5 mins=0% B, 45 mins=100% B; flow rate, 1 mL/min) to afford 0.4 mg (75%) of compound YC-VIII-30. ESI-Mass calcd for $C_{55}H_{73}BF_2N_9O_{14}$ $[M+H]^+$ 1132.5, found 1132.0.

YC-VIII-31

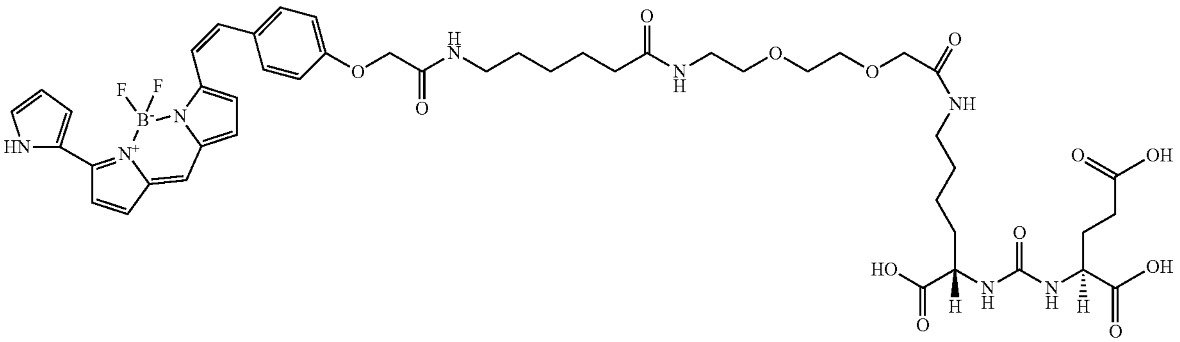

To a solution of YC-VI-54 (0.5 mg, 0.70 μmol) in DMSO (0.1 mL) was added N,N-diisopropylethylamine (0.005 mL, 28.7 μmol), followed by NHS ester of BODIPY 650/665-X (0.3 mg, 0.47 μmol). After 2 hour at room temperature, the reaction mixture was purified by HPLC (column, Econosphere C18 5μ, 150×4.6 mm; retention time, 29 min; mobile phase, A=0.1% TFA in $H_2O$, B=0.1% TFA in $CH_3CN$; gradient, 0 mins=0% B, 5 mins=0% B, 45 mins=100% B; flow rate, 1 mL/min) to afford 0.4 mg (86%) of compound YC-VIII-31. ESI-Mass calcd for $C_{47}H_{59}BF_2N_8O_{13}$ $[M]^+$992.4, found 992.9.

YC-VIII-41

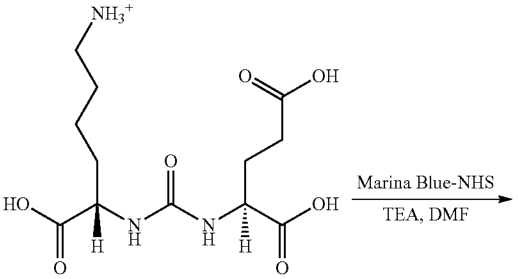

Lys-Urea-Glu

-continued

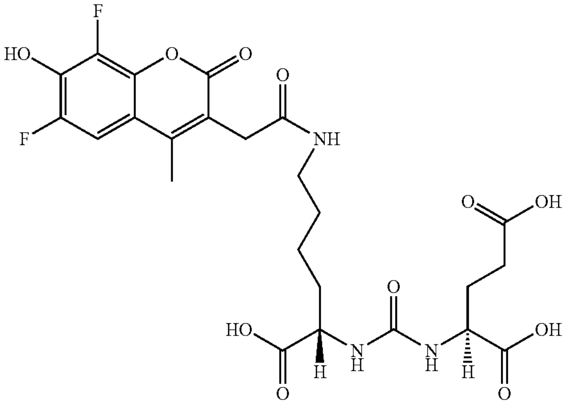

To a solution of Lys-Urea-Glu (4.0 mg, 9.6 μmol) in DMF (0.5 mL) was added triethylamine (0.01 mL, 71.7 μmmol), followed by Marina Blue-NHS ester (1.8 mg, 4.9 μmmol). After 2 hour at room temperature, the reaction mixture was purified by HPLC (column, Econosphere C18 10μ, 250×10 mm; retention time, 14 min; mobile phase, $H_2O/CH_3CN/TFA$=85/15/0.1; flow rate, 4 mL/min) to afford 2.5 mg (89%) of compound YC-VIII-41. $^1H$ NMR (400 MHz, $D_2O$) δ 7.40 (d, J=11.6 Hz, 1H), 4.23-4.31 (m, 1H), 4.15-4.19 (m, 1H), 3.64 (s, 2H), 3.19-3.23 (m, 2H), 2.49-2.53 (m, 2H), 2.39 (s, 3H), 2.06-2.17 (m, 1H), 1.95-1.99 (m, 1H), 1.83-1.90 (m, 1H), 1.72-1.80 (m, 1H), 1.52-1.55 (m, 2H), 1.40-1.45 (m, 2H). ESI-Mass calcd for $C_{24}H_{28}F_2N_3O_{11}$ $[M+H]^+$572.2, found 571.8.

YC-VIII-52

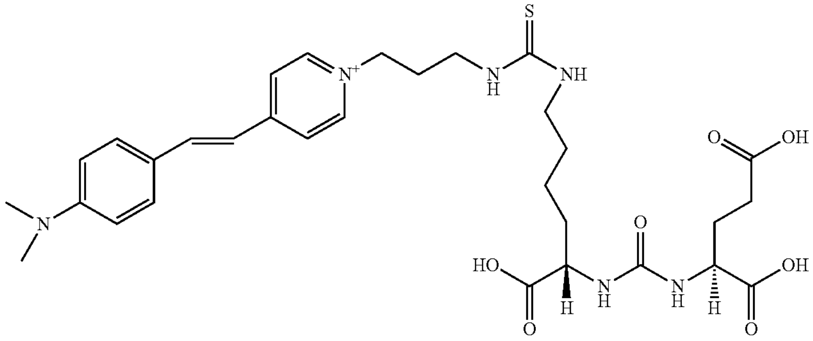

To a solution of Lys-Urea-Glu (4.0 mg, 9.6 μmol) in DMSO (0.5 mL) was added N,N-diisopropylethylamine (0.020 mL, 114.8 μmol), followed by 4-[2-(4-dimethylamino-phenyl)-vinyl]-1-(3-isothiocyanato-propyl)-pyridium (3 mg, 7.4 μmol). After 2 hour at room temperature, the reaction mixture was purified by HPLC (column, Econosphere C18 10μ, 250×10 mm; retention time, 13 min; mobile phase, A=0.1% TFA in $H_2O$, B=0.1% TFA in $CH_3CN$; gradient, 0 mins=10% B, 20 mins=60% B; flow rate, 4 mL/min) to afford 1.3 mg (24%) of compound YC-VIII-52. ESI-Mass calcd for $C_{31}H_{43}N_6O_7S$ $[M]^+$ 643.3, found 642.9.

YC-VIII-74

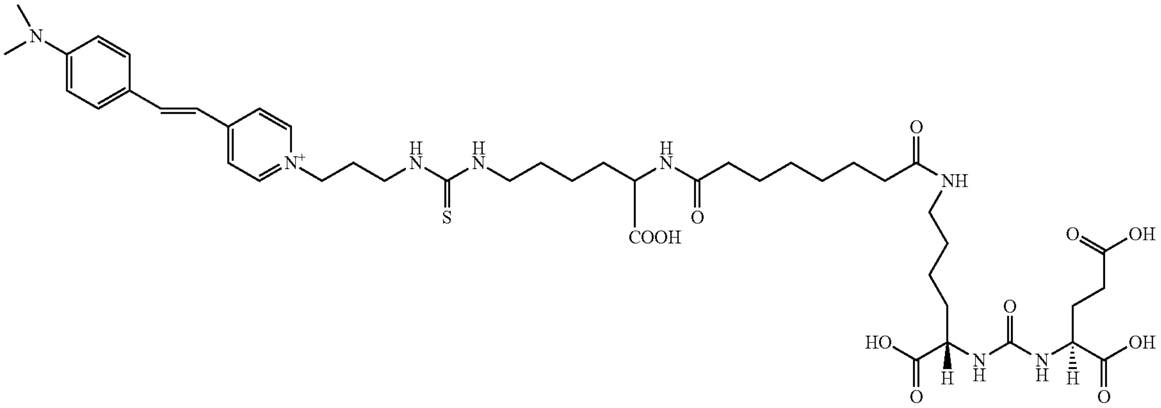

To a solution of YC-VIII-24 (3.0 mg, 4.2 μmol) in DMSO (0.5 mL) was added N,N-diisopropylethylamine (0.020 mL, 114.8 μmol), followed by 4-[2-(4-dimethylamino-phenyl)-vinyl]-1-(3-isothiocyanato-propyl)-pyridium (2 mg, 4.9 μmol). After 2 hour at room temperature, the reaction mixture was purified by HPLC (column, Econosphere C18 5μ, 150×4.6 mm; retention time, 15 min; mobile phase, A=0.1% TFA in $H_2O$, B=0.1% TFA in $CH_3CN$; gradient, 0 mins=0% B, 5 mins=0% B, 45 mins=100% B; flow rate, 1 mL/min) to afford 2 mg (47%) of compound YC-VIII-74. ESI-Mass calcd for $C_{45}H_{67}N_8O_{11}S$ $[M]^+$ 927.5, found 927.0.

To a solution of Lys-Urea-Glu (0.2 mg, 0.48 μmol) in DMSO (0.05 mL) was added N,N-diisopropylethylamine (0.002 mL, 11.5 μmol), followed by NHS ester of IRDye 800RS (0.2 mg, 0.21 μmol). After 2 hour at room temperature, the reaction mixture was purified by HPLC (column, Econosphere C18 5μ, 150×4.6 mm; retention time, 23 min; mobile phase, A=0.1% TFA in $H_2O$, B=0.1% TFA in $CH_3CN$; gradient, 0 mins=0% B, 5 mins=0% B, 45 mins=100% B; flow rate, 1 mL/min) to afford 0.2 mg (84%) of compound YC-IX-92. ESI-Mass calcd for $C_{58}H_{73}N_5O_{15}S_2$ $[M]^+$ 1143.5, found 572.5 $[M+H]^{2+}$, 1144.0 $[M]^+$.

YC-VIII-63

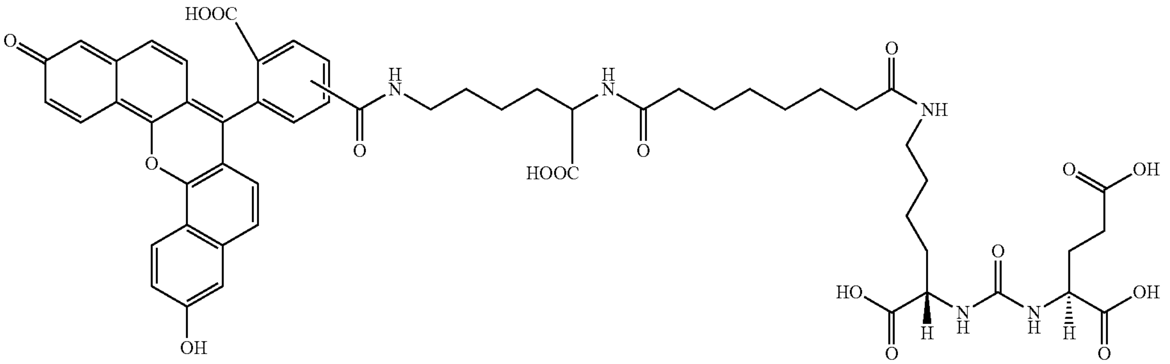

To a solution of YC-VIII-24 (5.0 mg, 7.0 μmol) in DMF (1 mL) was added triethylamine (0.020 mL, 143.5 μmol), followed by NHS ester of 5-(and -6)-carboxynaphthofluorescein (4.0 mg, 7.0 μmol). After 1 hour at room temperature, the reaction mixture was purified by HPLC (column, Econosphere C18 10μ, 250×10 mm; retention time, minor product at 17 min, major product at 20 min); mobile phase, $H_2O/CH_3CN/TFA$=70/30/0.1; flow rate, 4 mL/min) to afford 0.3 mg of minor and 2.2 mg of major product (two isomers of YC-VIII-63). ESI-Mass calcd for $C_{55}H_{59}N_5O_{17}$ $[M]^+$1061.4, found 1061.6 (for both minor and major product).

Characterization—Fluorescence

Figure 8:
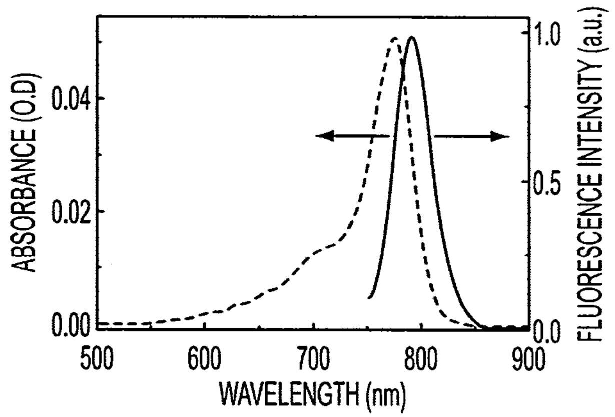
FIG. 8 shows the absorbance and emission spectra, and quantum yield of exemplary compound YC-27.

Fluorescence spectra were recorded using a Varian Cary Eclipse fluorescence spectrophotometer (Varian Medical Systems) with excitation from a Xenon arc lamp. YC-27 was dissolved in water. All of the fluorescence measurements were performed in aqueous solution under ambient conditions. The fluorescence quantum yield of YC-27 was measured using an aqueous solution of ICG (Φ=0.016 (Sevick-Muraca et al., Photochem. Photobiol., vol. 66, pp. 55-64, 1997), excitation wavelength at 775 nm) as the standard (FIG. 8). The fluorescence intensity data were collected in the spectral region 780-900 nm over which quantum yield was inte-

YC-IX-92

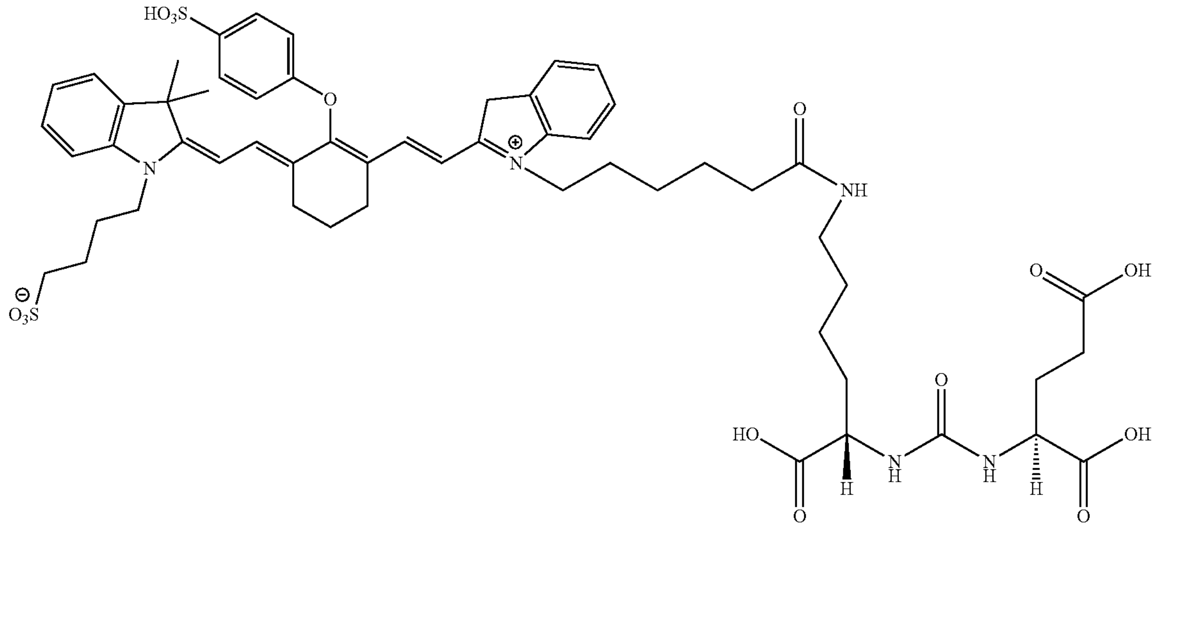

grated. Time-resolved intensity decays were recorded using a PicoQuant Fluotime 100 time-correlated single-photon counting (TCSPC) fluorescence lifetime spectrometer (PicoQuant, Berlin, Del.). The excitation was obtained using a pulsed laser diode (PicoQuant PDL800-B) with a 20 MHz repetition rate. The fluorescence intensity decay of YC-27 was analyzed in terms of the single-exponential decay using the PicoQuant Fluofit 4.1 software with deconvolution of the instrument response function and nonlinear least squares fitting. The goodness-of-fit was determined by the $X^2$ value.

Figure 9:
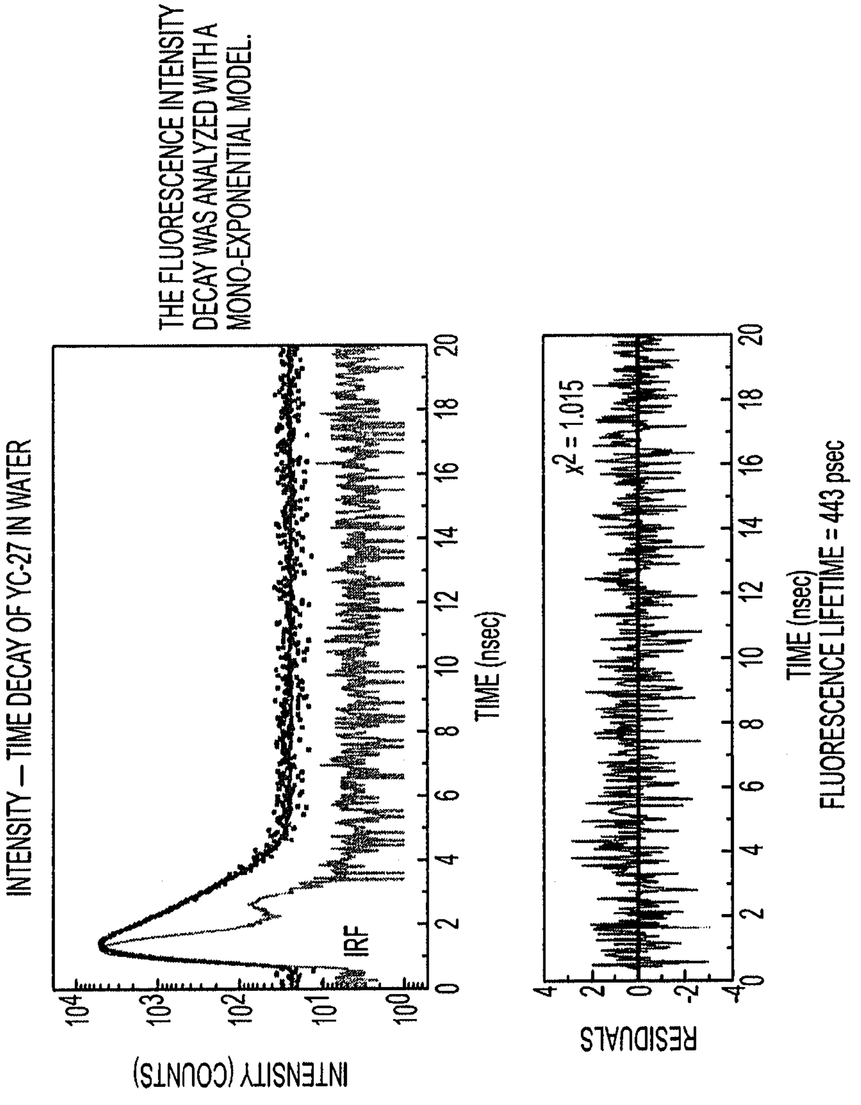
FIG. 9 shows the fluorescence decay of exemplary compound YC-27.

The electronic spectrum of YC-27 exhibited an absorbance maximum at 774 nm with an extinction coefficient of 158,900 $M^{-1}$. Upon excitation, YC-27 provided intense fluorescence with an emission maximum at 792 nm and a fluorescence lifetime of 443 psec in aqueous solution (FIG. 9). Using an excitation wavelength of 775 nm, YC-27 demonstrated a fluorescence quantum yield of 0.053 in aqueous solution relative to ICG, which demonstrated a quantum yield of 0.016 (FIG. 8) (Sevick-Muraca et al., Photochem. Photobiol., vol. 66, pp. 55-64, 1997), attesting to the efficiency of this IRDye 800CW-based compound. That is significant because ICG has been used previously for intraoperative tumor mapping (K. Gotoh, T. Yamada, O. Ishikawa, H. Takahashi, H. Eguchi, M. Yano, H. Ohigashi, Y. Tomita, Y. Miyamoto, and S. Imaoka, A novel image-guided surgery of hepatocellular carcinoma by indocyanine green fluorescence imaging navigation. J. Surg. Oncol., 2009).

In vitro NAALADase Activity

PSMA inhibitory activity of YC-27 was determined using a fluorescence-based assay according to a previously reported procedure (Chen et al., J. Med. Chem., vol. 51, pp. 7933-7943, 2008). Briefly, lysates of LNCaP cell extracts (25 μl) were incubated with the inhibitor (12.5 μl) in the presence of 4 μM N-acetylaspartylglutamate (NAAG) (12.5 μL) for 120 min. The amount of glutamate released by NAAG hydrolysis was measured by incubation with a working solution (50 μL) of the Amplex Red Glutamic Acid Kit (Molecular Probes Inc., Eugene, Oreg.) for 60 min. Fluorescence was measured with a VICTOR$^3$V multilabel plate reader (Perkin Elmer Inc., Waltham, Mass.) with excitation at 530 nm and emission at 560 nm. Inhibition curves were determined using semi-log plots, and $IC_{50}$ values were determined at the concentration at which enzyme activity was inhibited by 50%. Assays were performed in triplicate. Enzyme inhibitory constants (K, values) were generated using the Cheng-Prusoff conversion [19]. Data analysis was performed using GraphPad Prism version 4.00 for Windows (GraphPad Software, San Diego, Calif.).

Figure 10:
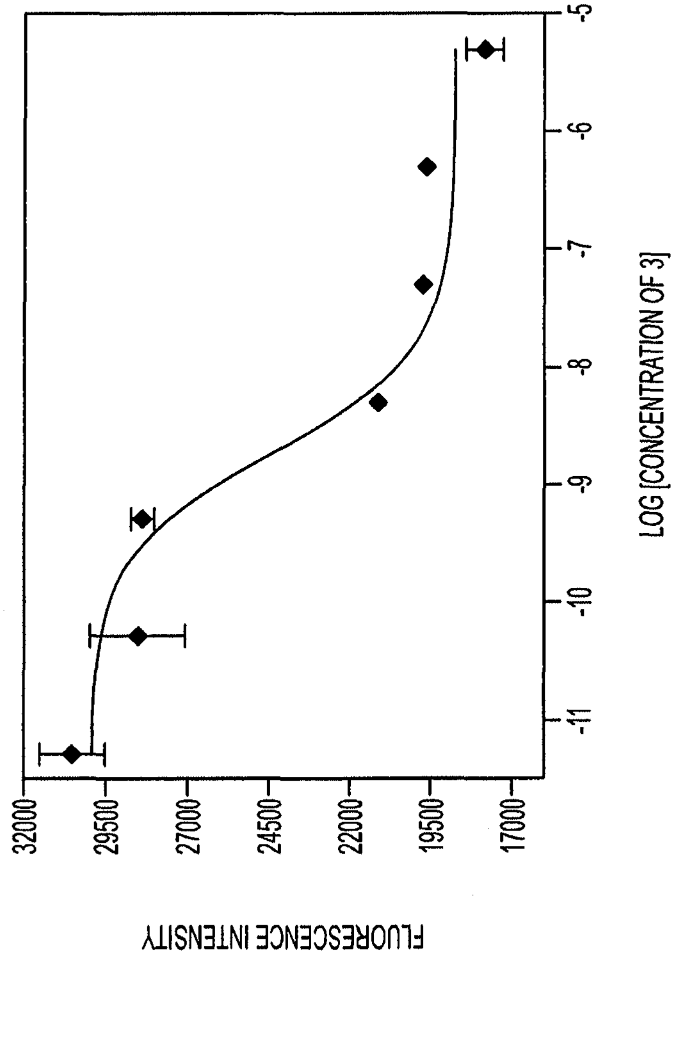
FIG. 10 shows an $IC_{50}$ curve of compound YC-27 using a fluorescence-based NAALADase assay
Figure 11A:
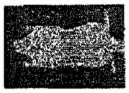
FIG. 11 shows in vivo imaging of a NOD/SCID mouse (mouse #1), bearing PC3-PIP (forward left flank) and PC3-flu (forward right flank) tumors. Mouse #1 received 10 nmol of YC-27 and dorsal (animal prone) and ventral (animal supine) views were obtained. Dorsal and ventral views at 40 min p.i. (A, B, respectively); 18.5 h (C, D); 23 h (E, F); 42.5 h (G, H); 68 h (I, J). Dorsal view of pre-injection image (K). Dorsal and ventral views 70.5 h p.i. (L, M). Images after midline laparotomy (N) and individually harvested organs (O) on a Petri dish at 70.5 h p.i. Images were scaled to the same maximum (arbitrary units).
Figure 11B:
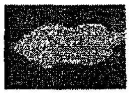
Figure 11C:
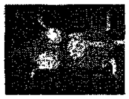
Figure 11D:
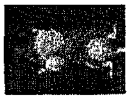
Figure 11E:
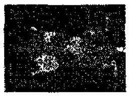
Figure 11F:
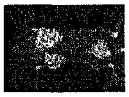
Figure 11G:
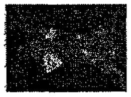
Figure 11H:
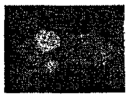
Figure 11I:
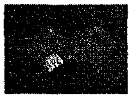
Figure 11J:
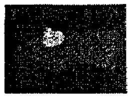
Figure 11K:
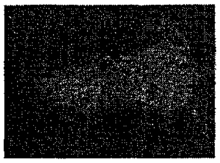
Figure 11L:
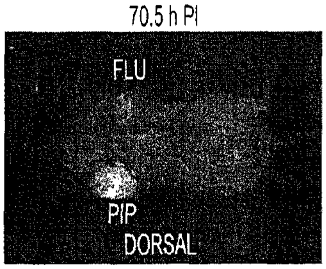
Figure 11M:
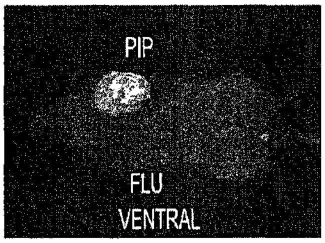
Figure 11N:
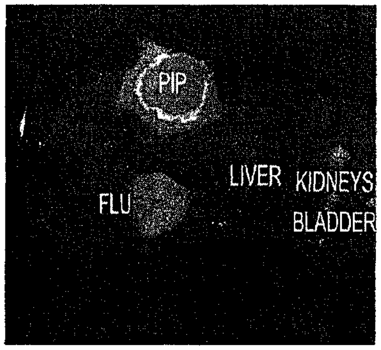
Figure 11O:
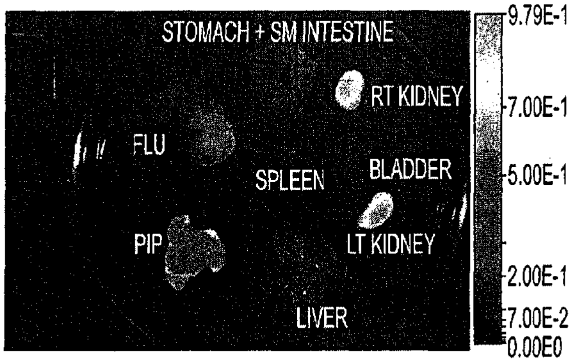

This assay is free from the interference of IRDye 800CW because the excitation/emission maxima of IRDye 800CW are remote from those of resorufin ($\lambda_{ex}$=563 nm, $\lambda_{em}$=587 nm), which provides the fluorescent readout in the assay. The K, value of YC-27 was 0.37 nM with 95% confidence intervals from 0.18 nM to 0.79 nM. Under the same experimental conditions, the K, value of the known PSMA inhibitor ZJ-43 (Zhou et al., Nat. Rev. Drug Discov., vol. 4, pp. 1015-1026, 2005) was 2.1 nM, indicating the high inhibitory capacity of YC-27. The inhibition curve of YC-27, which is expressed with respect to the amount of glutamate released from hydrolysis of NAAG, is shown in FIG. 10.

Biodistribution and Imaging

Cell Culture and Animal Models.

Both PSMA-expressing (PSMA+ PC3-PIP) and non-expressing (PSMA− PC3-flu) prostate cancer cell lines (Chang et al, Cancer Res., vol. 59, pp. 3192-3198, 1999) were grown in RPMI 1640 medium (Invitrogen, Carlsbad, Calif.) containing 10% fetal bovine serum (FBS) (Invitrogen) and 1% Pen-Strep (Biofluids, Camarillo, Calif.). All cell cultures were maintained in 5% carbon dioxide ($CO_2$), at 37.0° C. in a humidified incubator Animal studies were undertaken in compliance with the regulations of the Johns Hopkins Animal Care and Use Committee. Six- to eight-week-old male, non-obese diabetic (NOD)/severe-combined immunodeficient (SCID) mice (Charles River Laboratories, Wilmington, Mass.) were implanted subcutaneously (s.c.) with PC3-PIP and PC3-flu cells ($2\times10^6$ in 100 μL of Matrigel) at the forward left and right flanks, respectively. Mice were imaged or used in ex vivo biodistribution assays when the xenografts reached 5 to 7 mm in diameter.

In Vivo Imaging and Ex Vivo Biodistribution.

Mouse #1 was injected with 10 nmol and mouse #2 with 1 nmol of YC-27 in 200 μl of PBS intravenously (i.v.) via the lateral tail vein. Mouse #3 was injected with 1 nmol of YC-27 and also co-injected with 1 μmol of the known PSMA inhibitor 2-{3-[1-carboxy-5-(4-iodo-benzoylamino)-pentyl]-ureido}-pentanedioic acid (DCIBzL) (Chen et al., J. Med. Chem., vol. 51, pp. 7933-7943, 2008; Barinka et al., J. Med. Chem. vol. 51, pp. 7737-7743, 2008) in 200 μL of PBS i.v. to assess for PSMA binding specificity. Images were acquired at an array of post-injection (p.i.) time points starting at 10 min p.i. using a dedicated small animal optical imaging instrument, the Pearl Imager (LI-COR Biosciences). The Pearl Imager uses diffusive lasers optimized for IRDye 800CW. The instrument employs a CCD camera with a field-of-view of 11.2 cm×8.4 cm at the surface of the imaging bed. The scan time was less than 30 sec to complete white light, 700 nm channel and 800 nm channel image acquisition. Images are displayed using a pseudocolor output with corresponding scale. All images were acquired at the same parameter settings and are scaled to the same maximum values. Imaging bed temperature was adjusted to 37° C. Animals received inhalational anesthesia (isoflurane) through a nose cone attached to the imaging bed Animals were sacrificed by cervical dislocation for ex vivo imaging studies at the end of acquisition of the in vivo images. Ex vivo images were acquired first by midline surgical laparotomy and then again by harvesting liver, spleen, stomach, small intestine, kidneys, urinary bladder, PC3-PIP and PC3-flu tumors and displaying them individually on plastic Petri dishes. Estimates of signal output were provided by drawing three circular regions of interest within each tumor and determining the average signal (arbitrary units)/area using the manufacturer's software.

FIG. 11 (mouse #1) depicts the pharmacokinetic behavior of YC-27 in vivo. In this experiment 10 nmol of YC-27 was administered intravenously and the animal was imaged repeatedly over a three day period. Although difficult to quantify as these are planar images, one can see clearly increased uptake in the PSMA+ PC3-PIP tumor relative to the control (PSMA-negative) PC3-flu tumor at 18.5 h p.i. through 70.5 h p.i. (FIG. 11C through 11M). Using quantitative real time polymerase chain reaction (qRT-PCR) we measured the relative amounts of PSMA mRNA expression in extracts of the tumors in mice #1-3, and confirmed that PC3-PIP tumors (left flank) expressed PSMA mRNA at levels several million times higher than PC3-flu tumors (right flank) (data not shown). Panels 11L and 11M show emission from the intact, living, unshaven animal, while panels 11N and 110 are postmortem studies with organs exposed. Note that in 11L one can barely discern the kidneys, a known target site for PSMA (Tasch et al., Crit. Rev. Immunol., vol. 21, pp. 249-261, 2001; Pomper et al., Mol. Imaging, vol. 1, pp. 96-101, 2002; Kinoshita et al., World J. Surg., vol. 30, pp. 628-636, 2006), while the kidneys are clearly visible in 110 when exposed. A portion of that renal light emission may be due to clearance of this relatively hydrophilic compound. The estimated target-to-nontarget ratio (PC-3 PIP vs. PC-3 flu light output) was 10 when comparing the tumors from panel M (70.5 h p.i.).

Figures 12A, 12B, 12C, 12D, 12E, 12F, 12G, 12H, 12I, 12J:
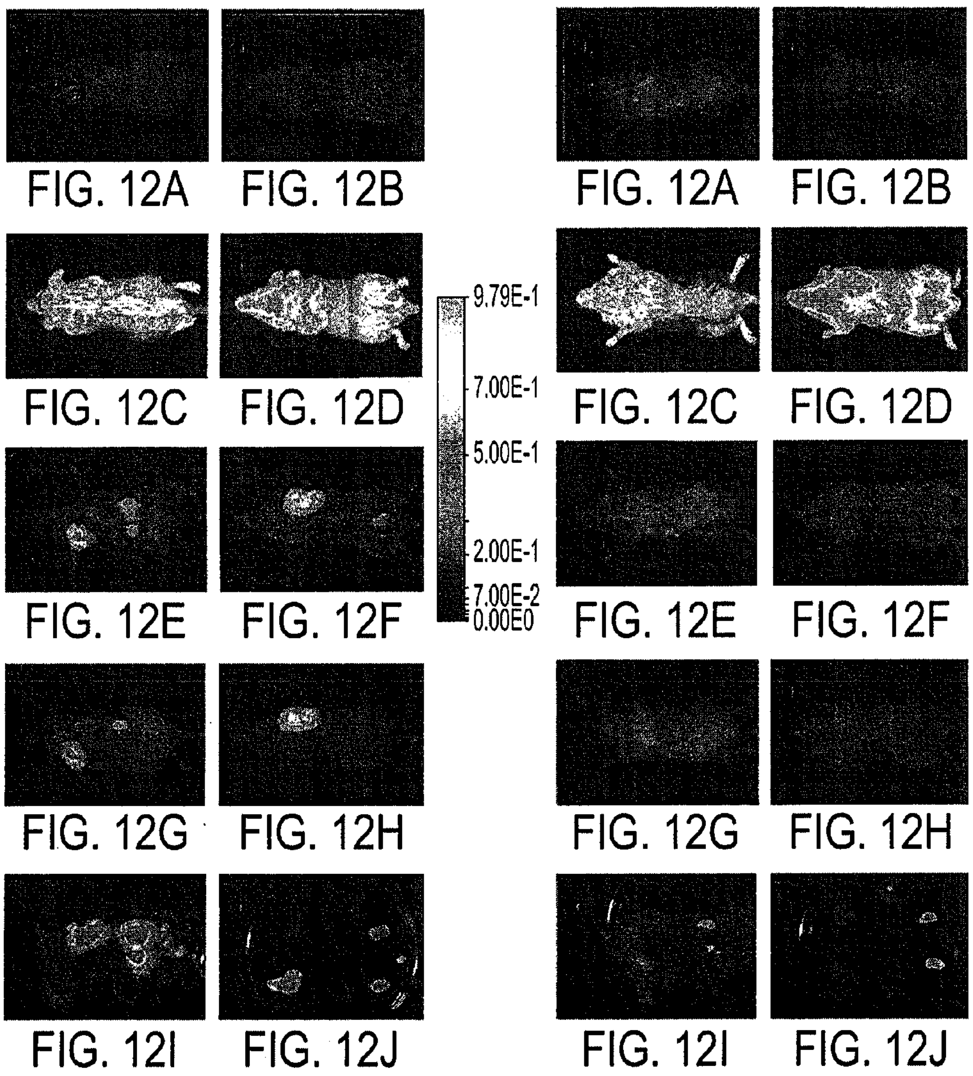
FIG. 12 shows in vivo imaging of a NOD/SCID mouse (mouse #2) (left panel), bearing PC3-PIP (forward left flank) and PC3-flu (forward right flank) tumors. Mouse #2 received 1 nmol of YC-27 and dorsal (animal prone) and ventral (animal supine) views were obtained. Dorsal and ventral views of the pre-injection image (A, B, respectively); 10 min p.i. (C, D); 20.5 h (E, F); 24 h (G, H). Images after midline laparotomy (I) and individually harvested organs (J) on a Petri dish at 24 h p.i. Right Panels: Mouse #3 in same orientation as mouse #2. Mouse #3 received 1 nmol of YC-27 co-injected with 1 μmol of DCIBzL, which served as a blocking agent to test binding specificity. Images were scaled to the same maximum (arbitrary units).
Figure 13:
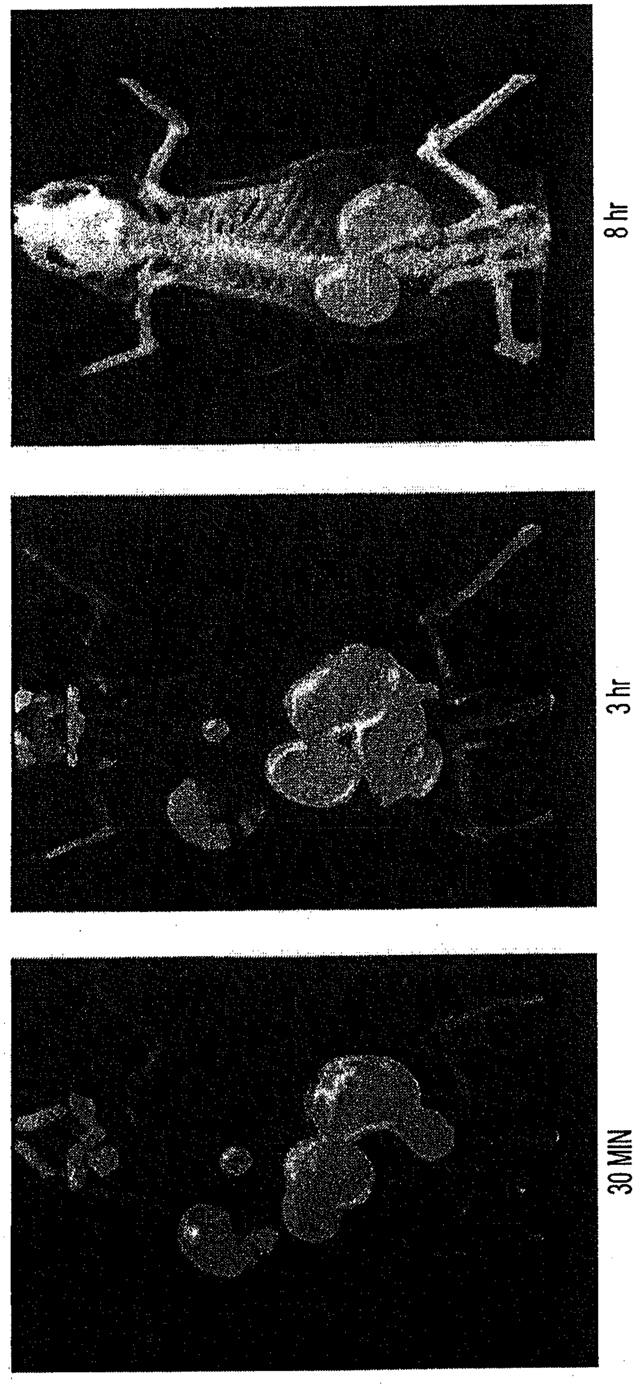
FIG. 13 shows SPECT-CT images of a PSMA+ LNCaP tumor-bearing mouse injected intravenously with exemplary compound [$^{99m}$Tc]SRVI34B.
Figure 14:
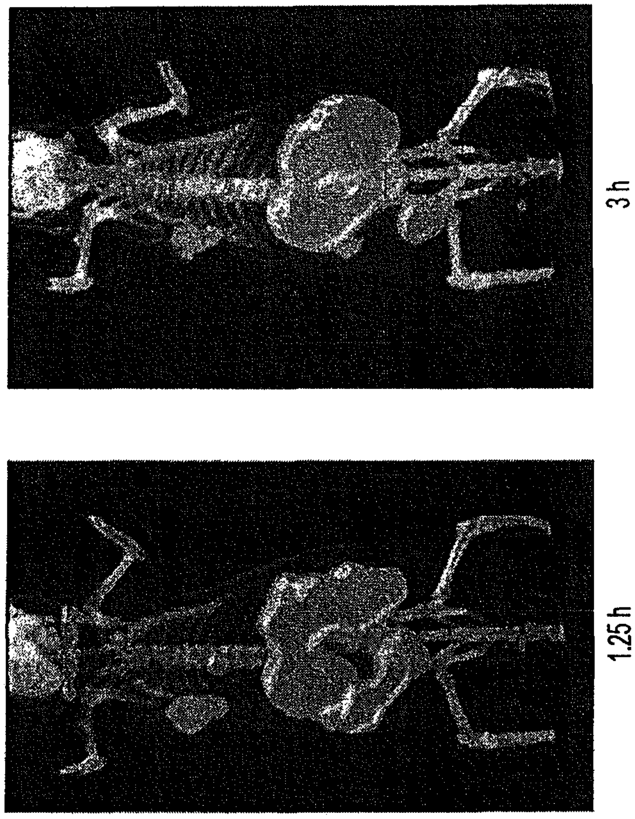
FIG. 14 shows SPECT-CT images of a PSMA+ PC3-PIP tumor-bearing mouse injected intravenously with exemplary compound [$^{99m}$Tc]SRVI34B.
Figure 15:
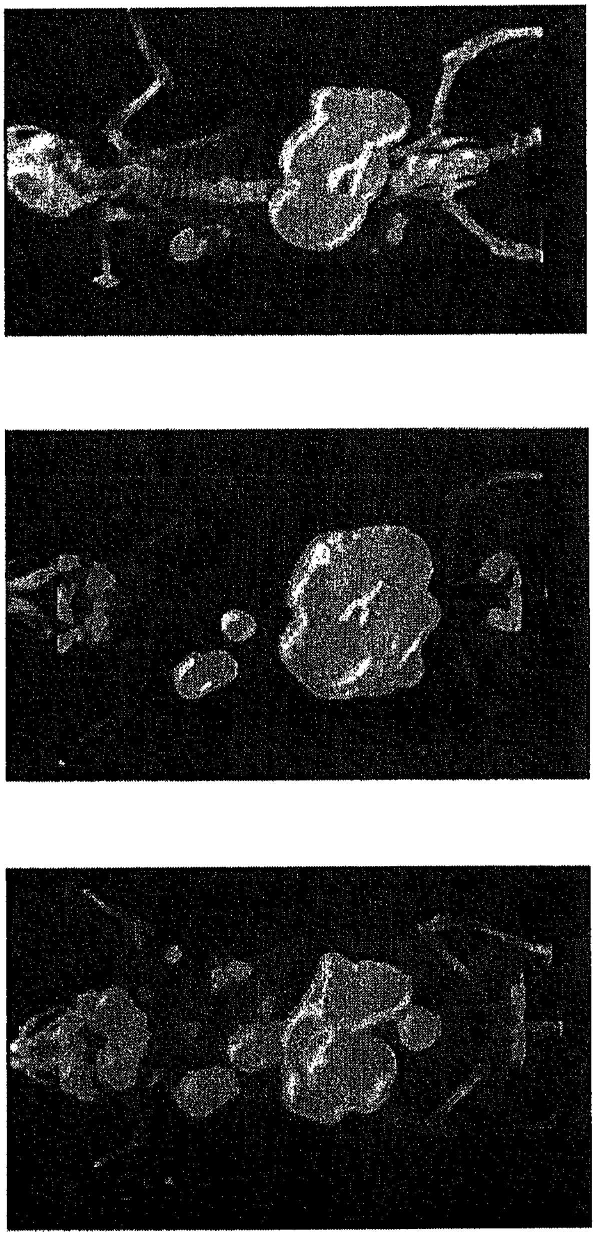
FIG. 15 shows SPECT-CT images of a PSMA+ PC3-PIP (forward left flank) and PSMA− PC3-flu (forward right flank) tumor-bearing mouse injected intravenously with exemplary compound [$^{99m}$Tc] SRVI34A.
Figure 16:
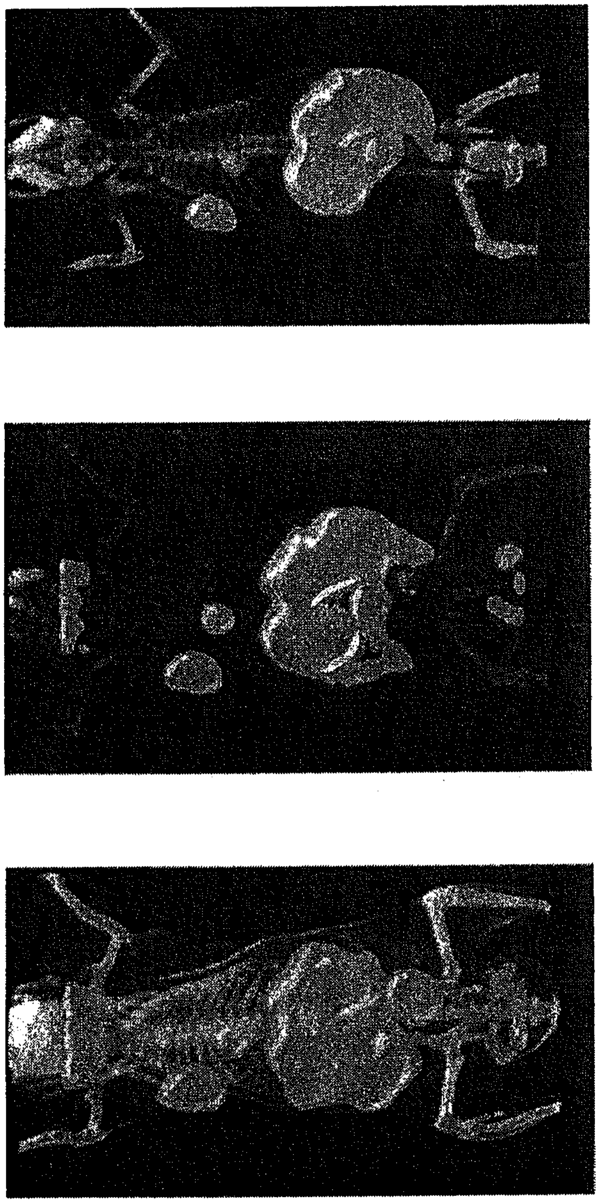
FIG. 16 shows SPECT-CT images of a PSMA+ PC3-PIP (forward left flank) and PSMA− PC3-flu (forward right flank) tumor-bearing mouse injected intravenously with exemplary compound [$^{99m}$Tc] SRVI34B.

The experiment in FIG. 12 was performed with 10-fold less YC-27 administered than in the previous experiment. Despite reducing the concentration of YC-27, PSMA+ PC3-PIP tumor could be seen clearly at one day p.i. (FIG. 12, mouse #2, Left Panels). DCIBzL, a known, high-affinity PSMA inhibitor, was co-administered with YC-27 as a test of binding specificity (FIG. 12, mouse #3, Right Panels). Nearly all of the light emission from target tumor, as well as kidneys, was blocked, demonstrating the specificity of this compound for PSMA in vivo. The estimated target-to-nontarget ratio (PC-3 PIP vs. PC-3 flu light output) was 26 when comparing the tumors from panel F (20.5 h p.i.). By administering 1 nmol to this ~25 g mouse, we have realized the high sensitivity of in vivo optical imaging, rivaling that of the radiopharmaceutical-based techniques. For example, 1 nmol converts to 1.6 μg injected. If we synthesized a similar compound labeled with $^{18}F$ or other radionuclide at 1,000 mCi/μmol (37 GBq/μmol), and administered a standard dose of 200 μCi (7.4 MBq) to a mouse, we would be injecting 0.3 μg.

Interestingly, in mouse #1, which received 10 nmol of YC-27, we observed a small degree of non-specific uptake at the 23 h time point, manifested as uptake within PSMA-negative PC3-flu tumors. That finding could be due to enhanced permeability and retention of YC-27. No non-specific uptake/retention was observed at a similar, 20.5 h, time point in mouse #2, which received a 10-fold lower dose. That finding suggests the need for further optimization of dose and timing for in vivo applications.

Discussion

A wide variety of low molecular weight PSMA-based imaging agents have been synthesized, including those using the urea scaffold (Banerjee et al., J. Med. Chem., vol. 51, pp. 4504-4517, 2008; Chen et al., J. Med. Chem., vol. 51, pp. 7933-7943, 2008; Zhou et al., Nat. Rev. Drug Discov., vol. 4, pp. 1015-1026, 2005; Pomper et al., Mol. Imaging, vol. 1, pp. 96-101, 2002; Foss et al., Clin. Cancer Res., vol. 11, pp. 4022-4028, 2005; Humblet et al., Mol. Imaging, vol. 4, 448-462, 2005; Misra et al., J. Nucl. Med., vol. 48, pp. 1379-1389, 2007; Mease et al., Clin. Cancer Res., vol. 14, pp. 3036-3043, 2008; Liu et al., Prostate, vol. 68, pp. 955-964, 2008; Humblet et al., J. Med. Chem., vol. 52, pp. 544-550, 2009; Kularatne et al., Mol. Pharm., vol. 6, pp. 790-800, 2009; Hillier et al., Cancer Res., vol. 69, pp. 6932-6940, 2009). Those compounds have primarily been radiopharmaceuticals, but optical agents exist. In two separate studies Humblet et al. reported the synthesis of mono- and polyvalent NIR fluorescent phosphonate derivatives for imaging PSMA, but little accumulation in PSMA-expressing tumors was evident in the former study (Humblet et al., Mol. Imaging, vol. 4, pp. 448-462, 2005) while no in vivo results were reported in the latter (Humblet et al., J. Med. Chem., vol. 52, pp. 544-550, 2009). Liu et al have also synthesized fluorescent phosphonate derivatives and have demonstrated their PSMA-binding specificity and intracellular localization in vitro (Liu et al., Prostate, vol. 68, pp. 955-964, 2008). Recently Kularatne et al. have synthesized fluorescent (fluorescein and rhodamine) urea derivatives that demonstrate PSMA migration to endosomes (Kularatne et al., Mol. Pharm., vol. 6, pp. 790-800, 2009). We arrived at YC-27 based on structure-activity relationships developed for PSMA-binding ureas, which were focused on improving pharmacokinetics for use in vivo by optimization of the linker-chelate complex (Banerjee et al., J. Med. Chem., vol. 51, pp. 4504-4517, 2008). Calculated hydrophobicity values (Ghose et al., J. Phys. Chem. A, vol. 102, pp. 3762-3772, 1998) suggest that YC-27 should be considerably more hydrophobic (ALogD=5.96) than radiopharmaceuticals such as [$^{125}$I]DCIBzL (ALogD=1.19), perhaps accounting for its long tumor retention, which is desirable for an optical imaging agent intended for intraoperative use. We confirmed greater hydrophobicity of YC-27 relative to DCIBzL through reverse-phase HPLC (data not shown)

Example 6

Synthesis of YC-VIII-36

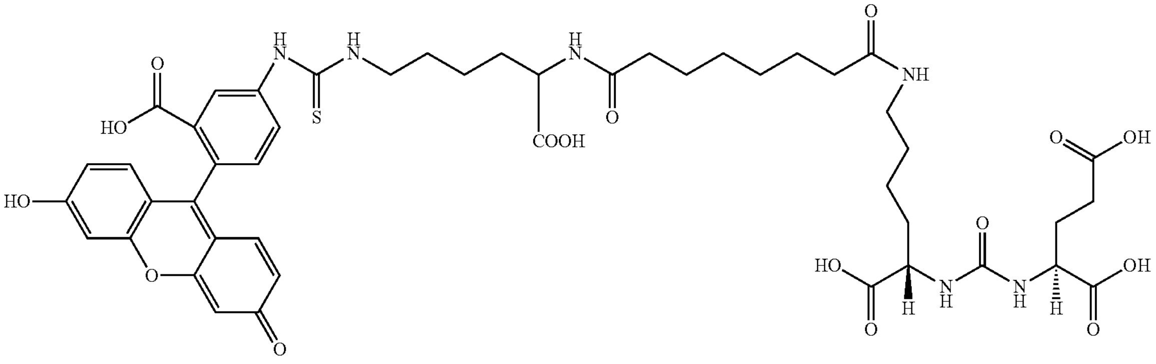 [SMILES: O=C(O)CC[C@H](NC(=O)N[C@@H](CCCCNC(=O)CCCCCCC(=O)NC(CCCCNC(=S)Nc1ccc(-c2c3ccc(=O)cc-3oc3cc(O)ccc23)c(C(=O)O)c1)C(=O)O)C(=O)O)C(=O)O]

To a solution of YC-VIII-24 (prepared as described in Example 5) (1.5 mg, 0.21 μmol) in DMF (1 mL) was added triethylamine (0.005 mL, 35.9 μmol), followed by fluorescein isothiocyanate isomer 1 (1 mg, 2.57 μmol). After 2 hours at room temperature, the reaction mixture was purified by HPLC (column, Econosphere C18 5μ, 150×4.6 mm; retention time, 15 min; mobile phase, $H_2O/CH_3CN/TFA$=75/25/0.1; flow rate, 1 mL/min) to afford 1.5 mg (72%) of compound YC-VIII-36. ESI-Mass calcd for $C_{47}H_{57}N_6O_{16}S$ $[M+H]^+$ 993.4, found 992.8.

Cell Labeling

Figure 17:
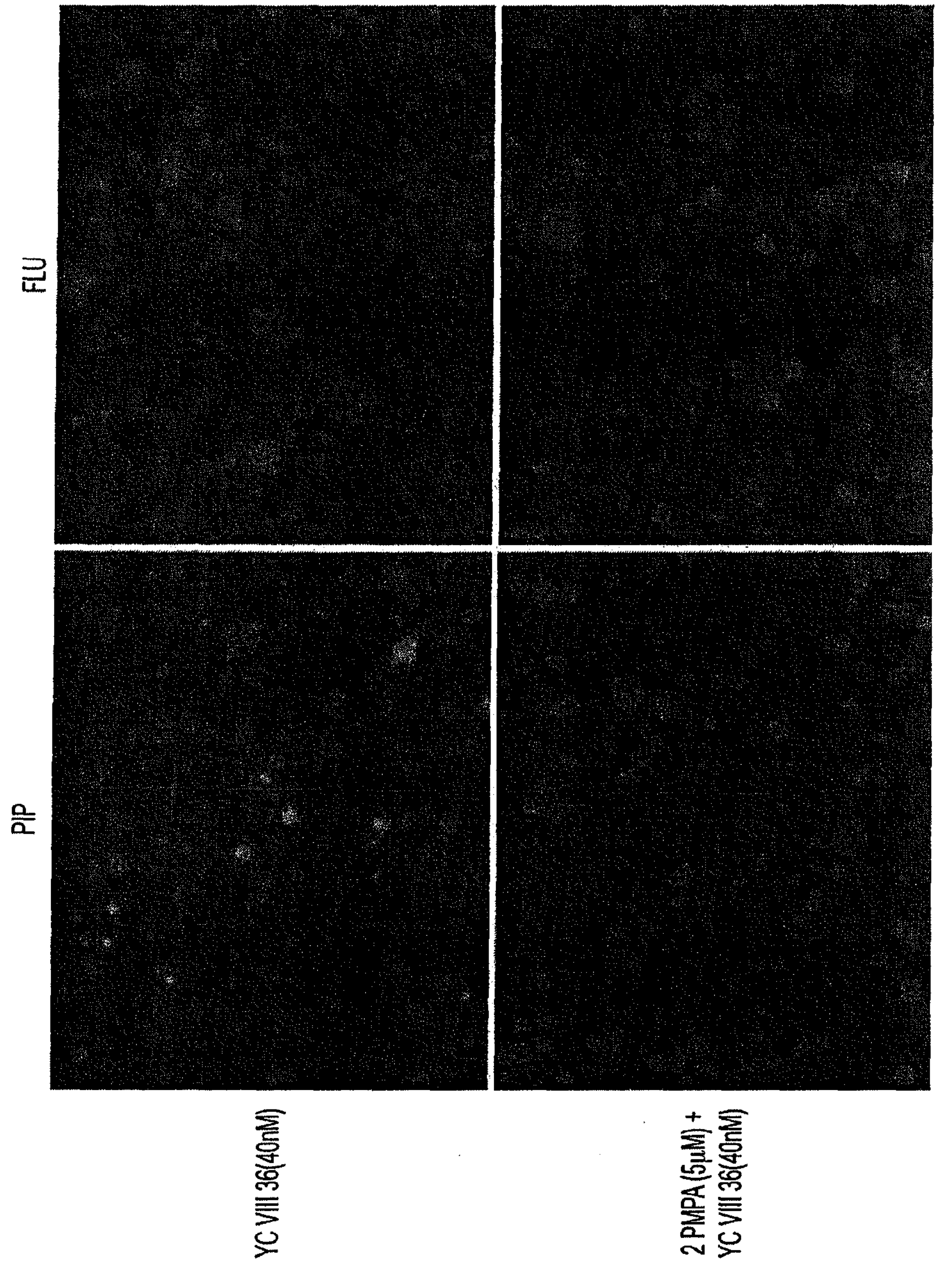
FIG. 17 shows PC3-PIP and PC3-flu cells treated with fluorescent compound YC-VIII-36 (green, top left) and DAPI (blue), and PC3-PIP and PC3-flu cells treated with both YC-VIII-36 and PSMA inhibitor, PMPA.

PSMA positive PIPcells, and PSMA negative FLU cells were treated with compound YC-VIII-36 (40 nM) and 4',6-diamidino-2-phenylindole (DAPI, blue). FIG. 17 shows fluorescence of cells expressing PSMA (green fluorescence, top left). PIP and FLU cells were treated with both YC-VIII-36 and PSMA inhibitor PMPA (5 μM), showing inhibition of cellular fluorescence by PMPA (FIG. 17, bottom).

Figure 18:
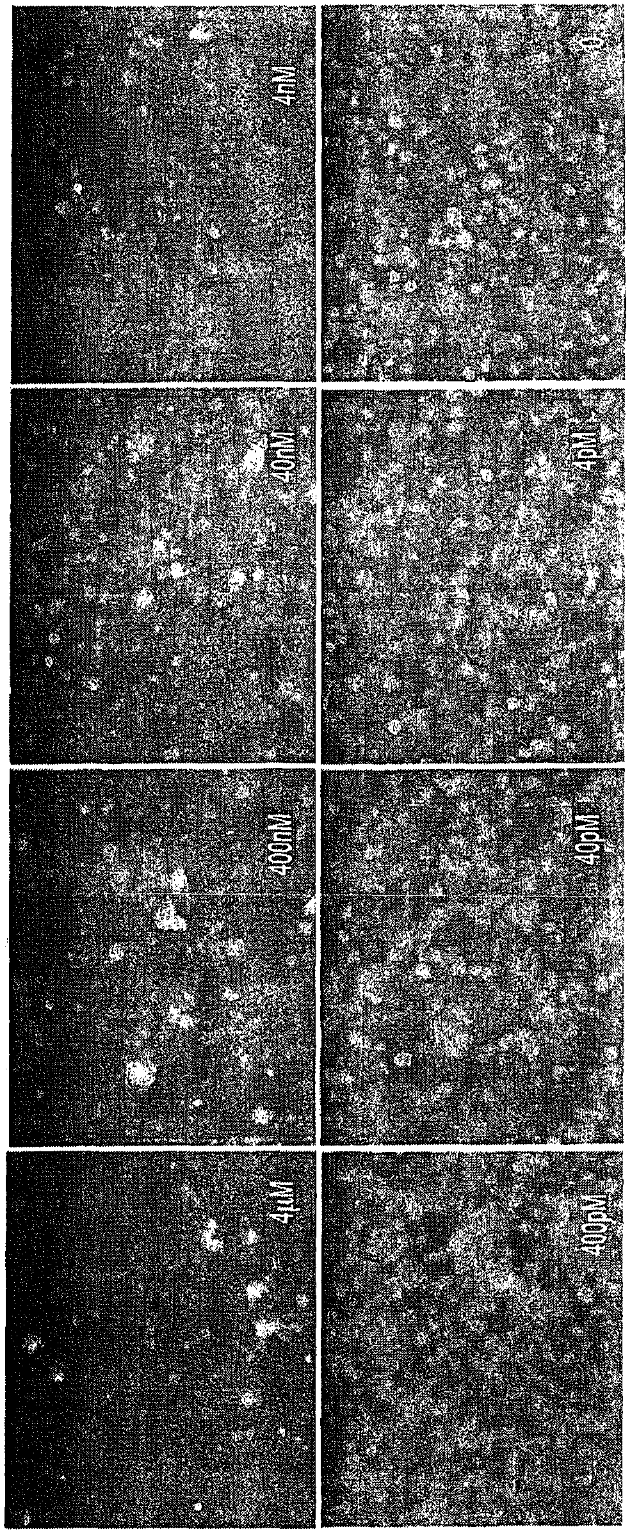
FIG. 18 shows PC3-PIP cells treated with DAPI (blue) and varying concentrations of YC-VIII-36 (green).

FIG. 18 shows PC3-PIP cells treated with DAPI (blue) and varying concentrations of YC-VIII-36 (green).

Figure 19:
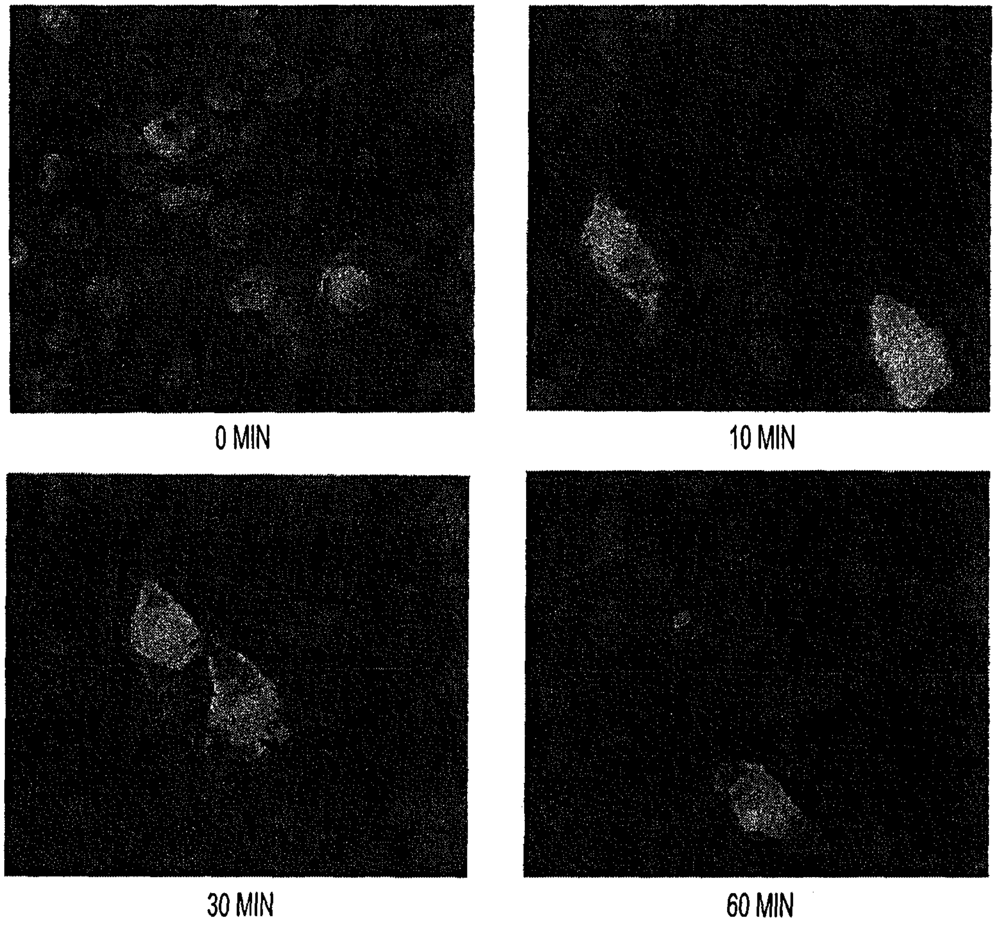
FIG. 19 shows time dependent internalization of YC-VIII-36 into PC3-PIP cells treated with YC-VIII-36 (green) and DAPI (blue).

FIG. 19 shows time dependent internalization of YC-VIII-36 into PC3-PIP cells treated with YC-VIII-36 (green) and DAPI (blue). The time dependent internalization study was done as described (Liu et al., Prostate vol. 68, pp. 955-964, 2008) with appropriate modifications. Briefly, PC3-PIP cells were seeded as above. The cells were first pre-chilled by incubating with ice cold complete growth media and then incubated with ice cold complete growth media containing 500 nM of compound YC-VIII-36 at 40 C for 1 hr. After 1 hr of incubation the excess compound was removed by washing the wells twice with ice-cold complete growth media and then the wells were replenished with pre-warmed complete growth media. The chamber slides containing cells were incubated for 10 min, 30 min, 60 min and 180 min at 37° C. in a humidified incubator.

In vivo Imaging

Figure 20:
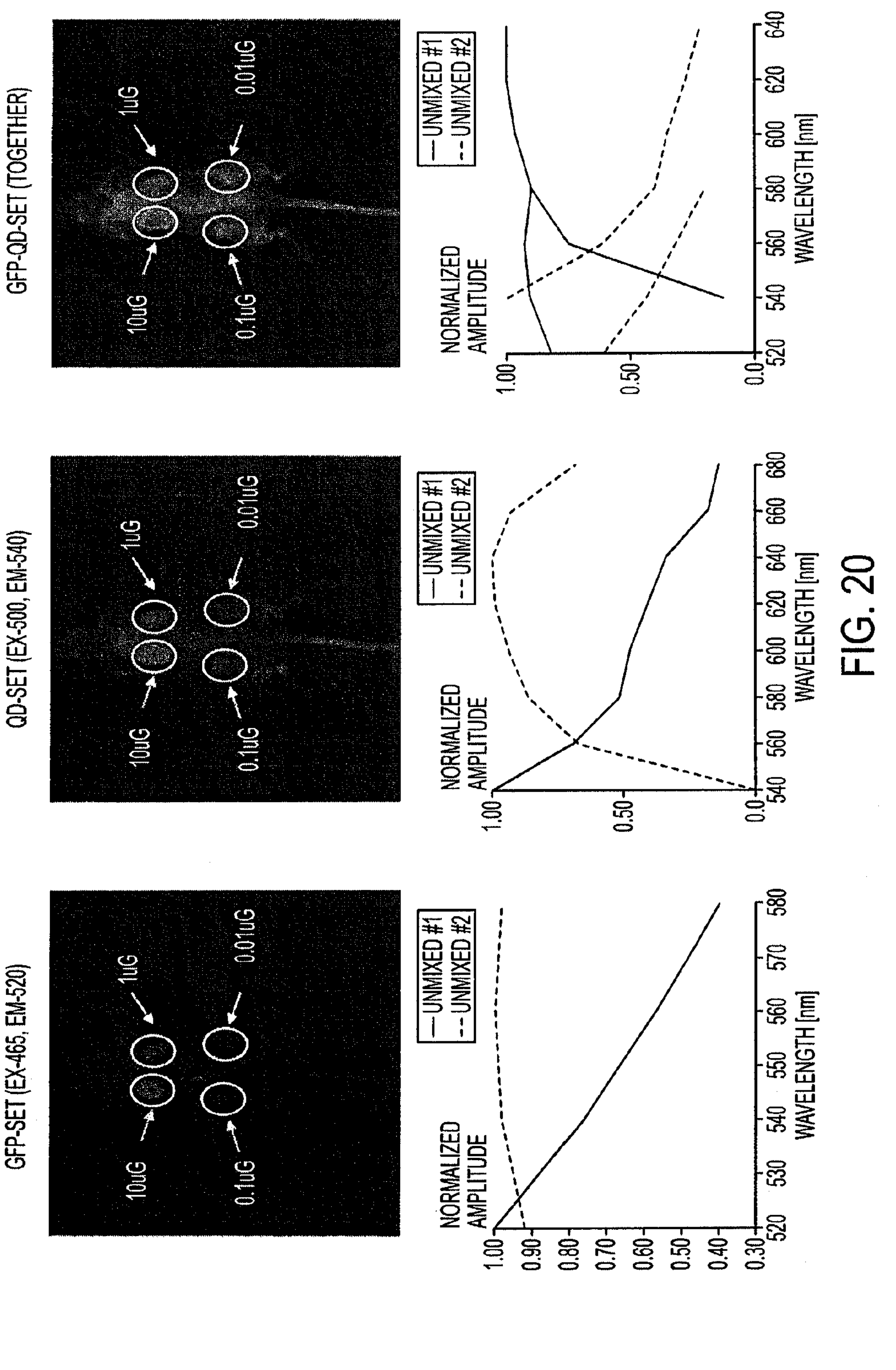
FIG. 20 shows titration and detection of varying amounts of YC-VIII-36 injected subcutaneously into a nude mouse. (IVIS spectrum with 10 second exposure followed by spectral unmixing)

FIG. 20 shows titration and detection of varying amounts of YC-VIII-36 injected subcutaneously into a nude mouse. (IVIS spectrum with 10 second exposure followed by spectral unmixing)

Figure 21:
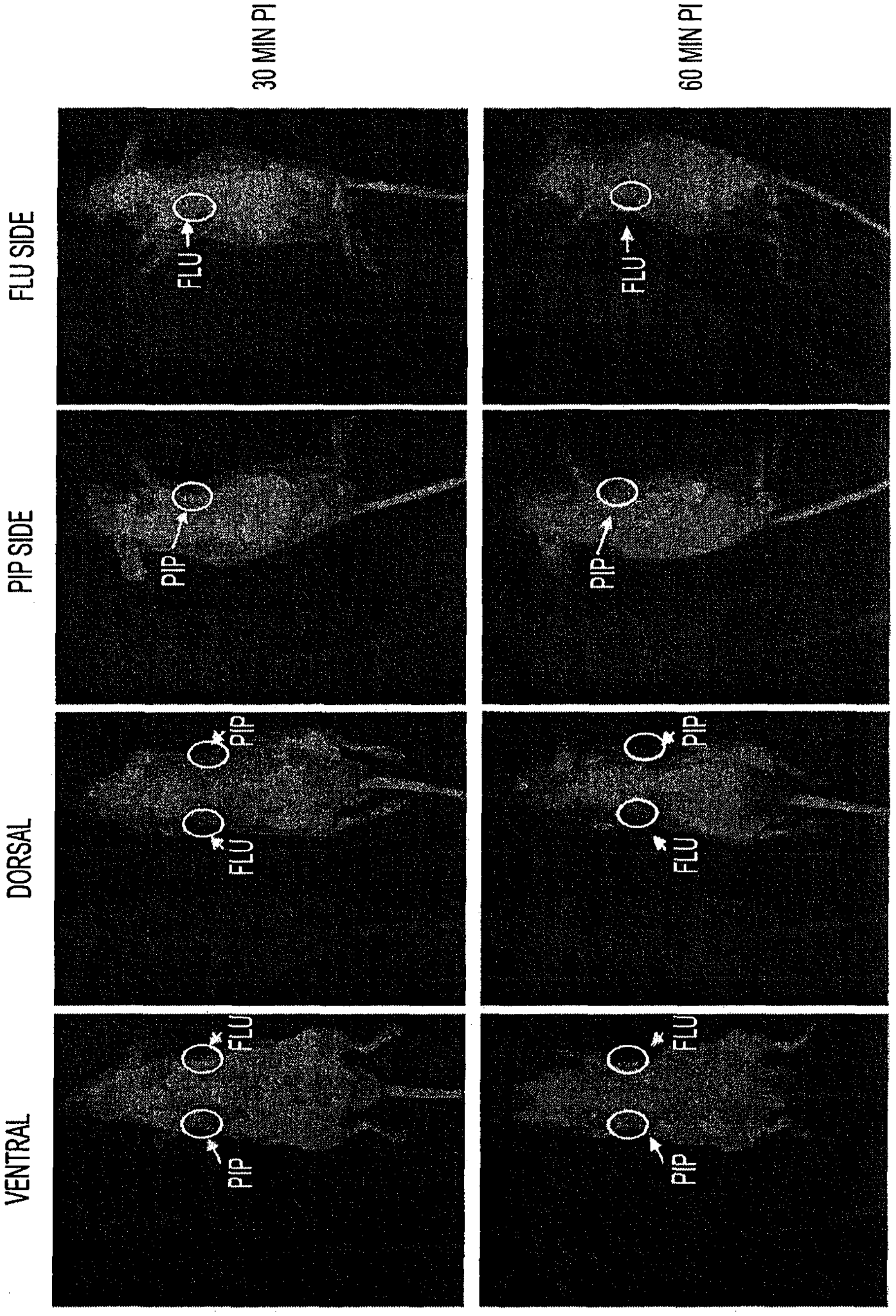
FIG. 21 shows fluorescence images of a PSMA+ PC3-PIP and PSMA− PC3-flu tumor-bearing mouse injected intravenously with exemplary compound YC-VIII-36.
Figure 22:
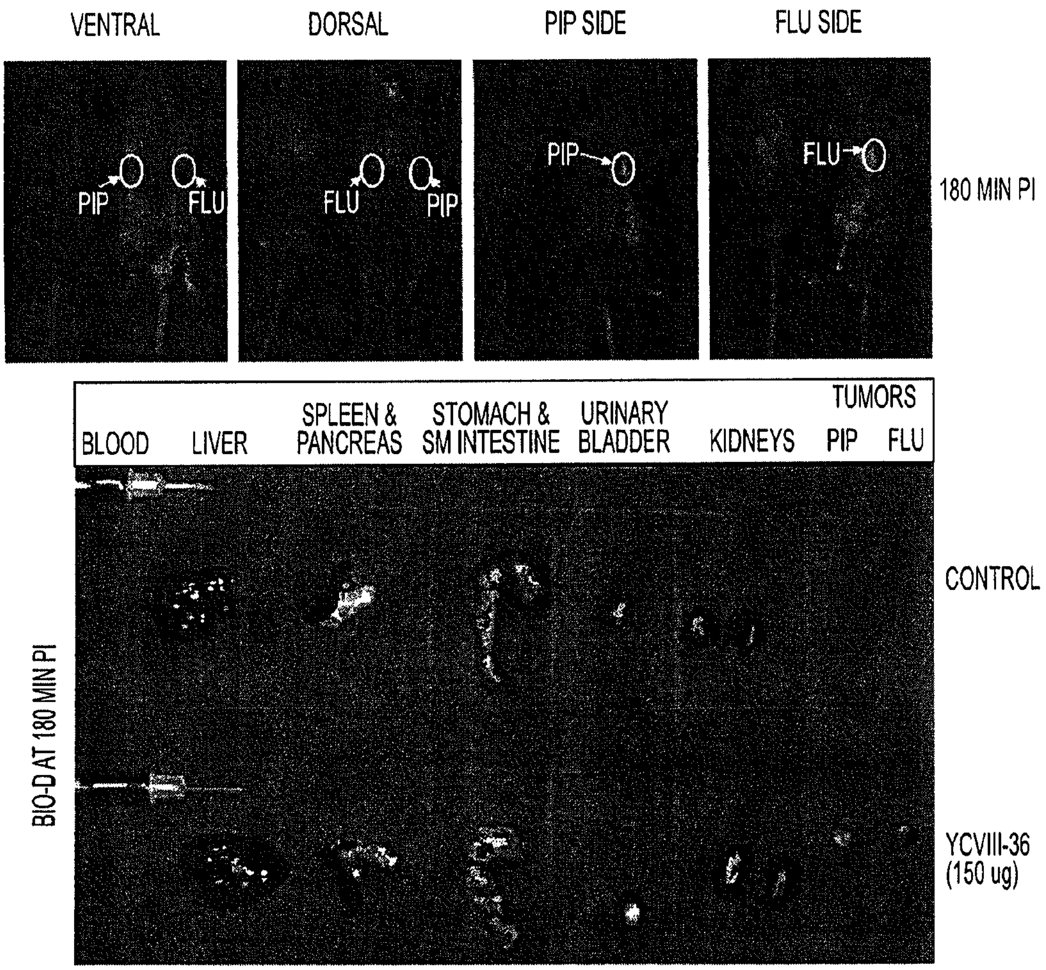
FIG. 22 shows fluorescence images of a PSMA+ PC3-PIP and PSMA− PC3-flu tumor-bearing mouse injected intravenously with exemplary compound YC-VIII-36 180 minutes after injection (top) and biodistribution of exemplary compound YC-VIII-36 180 minutes after injection (bottom).

FIGS. 21 and 22 (top) shows fluorescence images of a PSMA+ PC3-PIP and PSMA− PC3-flu tumor-bearing mouse injected intravenously with exemplary compound YC-VIII-36. Compound YC-VIII-36 (150 μg) was injected into the tail vein of a nude mouse. The excitation frequency was 465 nm with a 5 s exposure. Fluorescence emission was measured at 500, 520, 540, and 580 nm, followed by spectral unmixing.

FIG. 22 (bottom) shows the biodistribution of compound YC-VII-36 (150 μg) 180 minutes after injection.

FACS and Cell Sorting

Flow Cytometric Analysis (FCA):

Confluent flasks of PC3-PIP, PC3-flu and LNCap cells were trypsinized, washed with complete growth media (to neutralize trypsin) and counted. Approximately 5 million of each cell type in suspension was incubated with 1 mM of compound YC-VIII-36 for 30 min with occasional shaking at 37° C. in the humidified incubator with 5% $CO_2$. After incubation, the cells were washed twice with ice cold KRB buffer and fixed with 2% paraformaldehyde (ice cold). The samples were stored on ice and protected from light until the FCA was done. FCA was performed using a FACS Calibur flow cytometer (Becton Dickinson, San Jose, Calif.). For data acquisition, singlets were gated as the prominent cluster of cells identified from a plot of side scatter (SSC) width versus forward scatter (FSC) width to ensure that cell aggregates were excluded from analysis. 50,000 total events were counted to estimate the positively stained cells from a plot of Fl-1 (X-axis) versus Fl-2 (Y-axis). All data were analyzed using CellQuest version 3.3 software.

Flow Sorting:

PC3-PIP cells were labeled with 1 mM of compound YC-VIII-36 for 30 min at 37° C. in the humidified incubator with 5% $CO_2$. Cells were washed twice with ice cold KRB buffer and stored on ice. Flow sorting was performed using FACS Aria system (Becton Dickinson, San Jose, Calif.) within 10-15 minutes after completion of last wash. Both the stained (positive) and also the unstained (negative) subpopulations were collected in sterile tubes containing 3 ml of complete growth media. Following sorting, cells were centrifuged, resuspended in warm complete growth media, transferred to tissue culture flasks and incubated at 37° C. in the humidified incubator with 5% $CO_2$ for culture. The sorted subpopulations, "PIP-positive (PIP-pos)" and "PIP-negative (PIP-neg)" cells, were re-analyzed by FCA (as above) at passage 3 for further confirmation of their heterogeneity.

Determination of Saturation Dose in Flow Cytometry:

Approximately 5 million cells each of PIP-pos (sorted) and PC3-flu were labeled as above with varying doses of compound #. The cells were washed twice with ice cold KRB buffer and fixed with 2% paraformaldehyde (ice cold). The samples were stored on ice and protected from light till the FCA was done. Singlets were gated as above in a plot of SSC vs. FSC to exclude the aggregates. Standard gating was used on X-axis (Fl-1) for analysis of stained cells in all the doses.

Figure 23:
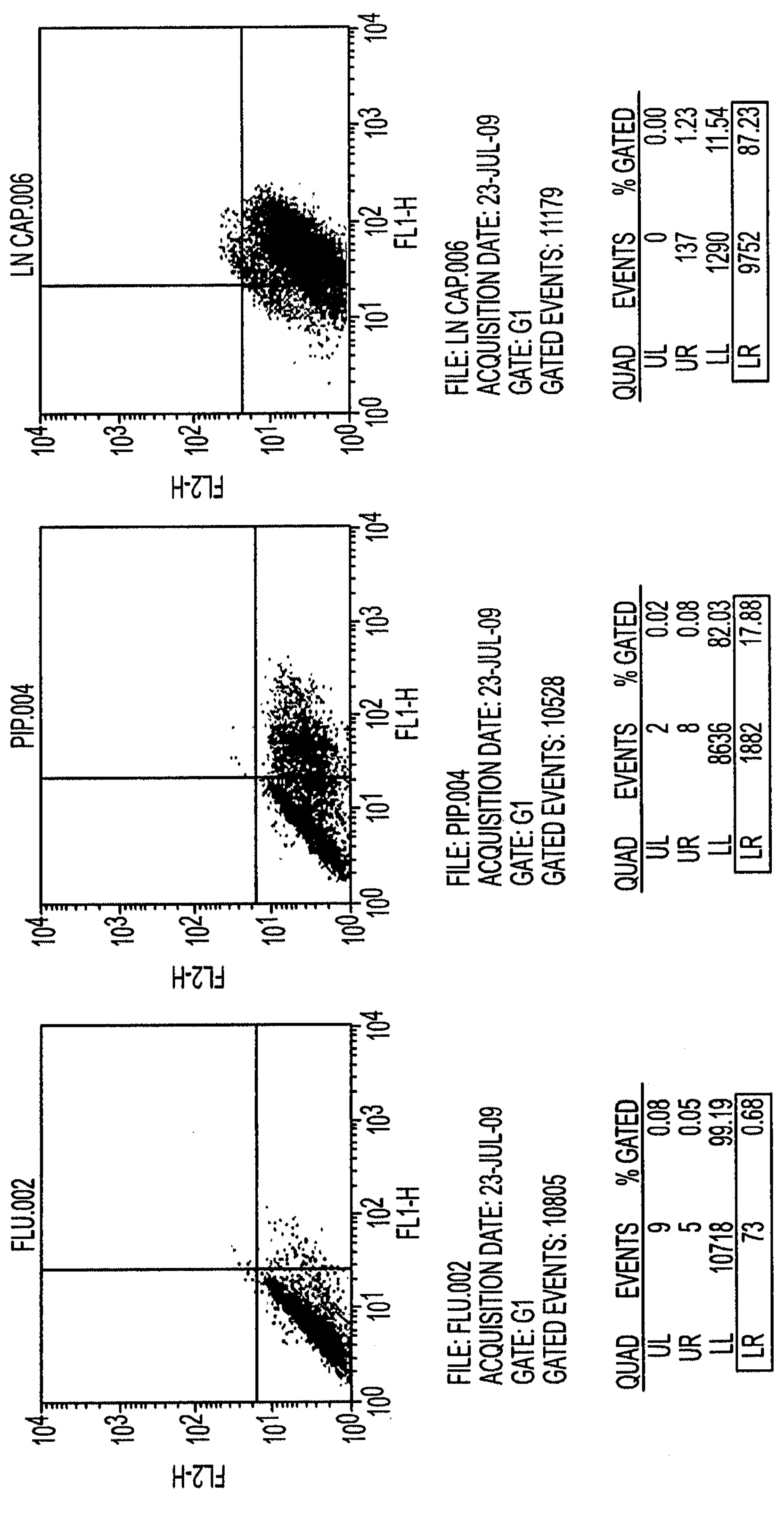
FIG. 23 shows FACS analysis showing the percent subpopulation of PSMA positive cells in PC3-flu, PC3-PIP, and LNCaP cells.

PC3-flu, PC3-PIP, and LNCaP cells were treated with compound YC-VIII-36, and analyzed using fluorescence activated cell sorting (FACS) to determine the percentage of cells expressing PSMA on the cell surface. FIG. 23 shows FACS analysis showing the percent subpopulation of PSMA positive cells in PC3-flu, PC3-PIP, and LNCaP cells. As expected PC3-flu (PSMA−) cells (left) show a very small percentage, while PC3-PIP ($PSMA^+$, center) and LNCaP (PSMA+ right) show greater percentages.

Figure 24:
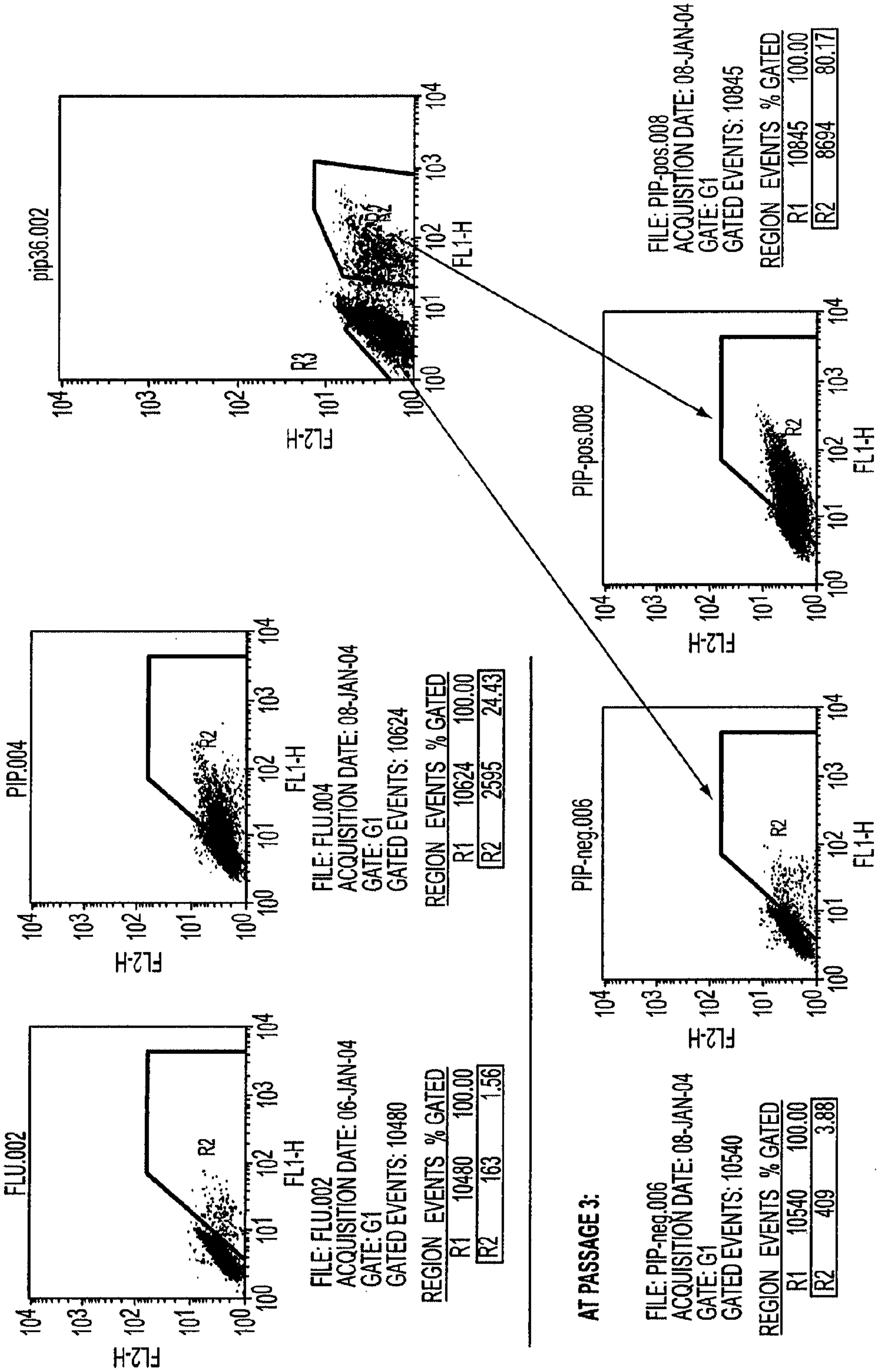
FIG. 24 shows cell sorting results for PC3-PIP cells treated with exemplary compound YC-VIII-36, including initial percentage (top center), and after 3 passages of sorting (bottom).
Figure 25A:
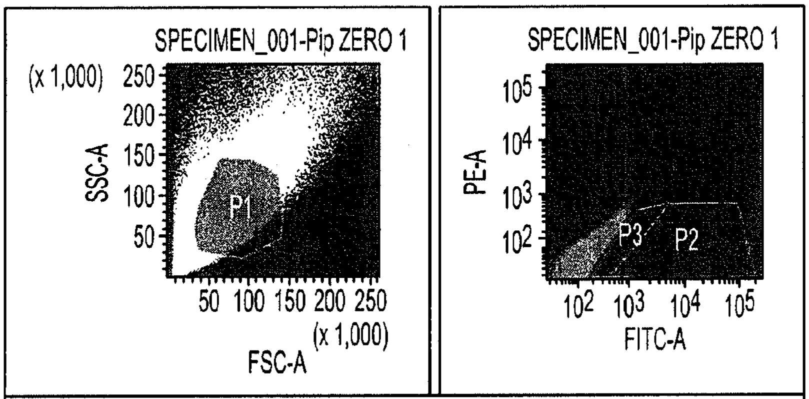
FIG. 25 shows the number of spiked PIP-pos cells into 10 million of PC3-flu detectable by 100 nM compound YC-VIII-36 in flow cytometry (BD LSR-II). Gate P1 is total number of single cells counted; gate P2 at higher intensity is the number of Pip-pos cells detected and gate P3 at lower intensity.
Figure 25A:
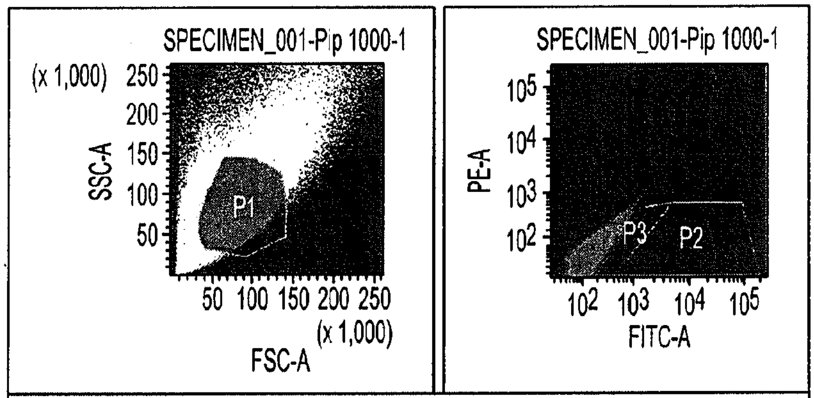
Figure 25B:
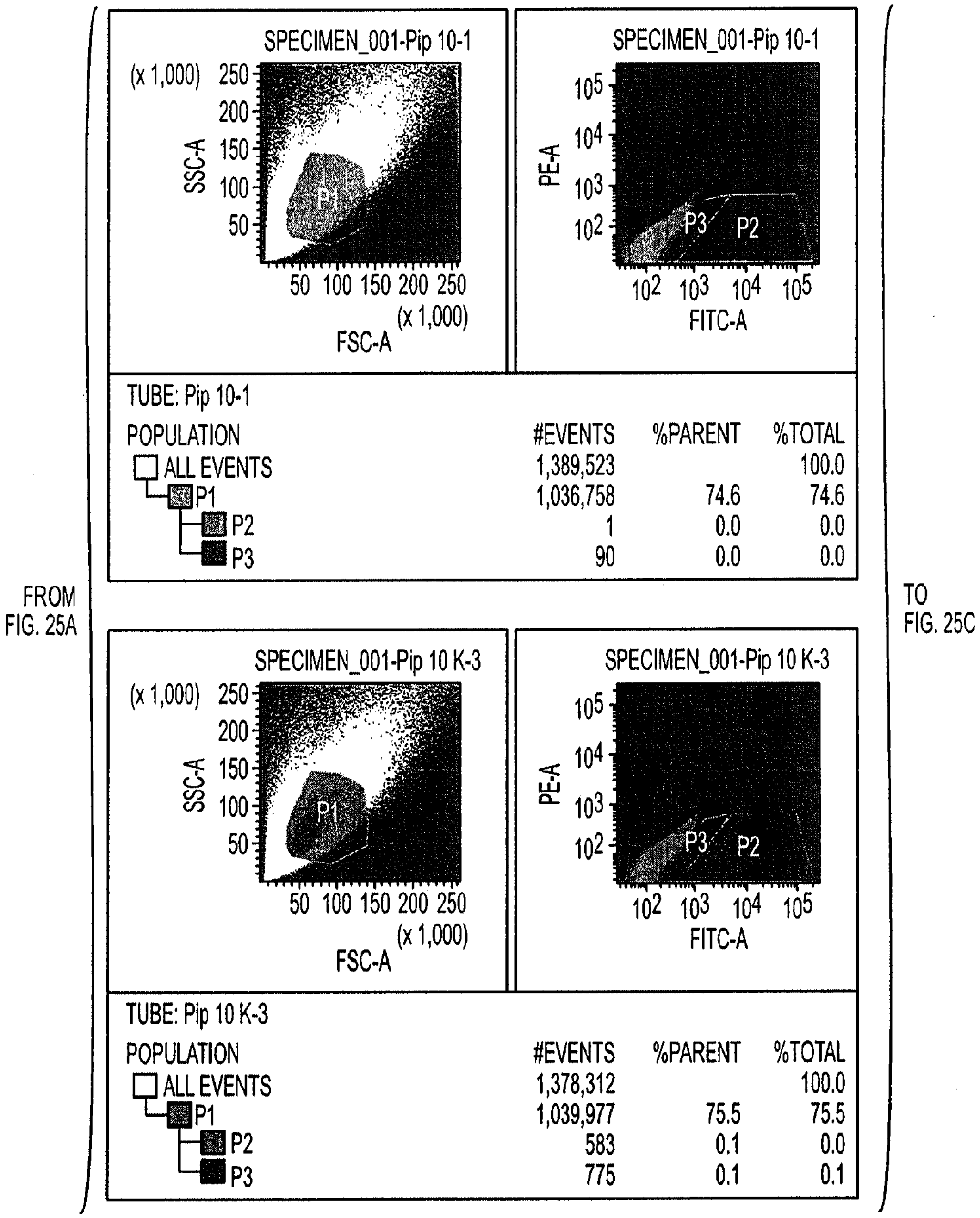
Figure 25C:
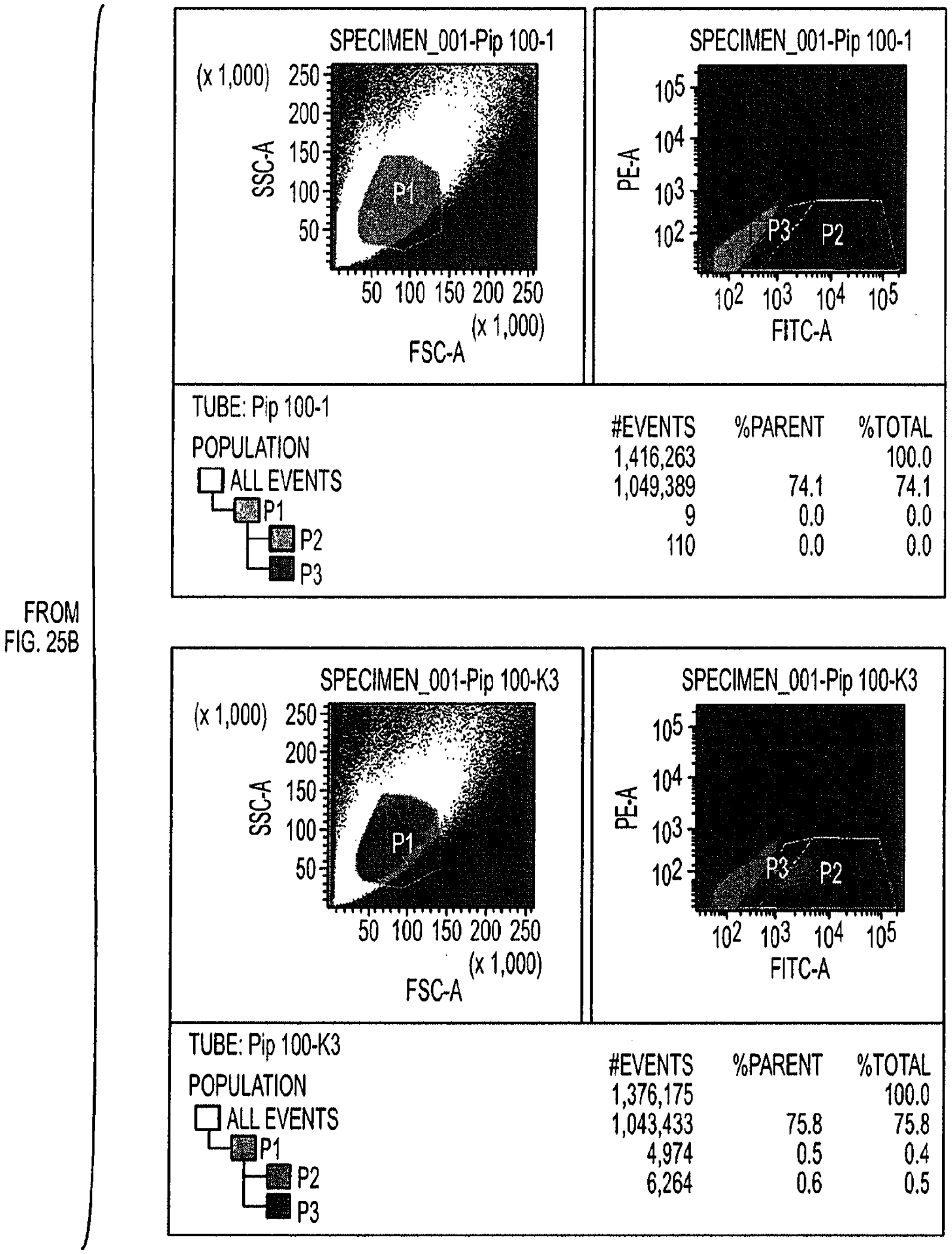

PC3-PIP (PSMA+) cells were sorted using FACS following treatment with compound YC-VIII-36. FIG. 24 shows cell sorting of PC3-PIP cells, including initial percentage (top center), and after 3 passages of sorting (bottom). Region R2 indicates positive PSMA surface expression, as indicated by binding compound YC-VIII-36. The results show an increase in the percentage of PSMA expressing cells following three rounds of cell sorting.

Determination of Detection Limit (FIG. 25):

PIP-pos cells were mixed with 10 million of PC3-flu cells in triplicates in different ratios-1 in $10^6$, $10^5$, $10^4$, $10^3$ and $10^2$ respectively. All the tubes containing cell suspensions in complete growth media including controls [10 million PC3-flu cells with 0% PIP-pos cells and 10 million PIP-pos cells (100%)] were incubated with 100 nM of compound # YC-VIII-36 at 37° C. in the humidified incubator with 5% $CO_2$ as above, with occasional stirring. The cells were washed, fixed with 2% paraformaldehyde as above and analyzed with LSRII (Becton Dickinson, San Jose, Calif.) for the determination of detection limit. Singlets were gated as above in a plot of SSC vs. FSC to exclude the aggregates. 1 million total events were counted to estimate the positively stained cells from plot of Fl-1 (X-axis) versus Fl-2 (Y-axis). Two gates, P2 at higher intensity (103 and above) and P3 at lower intensity (102-103) on X-axis (Fl-1) was applied for analysis of positive cells as described in FIG. 4. All the data were analyzed using DIVA 6.1.3 software.

The invention claimed is:

1. A compound having the structure:

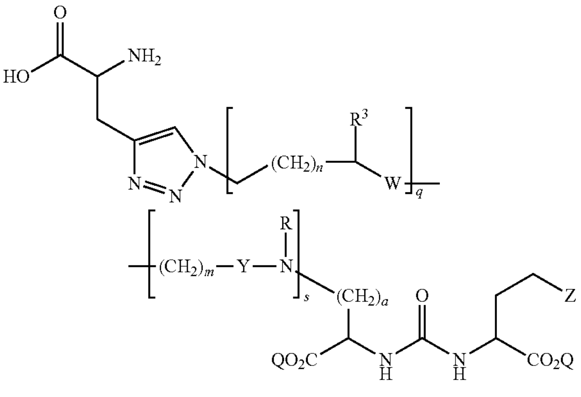

wherein Z is $CO_2Q$; each Q is hydrogen; each R is independently H or $C_1$-$C_4$ alkyl; W is —NRC(O)—; Y is —C(O)—; a is 1, 2, 3, or 4; m is 1, 2, 3, 4, 5, or 6; n is 1, 2, 3, 4, 5 or 6; q is 1; s is 1; and $R^3$ is H, $CO_2H$, or $CO_2R^4$, where $R^4$ is a $C_1$-$C_6$ alkyl and optionally including a chelated Tc-99m metal ion.

2. The compound according to claim 1 having the structure
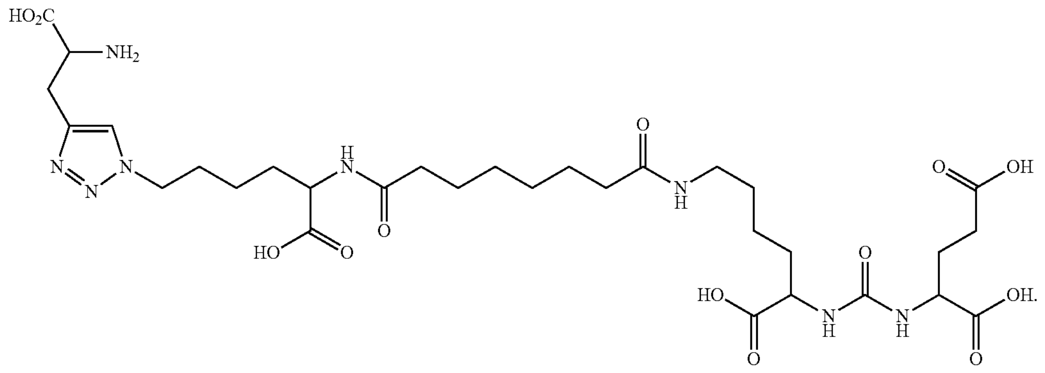 [SMILES: NC(Cc1cn(CCCCC(NC(=O)CCCCCCC(=O)NCCCCC(NC(=O)NC(CCC(=O)O)C(=O)O)C(=O)O)C(=O)O)nn1)C(=O)O]
3. The compound according to claim 1 further comprising a chelated Tc-99m metal ion.
* * * * *